(12) United States Patent
Lucas

(10) Patent No.: US 10,610,404 B2
(45) Date of Patent: Apr. 7, 2020

(54) SYSTEMS AND METHODS FOR PRODUCING ANTERIOR GUIDANCE PACKAGE (AGP) EQUIPPED SPLINT

(71) Applicant: Kelly Lucas, Wasilla, AK (US)

(72) Inventor: Kelly Lucas, Wasilla, AK (US)

(73) Assignee: Kelly Lucas, Wasilla, AK (US)

( * ) Notice: Subject to any disclaimer, the term of this patent is extended or adjusted under 35 U.S.C. 154(b) by 1323 days.

(21) Appl. No.: 14/748,805

(22) Filed: Jun. 24, 2015

(65) Prior Publication Data

US 2016/0378883 A1    Dec. 29, 2016

(51) Int. Cl.
*A61F 5/56*    (2006.01)

(52) U.S. Cl.
CPC .............. *A61F 5/566* (2013.01); *A61F 5/56* (2013.01); *A61F 2005/563* (2013.01)

(58) Field of Classification Search
CPC ....... A61F 5/566; A61F 5/56; A61F 2005/563
See application file for complete search history.

(56) References Cited

U.S. PATENT DOCUMENTS

| | | | |
|---|---|---|---|
| 2,529,429 A | 11/1950 | Spiro | |
| 4,773,854 A | 9/1988 | Weber | |
| 4,901,737 A | 2/1990 | Toone | |
| 5,059,120 A | 10/1991 | Lee | |
| 5,085,584 A | 2/1992 | Boyd | |
| 5,203,701 A | 4/1993 | Burtch | |
| 5,365,945 A | 11/1994 | Halstrom | |
| 5,427,117 A | 6/1995 | Thornton | |
| 5,722,828 A | 3/1998 | Halstrom | |
| 5,795,150 A | 8/1998 | Boyd | |
| 5,868,138 A | 2/1999 | Halstrom | |
| 6,041,784 A | 3/2000 | Halstrom | |
| 6,161,542 A | 12/2000 | Halstrom | |
| 6,431,871 B1 * | 8/2002 | Luthardt | A61C 13/0004 433/223 |
| 6,666,212 B2 | 12/2003 | Boyd, Sr. | |
| 6,886,566 B2 | 5/2005 | Eubank | |

(Continued)

FOREIGN PATENT DOCUMENTS

| | | | |
|---|---|---|---|
| EP | 0312368 A1 | 4/1989 | |
| WO | WO2007084820 | * 7/2007 | ............... H05G 1/64 |

OTHER PUBLICATIONS

"Component". Oxford English Dictionary [retrieved on May 8, 2019]. Retrieved from <http://www.oed.com/view/Entry/37759?redirectedFrom=component#eid> (Year: 2019).*

(Continued)

*Primary Examiner* — Rehana Perveen
*Assistant Examiner* — Alfred H B Wechselberger
(74) *Attorney, Agent, or Firm* — Troutman Sanders LLP; Dustin B. Weeks; Brennan M. Carmody

(57) ABSTRACT

An Anterior Guidance Package (AGP) equipped splint may be produced for a patient with bruxism, temporo mandibular disorder (TMD), or sleep apnea. The AGP equipped splint has maxillary and mandibular guidance components attached to respective retentive pieces to provide superior anterior guidance. Using the disclosed systems and methods for producing the AGP equipped splint, a patient with or without a severe malocclusion can receive a customized AGP equipped splint without visiting the dentist repeatedly.

20 Claims, 35 Drawing Sheets

(56) References Cited

U.S. PATENT DOCUMENTS

| | | | |
|---|---|---|---|
| 7,556,044 | B2 | 7/2009 | Ball |
| 7,654,267 | B2 | 2/2010 | Boyd |
| 8,156,940 | B2 | 4/2012 | Lee |
| 2002/0000230 | A1 | 1/2002 | Gaskell |
| 2004/0172150 | A1* | 9/2004 | Perot ............... A61C 9/004 700/98 |
| 2005/0288624 | A1 | 12/2005 | Boyd |
| 2006/0003292 | A1* | 1/2006 | Lauren ............. A61C 5/007 433/215 |
| 2007/0079833 | A1 | 4/2007 | Lamberg |
| 2007/0099144 | A1 | 5/2007 | Keski-Nisula |
| 2007/0178420 | A1 | 8/2007 | Keski-Nisula |
| 2008/0000483 | A1 | 1/2008 | Halstrom |
| 2008/0099029 | A1 | 5/2008 | Lamberg |
| 2010/0147315 | A1 | 6/2010 | Chodorow |
| 2010/0279246 | A1 | 11/2010 | Keski-Nisula |
| 2011/0030704 | A1 | 2/2011 | Hanna |
| 2011/0114100 | A1 | 5/2011 | Alvarez |
| 2011/0139162 | A1 | 6/2011 | Chodorow |
| 2011/0308532 | A1 | 12/2011 | Nelissen |
| 2012/0266896 | A1 | 10/2012 | Chodorow |
| 2012/0266897 | A1 | 10/2012 | Chodorow |
| 2012/0272972 | A1 | 11/2012 | Chodorow |
| 2013/0098375 | A1 | 4/2013 | Urbansk |
| 2013/0146067 | A1 | 6/2013 | Tschackert |
| 2014/0060549 | A1* | 3/2014 | Lucas ............... A61F 5/566 128/861 |
| 2015/0000677 | A1* | 1/2015 | Magness ........... A61F 5/566 128/861 |
| 2015/0075542 | A1* | 3/2015 | Robichaud ........ A61F 5/566 128/861 |
| 2015/0210014 | A1* | 7/2015 | Hultgren ........... A61F 5/566 128/845 |
| 2016/0135925 | A1* | 5/2016 | Mason .............. A61C 7/002 703/2 |
| 2019/0216580 | A1* | 7/2019 | Fisker .............. A61C 11/00 |

OTHER PUBLICATIONS

3DBioCAD "3D BioCAD—3Shape Implant Studio Step by Step Guide" [retrieved on May 6, 2019]. Retrieved from <https://www.youtube.com/watch?v=NeZi0taR5Y0> (Year: 2014).*

LabMagic 3D CAD "How to design a Bite Splint in 3Shape" Mar. 1, 2015 [retrieved on May 6, 2019]. Retrieved from <https://www.youtube.com/watch?v=6uZFVckB4hY> (Year: 2015).*

University of Michigan, School of Dentistry, "Articulator Demonstration" [retrieved on May 6, 2019]. Retrieved from <https://www.youtube.com/watch?v=x9xm3aGXW_k> (Year: 2009).*

LabMagic 3D CAD. "How to design a Damon Sleep Splint" Feb. 2, 2015 [retrieved on May 6, 2019]. Retrieved from <https://www.youtube.com/watch?v=xJ_NwlLKp-4> (Year: 2015).*

Lauren et al. "A new computer-assisted method for design and fabrication of occlusal splints" Amer. Jour. of Orthodontics and Dentofacial Orthopedics, vol. 133, No. 4, Suppl. 1, pp. 130-135 [retrieved on Nov. 19, 2019]. Retrieved from <https://www.sciencedirect.com/science/article/pii/S0889540607013728> (Year: 2008).*

Laura Maestre-Ferrin, et al., "Virtual articulator for the analysis of dental occlusion: An update," Med Oral Patol Oral Cir Bucal. vol. 17(1): e160-a163, Jan. 2012.

E. Solaberrieta, et al., "Design of a Virtual Articulator for the Simulation and Analysis of Mandibular Moments in Dental CAD/CAM," Proceedings of the 19th CIRP Design Conference-Competitive Design, pp. 323, 330-331, Mar. 2009.

Frank, et al., "Great Lakes Digital Splint," http://www.greatlakesortho.com/resource-center/digital-splints-users-group; accessed May 19, 2015.

www.chairsidesplint.com—NTI-tss Bevies, accessed May 19, 2015.

Spear, Dr. Frank M., et al., "Great Lakes Splint Appliance Selection Guide" accessed on May 19, 2015, http://www.greatlakesortho.com/content/files/resources/SplintApplianceSelectionGuide_S222.pdf.

* cited by examiner

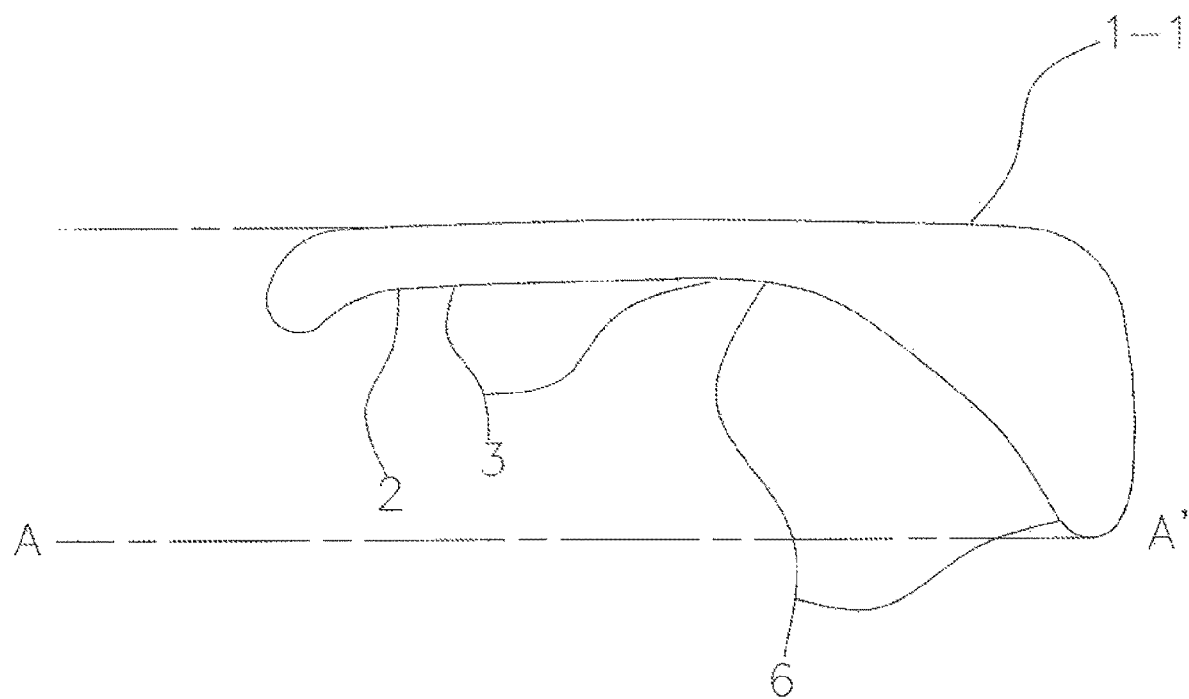
FIG. 2-a

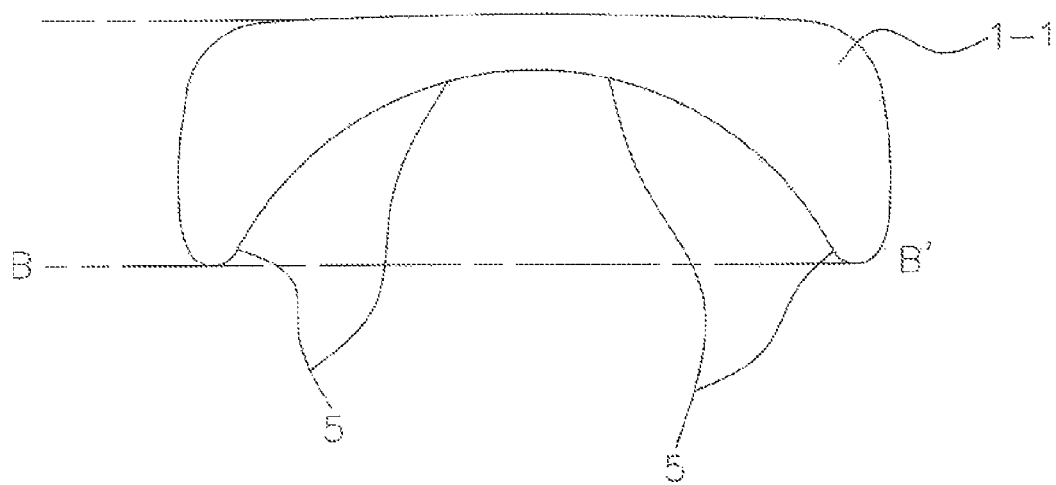
FIG. 2-b

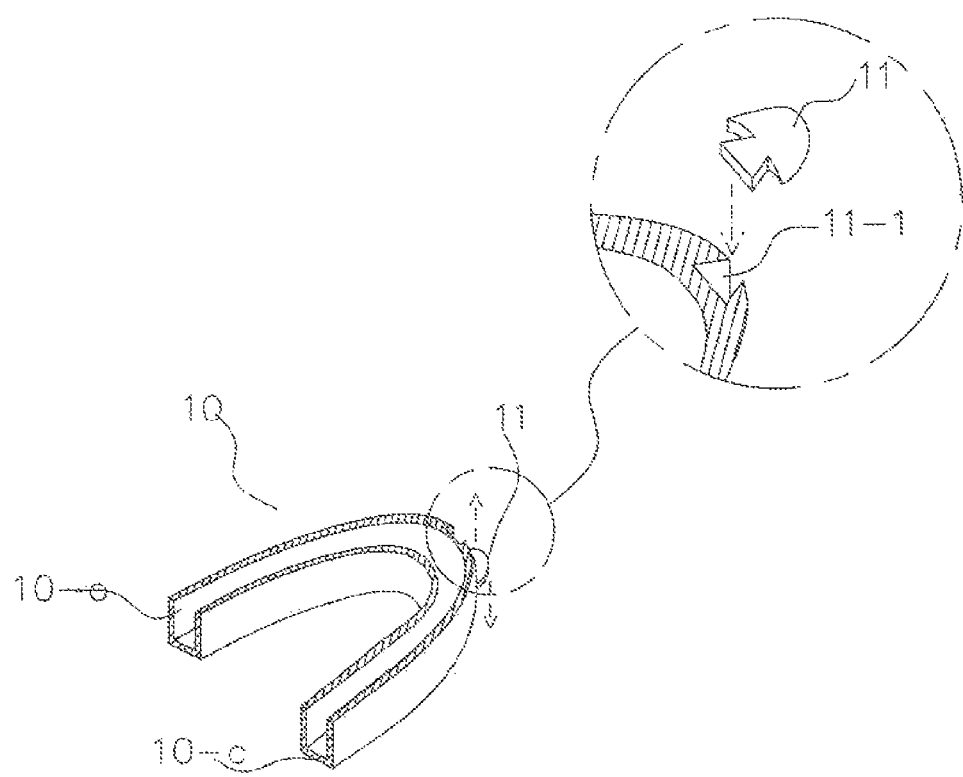
FIG. 5-a

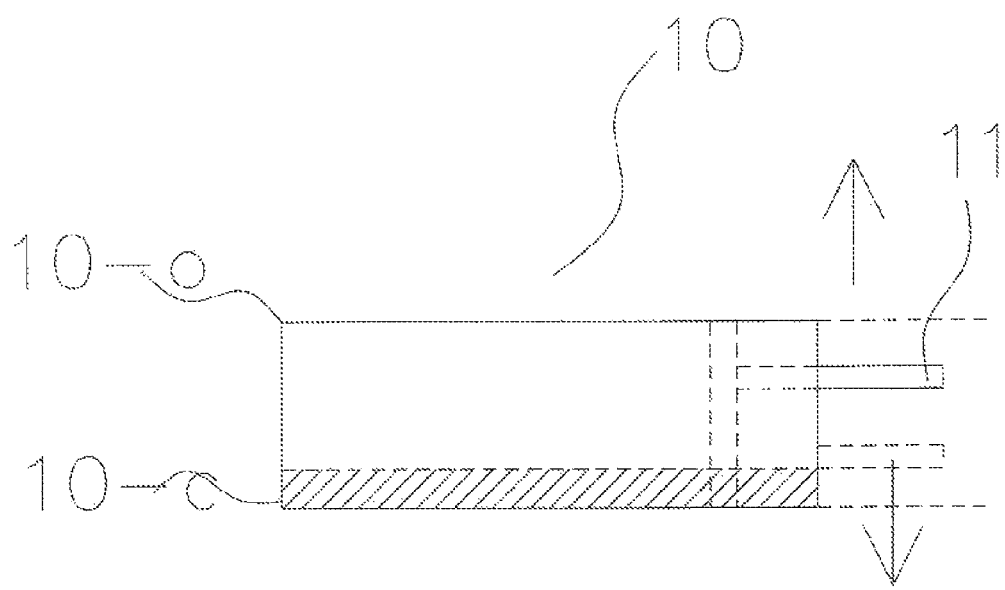
FIG. 5-b

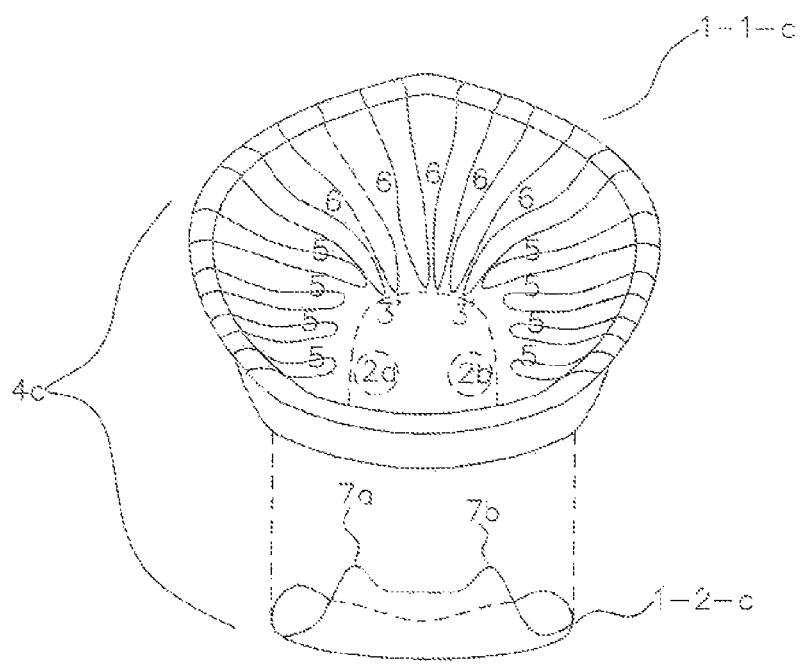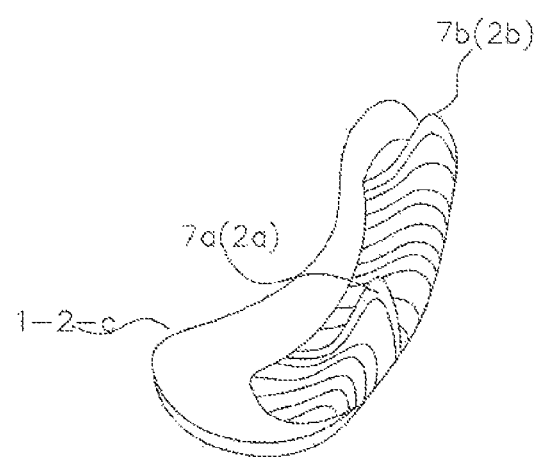
FIG. 9

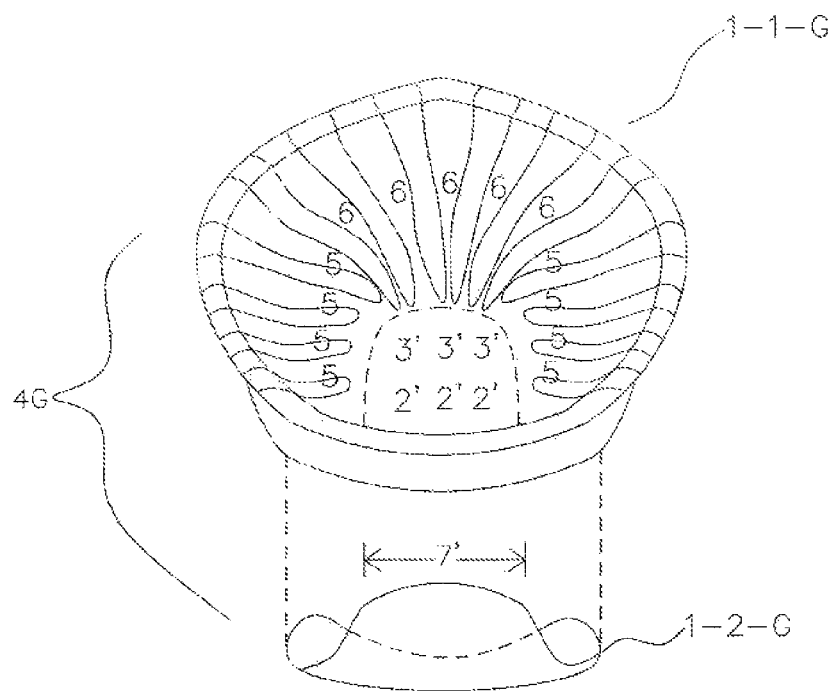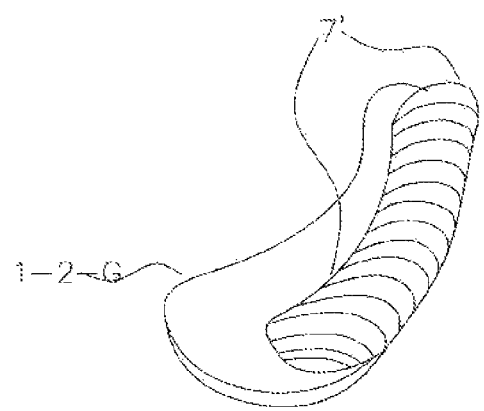
FIG. 10

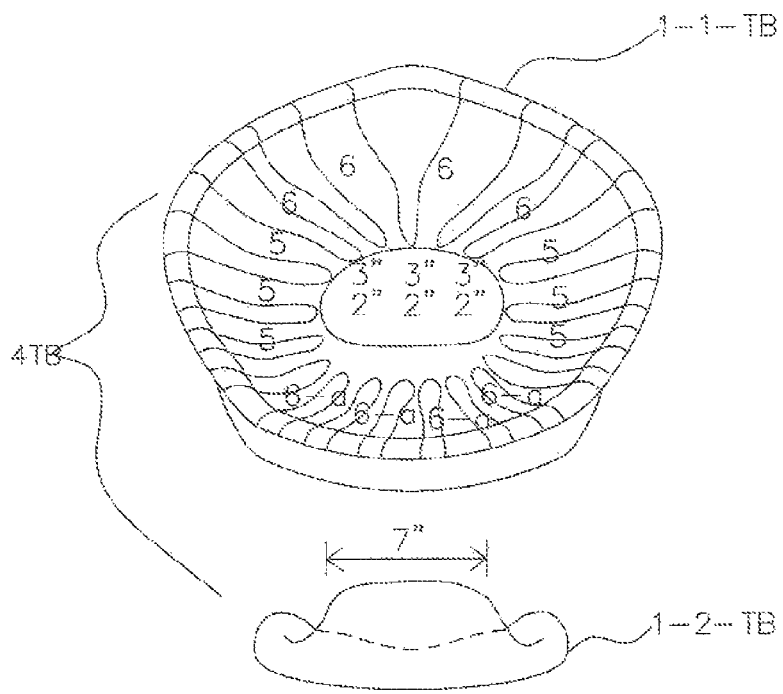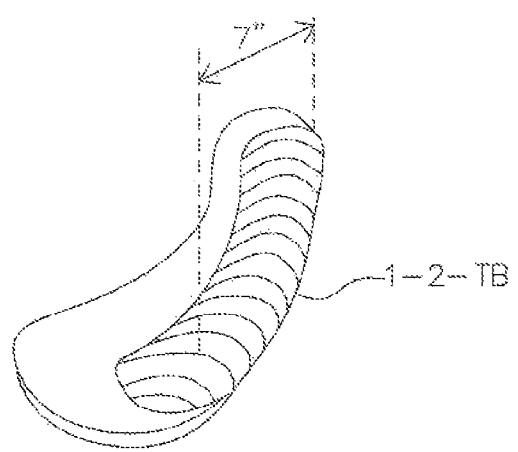
FIG. 11

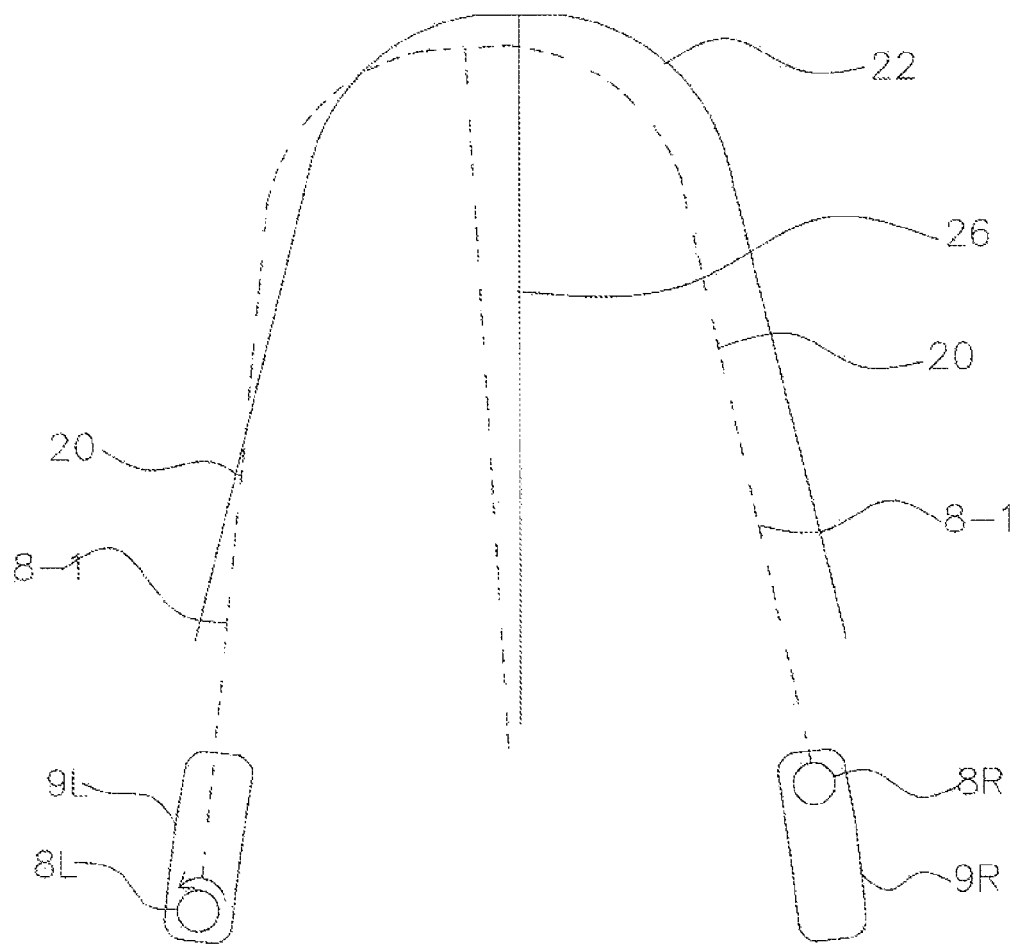
FIG. 11-a

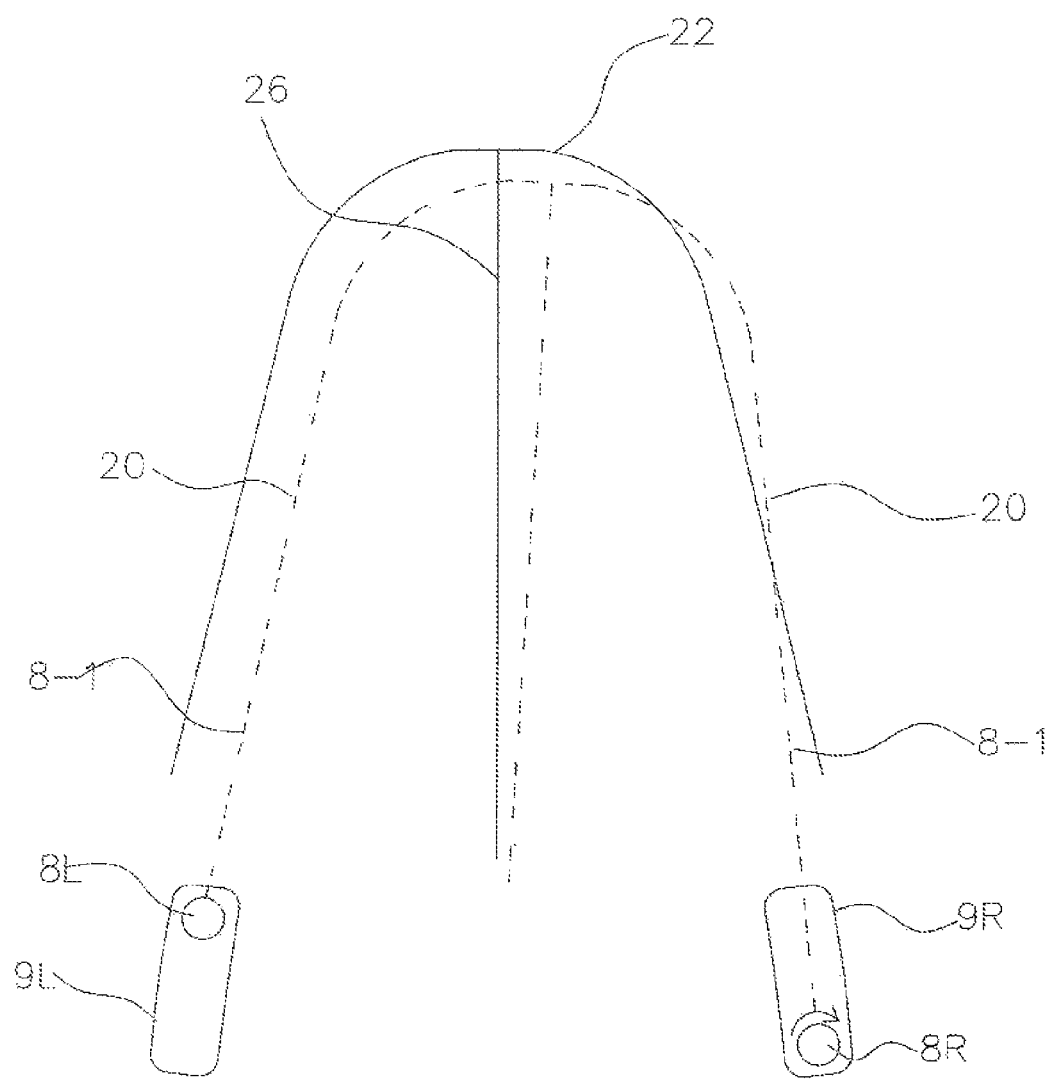
FIG. 11-b

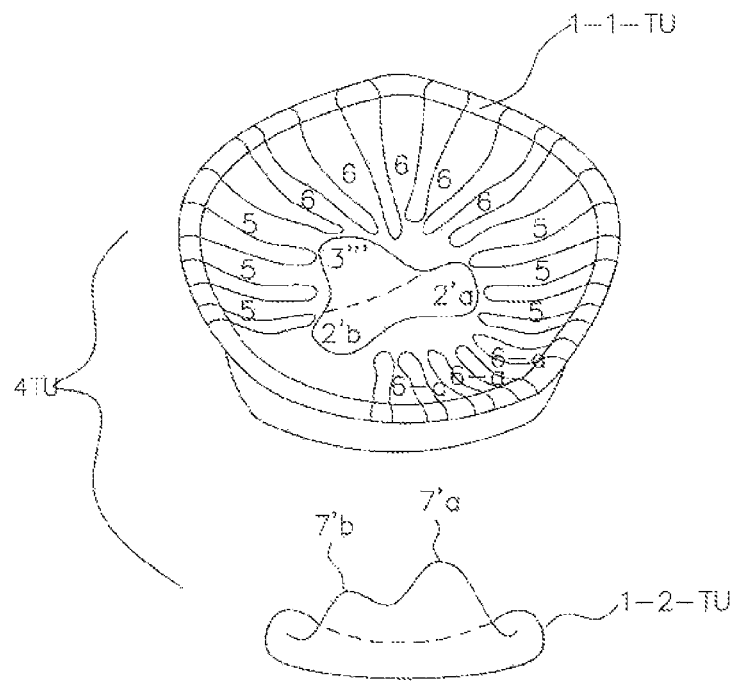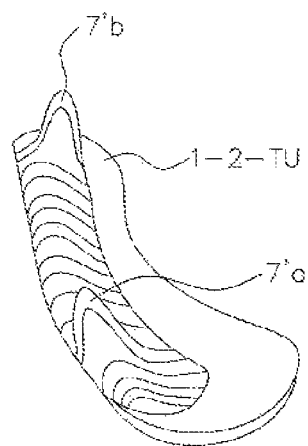
FIG. 12-a

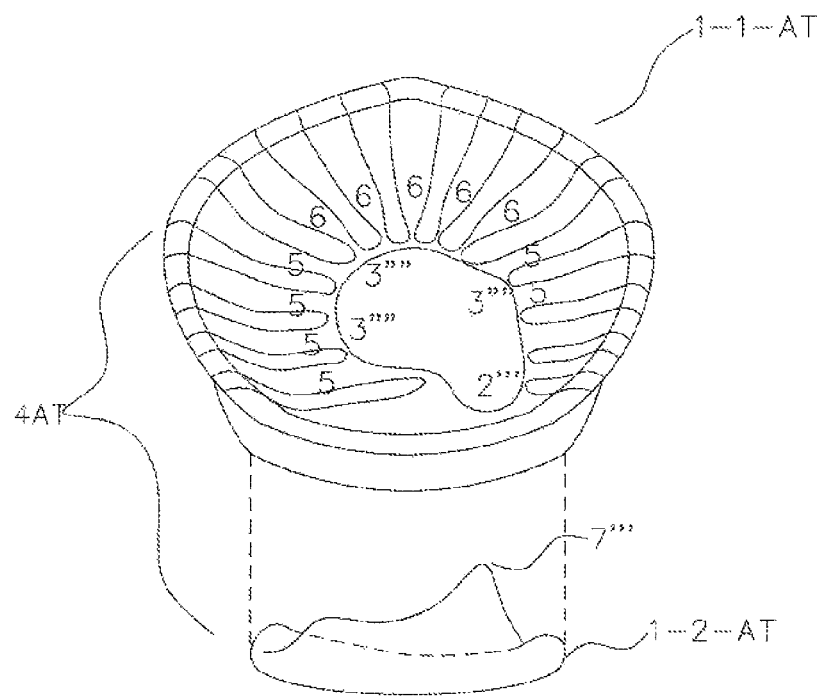
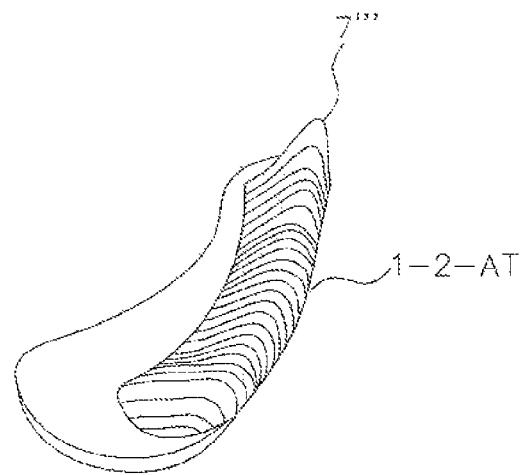
FIG. 13

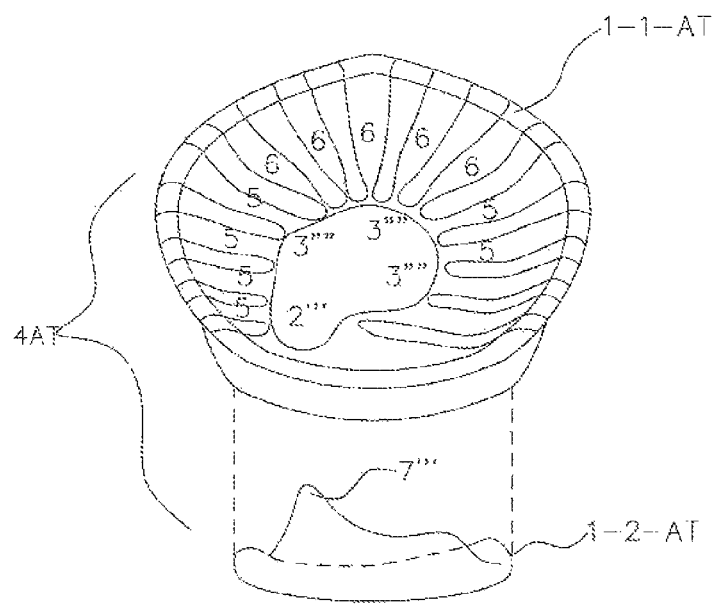
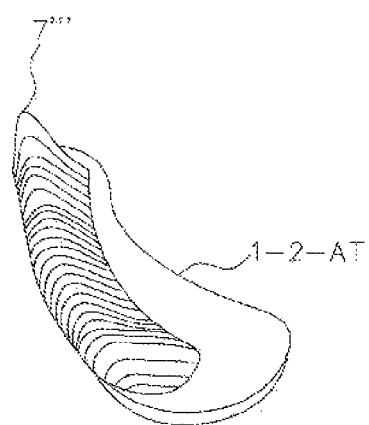
FIG. 13-a

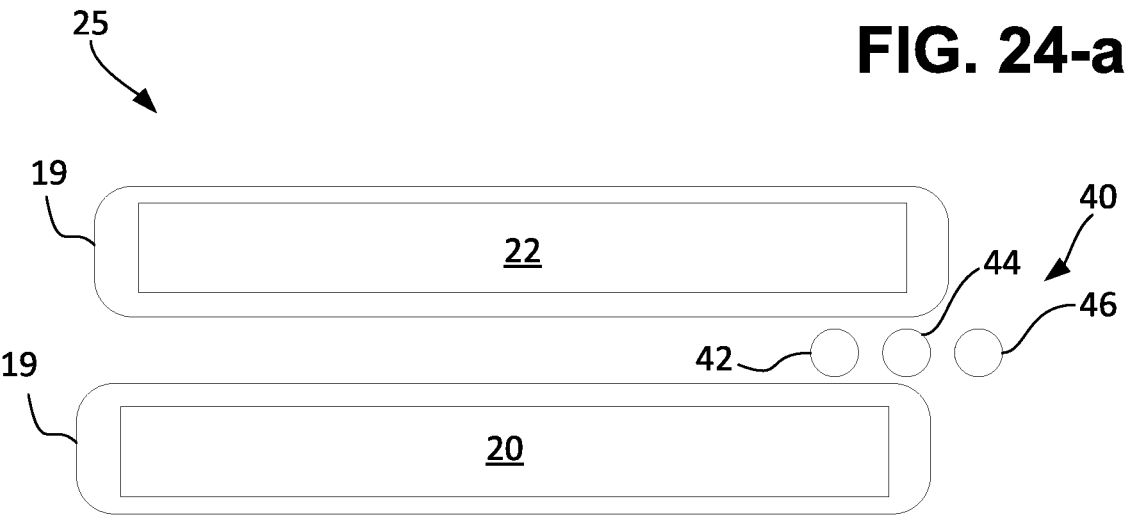
FIG. 24-a
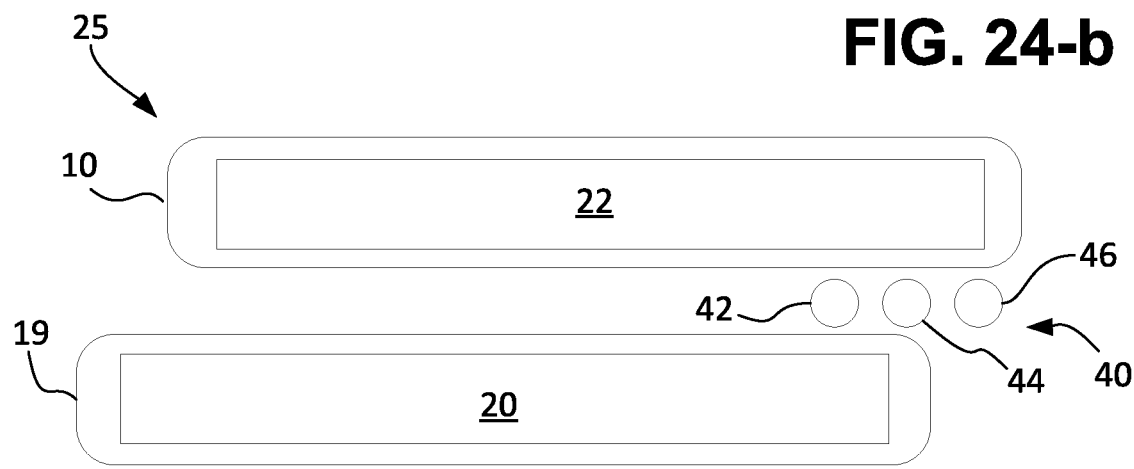
FIG. 24-b
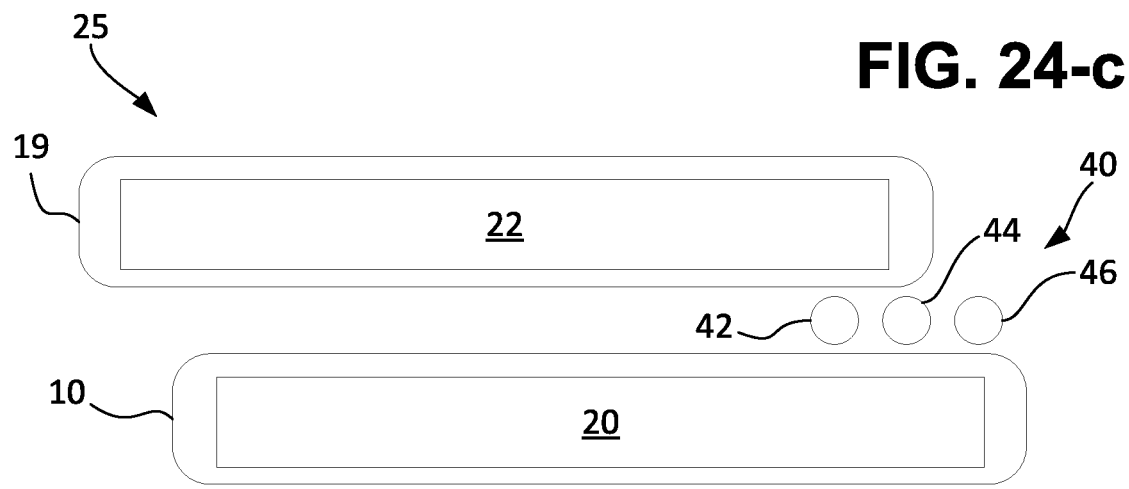
FIG. 24-c
FRONT →

SYSTEMS AND METHODS FOR PRODUCING ANTERIOR GUIDANCE PACKAGE (AGP) EQUIPPED SPLINT

FIELD OF THE INVENTION

The presently disclosed subject matter relates generally to systems and methods for producing an Anterior Guidance Package (AGP) equipped splint, particularly systems and methods for producing an AGP equipped splint for a patient with or without a severe malocclusion, with or without bruxism, with or without a Temporo Mandibular Disorder (TMD), and with or without sleep apnea.

BACKGROUND

Bruxism is an involuntary or habitual grinding of the teeth, typically during sleep, which undesirably causes many dental and medical problems. For example, bruxism has been known to cause myo-facial pain syndrome, damage to teeth, and damage to the temporomandibular joints (TMJs). Incorrect or inadequate treatment of bruxism can amplify its effects.

Many types of night guards have been designed to help address the negative impacts of bruxism. Some night guards simply cover the teeth to prevent wear, while others aim to correct the centric relation (CR)/centric occlusion (CO) discrepancy to allow the TMJ to relax in its most anatomically appropriate and best stress bearing position, which is centric relation for most patients. Other night guards provide anterior guidance, which, among other benefits, significantly reduces the inappropriate muscle force associate with bruxism and guides the jaw to avoid posterior interferences. The best night guards protect the teeth, address the CR/CO discrepancy, and provide anterior guidance, as failing to address all three aspects can often increase the severity of bruxism.

Traditionally, dental professionals have constructed customized night guards that are typically attached to the maxillary and/or mandibular teeth. The customized night guards allow the dental professional to consider a patient's particular malocclusion and other factors to place the patient's jaw in centric relation or another predetermined index position. While helpful, these customized night guards typically require substantial time and effort to create and modify for each patient, and later replace once the night guard is damaged or lost. Existing night guards may also be limited for patients with missing or periodontally weakened teeth or specific malocclusions, and only provide limited anterior guidance.

Accordingly, there is a need for improved systems and methods to address the above mentioned deficiencies. Embodiments of the present disclosure are directed to these and other considerations.

SUMMARY

Briefly described, embodiments of the presently disclosed subject matter relate to a systems and methods for preparing an Anterior Guidance Package (AGP) equipped splint for a patient with one or more of bruxism, temporomandibular disorder (TMD), and sleep apnea.

Specifically, in some embodiments, the method may include obtaining patient data comprising three dimensional arch data associated with the patient. After obtaining the patient data, one or more digital models may be generated on one or more processors based on the patient data. The one or more digital models may include virtual maxillary and mandibular arches. The method may also include determining an index position for the patient. The virtual maxillary and mandibular arches may be positioned in the index position. Further, the method may include separating the virtual maxillary and mandibular arches based on an arc of closure associated with the patient to provide a threshold clearance. A virtual maxillary retentive piece may be applied to the virtual maxillary arch and a virtual mandibular retentive piece may be applied to the virtual mandibular arch. One or more virtual points may be generated based on one or more of the index position and a position, orientation, or position of one of the retentive pieces. A virtual AGP package may be positioned in virtual space based on the one or more virtual points. The AGP package may include a virtual maxillary guidance component and a virtual mandibular guidance component. After positioning the AGP package in virtual space, the virtual maxillary guidance component may be connected to the virtual maxillary retentive piece to form a first part of a virtual AGP equipped splint. Similarly, the virtual mandibular guidance component may be connected to the virtual mandibular retentive piece to form a second part of the virtual AGP equipped splint. AGP equipped splint production data based on the first and second parts of the virtual AGP equipped splint can then be transmitted. For example, the AGP equipped splint production data may be transmitted to a manufacturer equipped with one or more of CAM, CNC technology, and an in-office 3D printer.

A system for preparing an AGP equipped splint for a patient with one or more of bruxism, TMD, and sleep apnea is also disclosed herein. In some embodiments, the system may include a data module configured to obtain patient data comprising three dimensional arch data associated with the patient. The system may also include a modeling module configured to generate one or more digital models on one or more processors based on the patient data, the one or more digital models comprising virtual maxillary and mandibular arches. The system may further include a determination module configured to determine an index position for the patient. An arch positioning module of the system may be configured to position the virtual maxillary and mandibular arches in the index position. The system may include a separation module configured to separate the virtual maxillary and mandibular arches based on an arc of closure associated with the patient to provide a threshold clearance. The system may further include an application module configured to apply a virtual maxillary retentive piece to the virtual maxillary arch and a virtual mandibular retentive piece to the virtual mandibular arch. A generation module of the system may be configured to generate one or more virtual points based on one or more of the index position and a position, orientation, or position of one of the retentive pieces. An AGP positioning module of the system may be configured to position a virtual AGP package in virtual space based on the one or more virtual points, the AGP package comprising a virtual maxillary guidance component and a virtual mandibular guidance component. The system may include a maxillary connection module configured to connect the virtual maxillary guidance component to the virtual maxillary retentive piece to form a first part of a virtual AGP equipped splint. The system may also include a mandibular connection module configured to connect the virtual mandibular guidance component to the virtual mandibular retentive piece to form a second part of the virtual AGP equipped splint. Further, the system may include a transmission module configured to transmit AGP equipped splint production data based on the first and second parts of the virtual AGP equipped splint.

A non-transitory computer-readable storage medium having stored computer-executable instructions that, when executed by one or more processors, cause a computer to perform functions for preparing an AGP equipped splint is also disclosed herein. In some embodiments, the instructions may include obtaining patient data comprising three dimensional arch data associated with the patient. The instructions may also include generating one or more digital models on one or more processors based on the patient data, the one or more digital models comprising virtual maxillary and mandibular arches. The instructions may further include determining an index position for the patient. The virtual maxillary and mandibular arches may be positioned in the index position according to the instructions. The virtual maxillary and mandibular arches may be separated based on an arc of closure associated with the patient to provide a threshold clearance. The instructions may include applying a virtual maxillary retentive piece to the virtual maxillary arch and a virtual mandibular retentive piece to the virtual mandibular arch. The instructions may also include generating one or more virtual points based on one or more of the index position and a position, orientation, or position of one of the retentive pieces. The instructions may further include positioning a virtual AGP package in virtual space based on the one or more virtual points. The AGP package may include a virtual maxillary guidance component and a virtual mandibular guidance component. The instructions may include connecting the virtual maxillary guidance component to the virtual maxillary retentive piece to form a first part of a virtual AGP equipped splint. Similarly, the virtual mandibular guidance component may be connected to the virtual mandibular retentive piece to form a second part of the virtual AGP equipped splint. Further, the instructions may include transmitting AGP equipped splint production data based on the first and second parts of the virtual AGP equipped splint.

In some embodiments, the AGP equipped splint may be a splint that provides three-dimensional control, guidance and limits to the front end of the mandible. The AGP may be indexed within a wide range transversely in the splint system to produce a superior, seamless AGP splint for the bruxism patient, a sophisticated Temporo-Mandibular Disorders (TMDs) AGP splint produced with specific jaw repositioning and guidance limitations as proscribed by a dental professional, or a mandibular protrusive repositioning sleep apnea appliance. The AGP equipped splint may have a unique ability to provide anterior guidance in the splint system within a broad transverse range to include anterior to the teeth therefore enhancing the mechanical advantage over the muscles of mastication. The AGP equipped splint may provide three-dimensional anterior guidance to the jaw and the elimination of posterior interferences (e.g., collisions) without any limitations due to the conditions of, malocclusion of, or even the presence or absence of the teeth to include anterior teeth. The AGP may be indexed and then attached to retentive pieces within the splint system, not directly to the teeth or arch. The AGP equipped splint may provide this guidance to the jaw with a minimal vertical dimension penalty when the jaw is in centric relation (CR) because the AGP may be placed anterior to and independent of teeth. The AGP equipped splint may provide unprecedented control of the anterior guidance and limitations of the jaw to the operator because the selection of guidance, or design of that guidance, by the dental professional is three dimensional and independent of teeth.

In some embodiments, the disclosed AGP may help patients avoid spending additional time in a dentist office to initially receive an AGP splint or to obtain a new AGP splint when the previous one becomes worn out or damaged. Embodiments of the disclosed methods may minimize the time and effort of both the patient and the dentist to get a new AGP splint specially designed for the patient. Using a virtual articulator and CAD-CAM technology combined with an AGP, a dental professional can provide to a patient an AGP splint that can be produced from an unprecedented wide range of three-dimensional guidance and limit parameters. Digital records made or traditional records converted to digital made from the patient can be analyzed and then taking advantage of the flexibility of the AGP, a plethora of design possibilities regarding guidance and limits for the mandible dependent upon the dental professional's goals for that patient can be realized. One could produce a superior, seamless AGP splint for the bruxism patient, a sophisticated TMD AGP splint produced with specific jaw repositioning and guidance limitations as proscribed by the dental professional, or a mandibular protrusive repositioning sleep apnea appliance. Embodiments of a method of automatically producing or reproducing a customized AGP equipped splint for a patient with or without a severe malocclusion is provided. The method of automatic producing or reproducing an AGP equipped splint may combine Virtual Articulation technology and/or CAD (Computer Aided Design)-CAM (Computer Aided Manufacturing) methods with the unique attributes of the AGP and special retentive piece technology. The method may enable a patient with or without a severe malocclusion and bruxism to receive a customized bruxism AGP equipped splint, a TMD patient with or without a severe malocclusion to receive a sophisticated TMD AGP splint produced with specific jaw repositioning and guidance limitations, or a sleep apnea patient to receive a mandibular protrusive repositioning sleep apnea appliance automatically without visiting the dental professional repeatedly.

The disclosed methods can be applied to a wide range of stock AGPs, and/or stock AGPs that are subsequently modified, and/or a custom designed AGP for a specific patient. The AGP could be any of a wide selection of size, shape or style to address a very wide range of problems and/or malocclusions. The maxillary component and/or the mandibular component of the AGP can be designed or modified to any of a wide selection of shape, size, or style either individually or as a group to achieve the effect the operator desires. For instance, a TMD therapist will have available an unprecedented range of options regarding both limits and guidance to the mandible. In contrast to other systems, the AGP can provide a wide range of three-dimensional anterior guidance, and limits to the mandible independent of the condition, position, presence or absence of teeth. Also, the position of the AGP (and therefore guidance and limits of the mandible) within the AGP splint system can be controlled to maximize or minimize different properties to include increase or decrease of the mechanical advantage over the muscles of mastication of the AGP splint. Considering the unprecedented three-dimensional selection and design potential of the AGP, and the extreme flexibility regarding the position of the AGP within the AGP splint system, the CAD-CAM AGP splint, the CAD-CAM TMD AGP splint, and CAD-CAM sleep apnea AGP splint are far superior to existing night guards, TMD appliance systems, or sleep apnea systems.

The foregoing summarizes only a few aspects of the presently disclosed subject matter and is not intended to be reflective of the full scope of the presently disclosed subject matter as claimed. Additional features and advantages of the presently disclosed subject matter are set forth in the following description, may be apparent from the description, or may be learned by practicing the presently disclosed subject matter. Moreover, both the foregoing summary and following detailed description are exemplary and explanatory and are intended to provide further explanation of the presently disclosed subject matter as claimed.

BRIEF DESCRIPTION OF THE DRAWINGS

FIG. 2-a is an enlarged cross-sectional view of a maxillary guidance component of an AGP along line A-A' in accordance with an exemplary embodiment.

FIG. 2-b is an enlarged cross-sectional view of a maxillary guidance component of an AGP along line B-B' in accordance with an exemplary embodiment.

FIG. 5-a is a perspective view of a special retentive piece to receive an AGP in accordance with an exemplary embodiment.

FIG. 5-b is a side view of a special retentive piece to receive an AGP in accordance with an exemplary embodiment.

FIG. 9 is a planar perspective view of a "canine guidance" AGP for a patient with bruxism in accordance with an exemplary embodiment.

FIG. 10 is a planar perspective view of a "group function" AGP for a patient with bruxism in accordance with an exemplary embodiment.

FIG. 11 is a planar perspective view of a "bilateral anterior repositioning" TMD AGP in accordance with an exemplary embodiment.

FIG. 11-a is a schematic drawing of indexing the mandible left laterally to the maxilla in accordance with an exemplary embodiment.

FIG. 11-b is a schematic drawing of indexing the mandible right laterally to the maxilla in accordance with an exemplary embodiment.

FIG. 12-a is a planar perspective view of a "unilateral anterior repositioning" TMD AGP for a patient who has a damaged disc within the right TMJ in accordance with an exemplary embodiment.

FIG. 13 is a planar perspective view of an "asymmetric TMD treatment" AGP for a patient who has a damaged structure on the right side of the mandible in accordance with an exemplary embodiment.

FIG. 13-a is a planar perspective view of an "asymmetric TMD treatment" AGP for a patient who has a damaged structure on the right side of the mandible in accordance with an exemplary embodiment.

FIG. 24-a is a conceptual drawing of the relative position of the maxillary and mandibular retentive pieces and virtual point(s) along the transverse plane for a bruxism or TMD patient without a severe malocclusion, Class I, in accordance with an exemplary embodiment.

FIG. 24-b is a conceptual drawing of the relative position of the maxillary and mandibular retentive pieces and virtual point(s) along the transverse plane for a bruxism or TMD patient with a Class II malocclusion, in accordance with an exemplary embodiment.

FIG. 24-c is a conceptual drawing of the relative position of the maxillary and mandibular retentive pieces and virtual point(s) along the transverse plane for a bruxism or TMD patient with a Class III malocclusion, in accordance with an exemplary embodiment.

DETAILED DESCRIPTION

Figure 1:
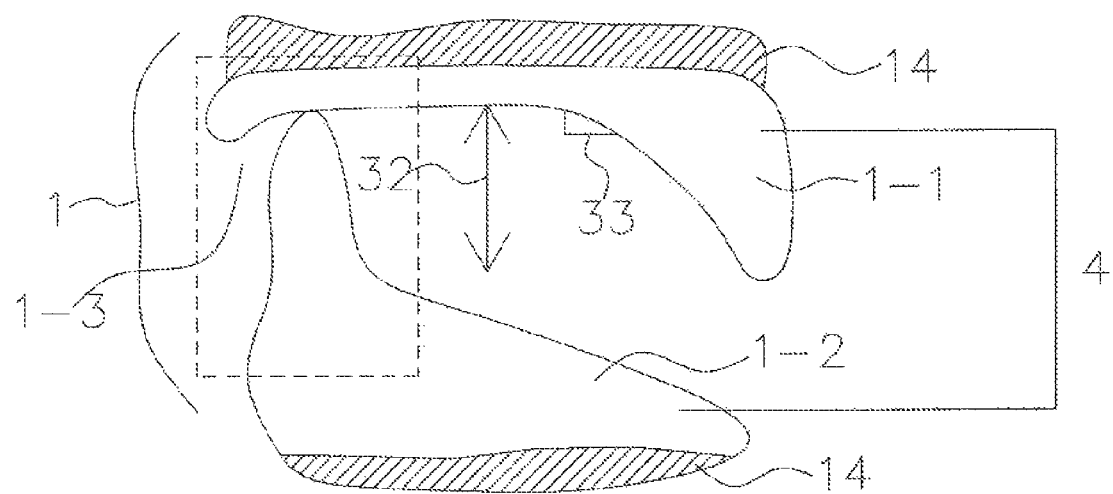
FIG. 1 is a side view of an AGP for the amelioration of the damage and pain caused by bruxism in accordance with an exemplary embodiment.

The various embodiments of the presently disclosed subject matter are described with specificity to meet statutory requirements. However, the description itself is not intended to limit the scope of this patent. Rather, it has been contemplated that the claimed subject matter might also be embodied in other ways, to include different steps or elements similar to the ones described in this document, in conjunction with other present or future technologies.

It should also be noted that, as used in the specification and the appended claims, the singular forms "a," "an" and "the" include plural references unless the context clearly dictates otherwise. References to a composition containing "a" constituent is intended to include other constituents in addition to the one named. Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

Further, used herein the terms "dentist," "dental professional," "operator," "clinician," and the like shall be interchangeable to refer to a person providing dental care or treating using the disclosed systems, methods, or devices.

Embodiments discussed herein refer to placing a patient's jaws in a predetermined index position, such as centric relation (CR). It is to be understood that, while CR is a relaxed position for many bruxism patients, predetermined index position may also refer to other relaxed positions such as a position chosen and/or refined by muscle testing or a relaxed position chosen by the dental professional using 3D radiography, MRI, sonography, or other imaging. Further, it should be understood that predetermined index position may also refer to a position that is not necessarily relaxed but is chosen by the dental professional for its therapeutic value, including, but not limited to, a position selected by the dental professional based on the damage or disease profile of the patient, a position selected by the dental professional that adequately moves the mandible protrusively to address sleep apnea, and a therapeutic position selected by the dental professional using 3D radiography, MRI, sonography, or other imaging. The disclosed systems, methods, and devices may be configured to place the patient's jaws in any predetermined index position.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required. The components described hereinafter as making up various elements of the invention are intended to be illustrative and not restrictive. Many suitable components that would perform the same or similar functions as the components described herein are intended to be embraced within the scope of the invention. Such other components not described herein can include, but are not limited to, for example, similar components that are developed after development of the presently disclosed subject matter.

To facilitate an understanding of the principles and features of the invention, various illustrative embodiments are explained below. In particular, the presently disclosed subject matter is described in the context of being an Anterior Guidance Package (AGP) for treating a patient with bruxism.

In one aspect, a method for preparing an AGP equipped splint for a patient with one or more of bruxism, temporomandibular disorder (TMD), and sleep apnea is disclosed. The method may include obtaining patient data comprising three dimensional arch data associated with the patient. After obtaining the patient data, one or more digital models may be generated on one or more processors based on the patient data. The one or more digital models may include virtual maxillary and mandibular arches. The method may also include determining an index position for the patient. The virtual maxillary and mandibular arches may be positioned in the index position. Further, the method may include separating the virtual maxillary and mandibular arches based on an arc of closure associated with the patient to provide a threshold clearance. A virtual maxillary retentive piece may be applied to the virtual maxillary arch and a virtual mandibular retentive piece may be applied to the virtual mandibular arch.

One or more virtual points may be generated based on one or more of the index position and one of the retentive pieces. A virtual AGP package may be positioned in virtual space based on the one or more virtual points. For example, in one embodiment, the virtual AGP package may be positioned based on a single virtual point without the need for orientation, alignment, or position data of either virtual retentive piece. In this fashion, the virtual AGP may be a stock AGP that is customized after it is positioned or a customized AGP.

In another embodiment, the virtual AGP may be positioned based on a single virtual point along with one or more of orientation, alignment, and position data of at least one of the virtual retentive pieces. The orientation, alignment, and/or position data of the virtual retentive piece(s) provide context for relative positioning of the virtual point in virtual three dimensional space. In this fashion, the virtual AGP may be a stock AGP that does not require customization, which may decrease the time and cost associated with producing the AGP for a particular patient. In yet another embodiment, the virtual AGP may be positioned based on three or more virtual points, which collectively provide context for relative positioning of the AGP in three dimensions without requiring orientation, alignment, or position date of the virtual retentive pieces. In this fashion, the virtual AGP may be a stock AGP that does not require customization, which may decrease the time and cost associated with producing the AGP for a particular patient.

The AGP package may include a virtual maxillary guidance component and a virtual mandibular guidance component. After positioning the AGP package in virtual space, the virtual maxillary guidance component may be connected to the virtual maxillary retentive piece to form a first part of a virtual AGP equipped splint. Similarly, the virtual mandibular guidance component may be connected to the virtual mandibular retentive piece to form a second part of the virtual AGP equipped splint. AGP equipped splint production data based on the first and second parts of the virtual AGP equipped splint can then be transmitted. For example, the AGP equipped splint production data may be transmitted to a manufacturer equipped with one or more of CAM, CNC technology, and an in-office 3D printer.

In some embodiments, at least one of the mandibular guidance component and the maxillary guidance component may be positioned about an anterior aspect of the mandibular retentive piece and the maxillary retentive piece, respectively.

In other embodiments, generating the one or more virtual points may include positioning the one or more virtual points to provide a clearance of at least 1 mm between the virtual maxillary retentive piece and the virtual mandibular retentive piece of the virtual AGP equipped splint. In some embodiments, the method may also include virtually simulating movement of the virtual AGP equipped splint. For example, in some embodiments, movement of a stock AGP may be simulated to help determine which stock AGP is most appropriate for a particular patient and/or whether customization of the selected stock AGP is required. If an AGP is customized, the movement of the customized AGP may be simulated to confirm that it will operate as desired and, if necessary, indicate a need for further customization prior to producing a physical AGP splint. This can help decrease time and cost associated with producing the AGP for a particular patient, as it avoids multiple iterations of testing movement of a physical AGP splint in a patient's mouth. It may also provide increased accuracy as the dental practitioner may have improved visibility in the virtual model compared to a physical model placed within a patient's mouth.

In some embodiments, generating the one or more virtual points may include positioning two virtual points that are bilaterally equidistant from a reference plane. The reference plane may be perpendicular to a mid-sagittal plane and positioned about 6 mm from a most anterior aspect of one of the virtual retentive pieces (e.g., the maxillary retentive piece) along an occlusal plane mid-sagittally. Further, connecting one of the virtual guidance components (e.g., the maxillary retentive component) to one of the virtual retentive pieces (e.g., the maxillary retentive piece) may be based on the two virtual points and an orientation, alignment, and/or position of the other virtual retentive piece (e.g., the mandibular retentive piece).

In other embodiments, generating the one or more virtual points may include positioning one virtual point proximate a reference plane positioned about 6 mm from a most anterior aspect of one of the virtual retentive pieces (e.g., the maxillary retentive piece) along an occlusal plane mid-sagittally. The reference plane may be perpendicular to a mid-sagittal plane. Further, connecting one of the virtual guidance components (e.g., the maxillary retentive piece) to the other virtual retentive piece (e.g., the maxillary retentive piece) may be based on the virtual point and an orientation, alignment, and/or position of the other virtual retentive piece (e.g., the mandibular retentive piece).

In some embodiments, obtaining patient data may further include obtaining temporomandibular joint (TMJ) data associated with left and right TMJs of the patient. Generating the one or more virtual points may include positioning one virtual point proximate a reference plane positioned about 6 mm from a most anterior aspect of one of the maxillary retentive pieces (e.g., the maxillary retentive piece) along an occlusal plane mid-sagittally. The reference plane may be perpendicular to a mid-sagittal plane. Positioning the virtual AGP package in virtual space may include positioning the virtual AGP package in an AGP index position such that the mandible is adjusted outside of centric relation based on the virtual point. By adjusting the mandible, the AGP index position may be configured to protrusively, laterally, and vertically recapture the left and right TMJ discs. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

In some embodiments, one of the left and right TMJ condyles must travel further than the other TMJ condyle for the recapture of its relative disc.

In other embodiments, obtaining patient data may further include obtaining TMJ data associated with left and right TMJs of the patient, one of the left and right TMJ discs being anteriorly displaced/damaged. Generating the one or more virtual points may include asymmetrically positioning two virtual points in relation to a mid-sagittal plane proximate a plane perpendicular to the mid-sagittal plane that is positioned about 6 mm from a most anterior aspect of one of the virtual retentive pieces (e.g., the maxillary retentive piece) along an occlusal plane mid-sagittally. Positioning the virtual AGP package in virtual space may include positioning the virtual AGP package in an AGP index position such that the mandible is configured to recapture the damaged TMJ disc based on the two virtual points. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

In some embodiments, the AGP index position may adjust the mandible such that it is configured to recapture the damaged TMJ disc while allowing the other TMJ disc to remain in a centric relation position.

In other embodiments, obtaining patient data may further include obtaining damaged structure data associated with the patient. Generating the one or more virtual points may include positioning one virtual point proximate a midsagittal plane and proximate a plane perpendicular to the mid-sagittal plane that is positioned about 6 mm anterior to a most anterior aspect of one of the virtual retentive pieces (e.g., the maxillary retentive piece) along an occlusal plane mid-sagittally. Positioning the virtual AGP package in virtual space may include positioning the virtual AGP package in an AGP index position configured to treat one or more of a mandible, a TMJ, and a stomatognathic condition of the patient based on the damaged structure data. In some embodiments, the AGP index position may be configured to adjust the mandible out of centric relation. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

In some embodiments, the damaged structure data may indicate that one of a left side or a right side of a mandible of the patient is damaged. Further, positioning the virtual AGP package in virtual space may include protrusively moving the damaged side of the mandible to advance a condyle of the damaged side out of a centric relation position while laterally moving the undamaged side of the mandible to keep a condyle of the undamaged side in the centric relation position.

In another aspect, a system for preparing an AGP equipped splint for a patient with one or more of bruxism, TMD, and sleep apnea is disclosed. In some embodiments, the system may include a data module configured to obtain patient data comprising three dimensional arch data associated with the patient. The system may also include a modeling module configured to generate one or more digital models on one or more processors based on the patient data, the one or more digital models comprising virtual maxillary and mandibular arches. The system may further include a determination module configured to determine an index position for the patient. An arch positioning module of the system may be configured to position the virtual maxillary and mandibular arches in the index position. The system may include a separation module configured to separate the virtual maxillary and mandibular arches based on an arc of closure associated with the patient to provide a threshold clearance. The system may further include an application module configured to apply a virtual maxillary retentive piece to the virtual maxillary arch and a virtual mandibular retentive piece to the virtual mandibular arch. A generation module of the system may be configured to generate one or more virtual points based on the index position. An AGP positioning module of the system may be configured to position a virtual AGP package in virtual space based on the one or more virtual points, the AGP package comprising a virtual maxillary guidance component and a virtual mandibular guidance component. The system may include a maxillary connection module configured to connect the virtual maxillary guidance component to the virtual maxillary retentive piece to form a first part of a virtual AGP equipped splint. The system may also include a mandibular connection module configured to connect the virtual mandibular guidance component to the virtual mandibular retentive piece to form a second part of the virtual AGP equipped splint. Further, the system may include a transmission module configured to transmit AGP equipped splint production data based on the first and second parts of the virtual AGP equipped splint.

In some embodiments, the AGP positioning module may be further configured to position at least one of the mandibular guidance component and the maxillary guidance component about an anterior aspect of the mandibular retentive piece and the maxillary retentive piece, respectively. Further, the generation module may be further configured to position the one or more virtual points to provide a clearance of at least 1 mm between the virtual maxillary retentive piece and the virtual mandibular retentive piece.

In yet another aspect, a non-transitory computer-readable storage medium having stored computer-executable instructions that, when executed by one or more processors, cause a computer to perform functions for preparing an AGP equipped splint is disclosed. In some embodiments, the instructions may include obtaining patient data comprising three dimensional arch data associated with the patient. The instructions may also include generating one or more digital models on one or more processors based on the patient data, the one or more digital models comprising virtual maxillary and mandibular arches. The instructions may further include determining an index position for the patient. The virtual maxillary and mandibular arches may be positioned in the index position according to the instructions. The virtual maxillary and mandibular arches may be separated based on an arc of closure associated with the patient to provide a threshold clearance. The instructions may include applying a virtual maxillary retentive piece to the virtual maxillary arch and a virtual mandibular retentive piece to the virtual mandibular arch. The instructions may also include generating one or more virtual points based on the index position. The instructions may further include positioning a virtual AGP package in virtual space based on the one or more virtual points. The AGP package may include a virtual maxillary guidance component and a virtual mandibular guidance component. The instructions may include connecting the virtual maxillary guidance component to the virtual maxillary retentive piece to form a first part of a virtual AGP equipped splint. Similarly, the virtual mandibular guidance component may be connected to the virtual mandibular retentive piece to form a second part of the virtual AGP equipped splint. Further, the instructions may include transmitting AGP equipped splint production data based on the first and second parts of the virtual AGP equipped splint.

In some embodiments, generating the one or more virtual points may include positioning two virtual points bilaterally equidistant from a reference plane. The reference plane may be perpendicular to a mid-sagittal plane and positioned about 6 mm from a most anterior aspect of one of the virtual retentive pieces (e.g., the maxillary retentive piece) along an occlusal plane mid-sagittally. Further, connecting one of the virtual guidance components (e.g., the maxillary retentive component) to its respective virtual retentive piece (e.g., the maxillary retentive piece) may be based on the two virtual points and an orientation, alignment, and/or position of the other virtual retentive piece (e.g., the mandibular retentive piece).

In other embodiments, generating the one or more virtual points may include positioning one virtual point proximate a reference plane positioned about 6 mm from a most anterior aspect of one of the virtual retentive pieces (e.g., the maxillary retentive piece) along an occlusal plane mid-sagittally. The reference plane may be perpendicular to the mid-sagittal plane. Further, connecting the virtual maxillary guidance component to one of the virtual retentive pieces (e.g., the maxillary retentive piece) may be based on the virtual point and an orientation, alignment, and/or position of the other virtual retentive piece (e.g., the mandibular retentive piece).

In further embodiments, obtaining patient data may include obtaining TMJ data associated with left and right TMJs of the patient. Generating the one or more virtual points may include positioning one virtual point proximate a reference plane positioned about 6 mm from a most anterior aspect of one of the virtual retentive pieces (e.g., the maxillary retentive piece) along an occlusal plane mid-sagittally. The reference plane may be perpendicular to the mid-sagittal plane. Positioning the virtual AGP package in virtual space may include positioning the virtual AGP package in an AGP index position such that the mandible is adjusted outside of centric relation based on the virtual point. By adjusting the mandible, the AGP index position may be configured to protrusively, laterally, and vertically recapture the left and right TMJ discs. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

In some embodiments, obtaining patient data may further include obtaining TMJ data associated with left and right TMJs of the patient, one of the left and right TMJ discs being anteriorly displaced and/or damaged. Generating the one or more virtual points may include asymmetrically positioning two virtual points in relation to a mid-sagittal plane proximate a reference plane. The reference plane may be perpendicular to the mid-sagittal plane and positioned about 6 mm from a most anterior aspect of one of the virtual retentive pieces (e.g., the maxillary retentive piece) along an occlusal plane mid-sagittally. Positioning the virtual AGP package in virtual space may include positioning the virtual AGP package in an AGP index position such that the mandible is configured to recapture the damaged TMJ disc based on the two virtual points. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

In other embodiments, obtaining patient data may further include obtaining damaged structure data associated with the patient. Generating the one or more virtual points may include positioning one virtual point proximate a mid-sagittal plane and proximate a plane perpendicular to the mid-sagittal plane that is positioned about 6 mm anterior to a most anterior aspect of one of the virtual retentive pieces (e.g., the maxillary retentive piece) along an occlusal plane mid-sagittally. Positioning the virtual AGP package in virtual space may include positioning, based on the virtual point, the virtual AGP package in an AGP index position configured to treat one or more of a mandible, a TMJ, and a stomatognathic condition of the patient based on the damaged structure data. In some embodiments, the AGP index position may be configured to adjust the mandible out of centric relation. Further, connecting one of the virtual guidance components (e.g., the maxillary retentive component) to its respective virtual retentive piece (e.g., the maxillary retentive piece) may be based on the AGP index position and an orientation, alignment, and/or position of the other virtual retentive piece (e.g., the mandibular retentive piece).

FIG. 1 shows an exemplary AGP kit 1 for the amelioration of damage and pain caused by bruxism. The AGP kit 1 could be delivered from the manufacturer, as shown in FIG. 1, or the AGP may be already attached to a retentive piece for one arch (e.g., the maxillary or mandibular arch) and then indexed onto a retentive piece molded to the other arch. In some embodiments, the AGP kit 1 may be indexed by a dental professional onto a shelf or shelves of the special retentive piece or pieces. The AGP kit 1 may include a maxillary guidance component 1-1, a mandibular guidance component 1-2, and a holder 1-3 that temporarily holds the two components 1-1 and 1-2 together at a desired position (e.g., centric relation). When the holder 1-3 is removed from the AGP kit 1, the functional parts may be collectively referred to as an AGP 4.

In some embodiments, steepness 33 and depth 32 of the areas of lateral and protrusive guidance on the maxillary component 1-1 of the AGP 4 can be controlled or modified to provide anterior stops and guidance to the mandible for a very wide range of treatment goals that the operator may have in mind.

Figure 2:
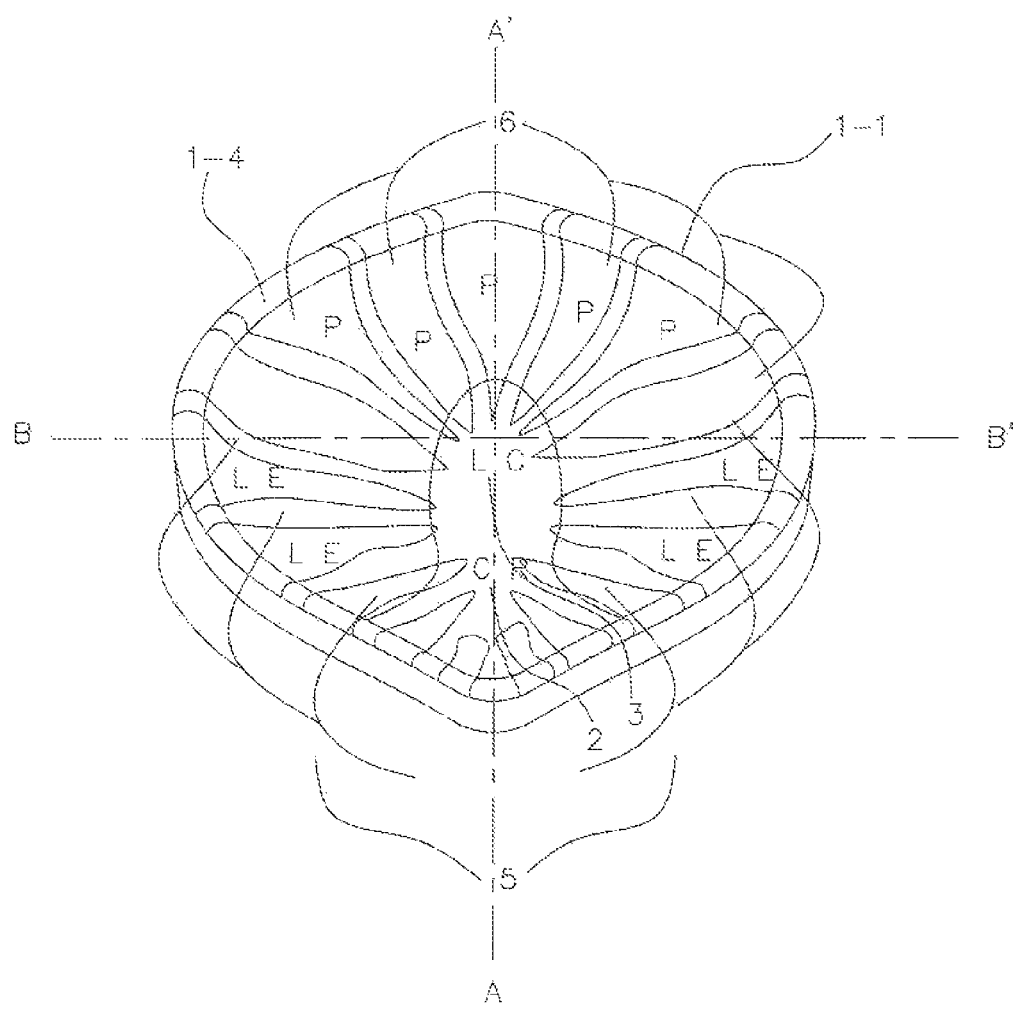
FIG. 2 is an overhead view of the internal topography of a maxillary guidance component of an AGP in accordance with an exemplary embodiment.

FIG. 2 shows the internal topography of the maxillary guidance component 1-1 of an exemplary AGP, including a specific guidance of a CR stop 2, a long centric (LC) area 3, a lateral excursion (LE) guidance 5, and a protrusive (P) guidance 6. As shown in FIGS. 2, 2-a and 2-b, the maxillary guidance component 1-1 of the AGP may have a flat area for a stable CR stop 2 extended into a further area of flat for the LC position 3 of the mandible extending laterally and anteriorly into blended inclines of a concave inferiorly oriented shape for LE guidance 5 (FIG. 2-b) and protrusive (P) excursion guidance 6 (FIG. 2-a) to provide ideal anterior guidance to the patient's mandible by the mandibular guidance component 1-2 against these features of the maxillary guidance component 1-1 to minimize muscular force and avoid all posterior interferences. This feature of appropriate anterior guidance, which moves the mandible downward (inferiorly) in its excursions, may allow for a night guard of significantly less vertical dimension 16 at rest than other designs, much like an ideal occlusion would. It is contemplated that the maxillary guidance component 1-1 may take on any size based on a patient's range of motion.

Figure 3:
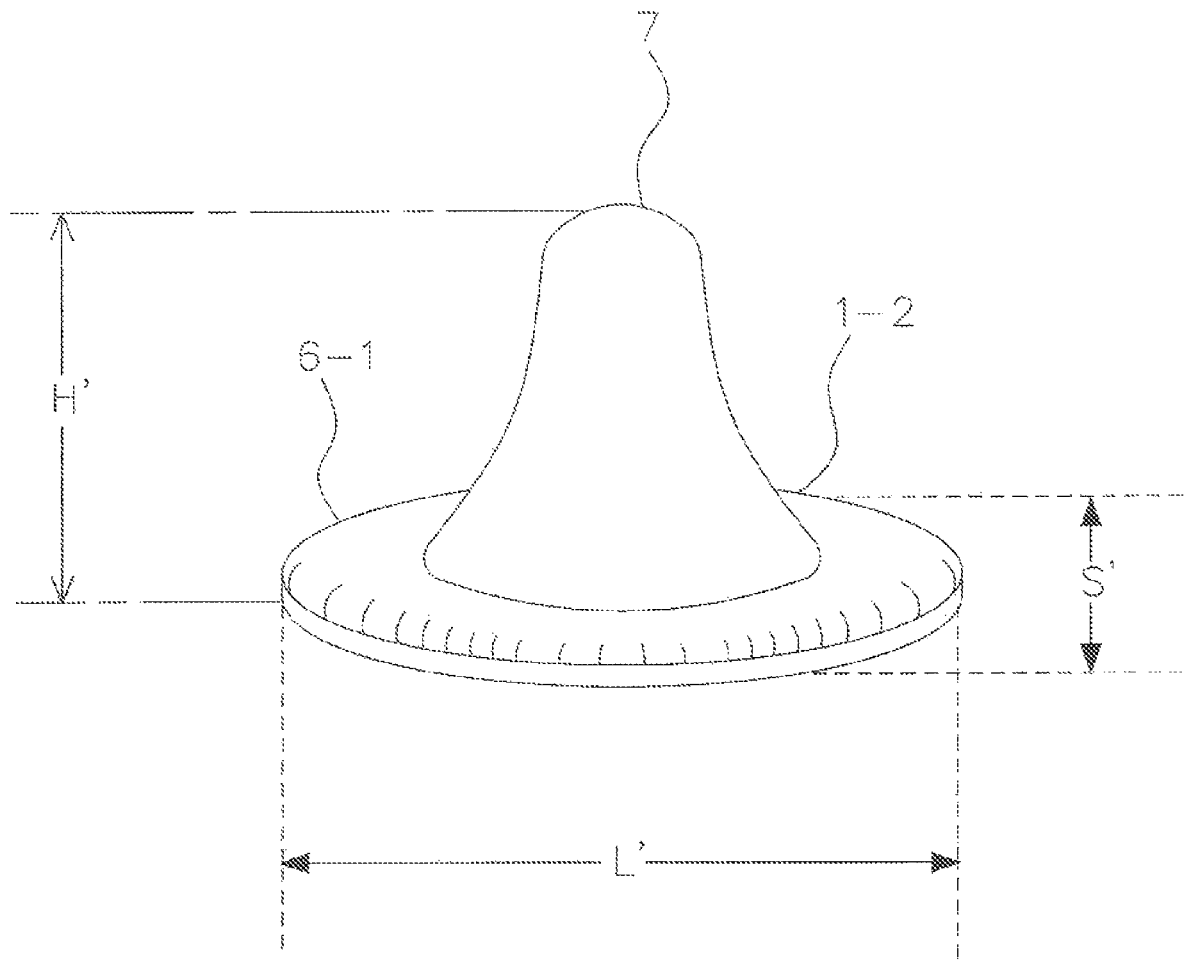
FIG. 3 is a perspective view of a mandibular guidance component of an AGP in accordance with an exemplary embodiment.

FIG. 3 shows the mandibular guidance component 1-2 of the AGP kit 1. A base 6-1 of the mandibular guidance component 1-2 may have a superellipse or square ovoid shape and the same dimension as the maxillary guidance component 1-1, as shown in FIG. 2.

In some embodiments, the length of the long axis L' of the oval shaped mandibular guidance component 1-2 may be, including but not limited to, between 15 to 35 mm. The length of the short axis (S') of the oval shaped mandibular guidance component 1-2 may be, including but not limited to, between 8 to 20 mm.

A smooth rounded protrusion 7 may be developed on one surface of the square ovoid shaped mandibular guidance component 1-2. A tip of the protrusion 7 may become engaged in the flat to concave inner surface of the maxillary guidance component 1-1 and guide and limit the movement of a patient's mandible. In some embodiments, the height H' of the smooth protrusion may be, including but not limited to, between 1 to 6 mm. For example, in one embodiment, the height H' may be about 5 mm. As with any AGP 4 construction, the steepness and depth of the protrusion 7 of the mandibular component 1-2 of the AGP 4 can be controlled to provide anterior stops and guidance to the mandible for a wide range of treatment goals the dental professional may have in mind.

Figure 4:
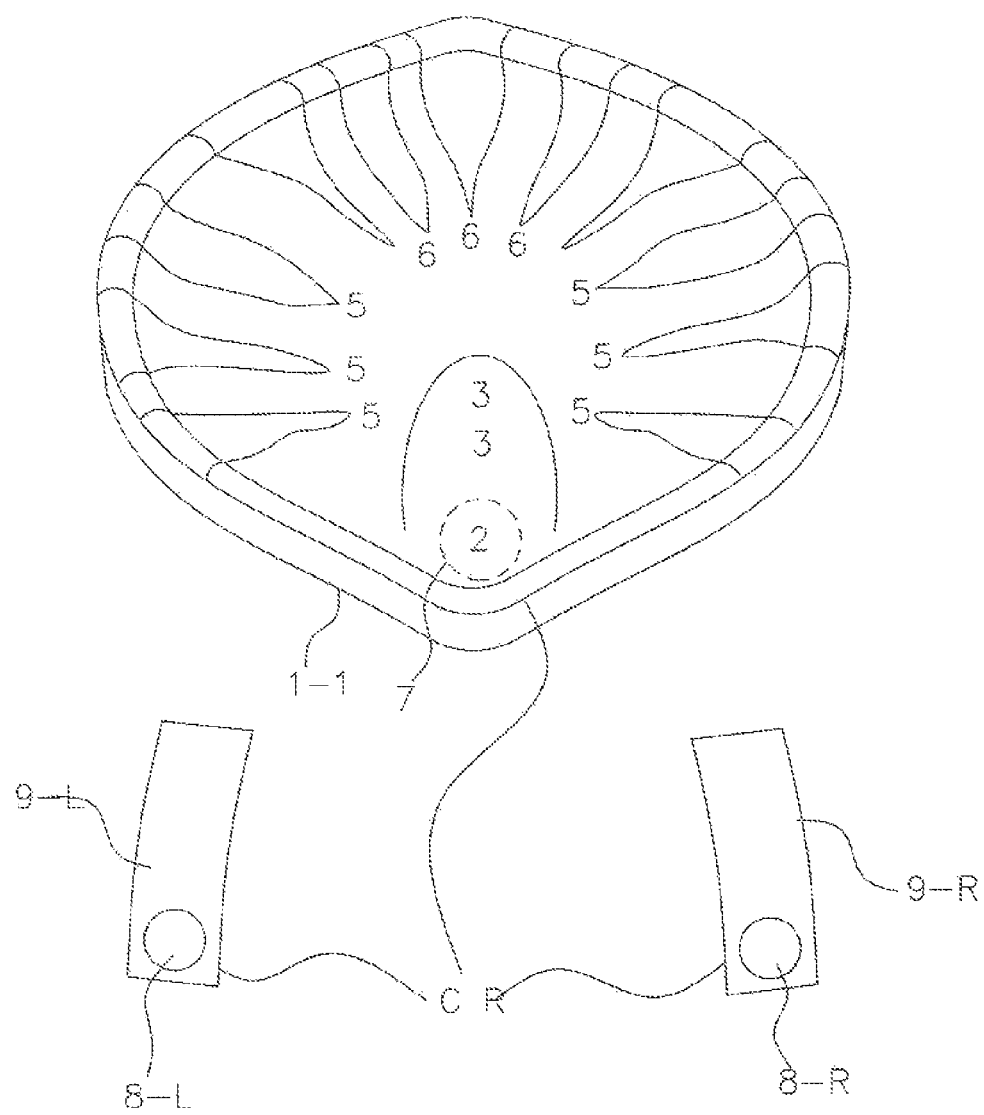
FIG. 4 is a transparent view of an AGP positioned at centric relation position in accordance with an exemplary embodiment.

FIG. 4 shows the AGP correlating with the CR position of the Temporomandibular Joints (TMJs) 9-R and 9-L, which represent the right and left TMJs, respectively. In some embodiments, as shown, the AGP may replicate ideal anterior guidance. In the context of bruxism, for example, ideal anterior guidance would provide the patient with immediate elimination of all posterior interferences by the anterior teeth in any excursion of the mandible. A reference point 2 represents where the protrusion 7 of the mandibular guidance component 1-2 sits at rest in the maxillary guidance component 1-1 when right and left condyles 8-R and 8-L of the TMJs 9-R and 9-L of the mandible are in their CR position. As a patient functions or bruxes his mandible, the mandibular guidance component 1-2 may provide ideal anterior guidance for the mandible by means of the mandibular guidance component 1-2 functioning against the maxillary guidance component 1-1 in the position of CR 2, LC 3, LE 5, and P guidance 6. In some embodiments, the AGP may provide ideal anterior guidance without regard to the position of teeth, the condition of teeth or missing teeth. For example, the AGP may be indexed and attached to retentive pieces within the splint system rather than being directly to the teeth or arch.

FIGS. 5-a and 5-b show a special retentive piece 10, which may be similar to the special retentive pieces discussed in U.S. Patent App. Pub. No. 2014/0238415. The special retentive piece 10 may facilitate the application of the AGP to a broad spectrum of patients with a wide range of maladies, occlusions and malocclusions. The special retentive piece 10 for the maxilla or mandible may have a shelf 11 to receive the appropriate component of the AGP. The shelf 11 may anteriorly extend beyond the special retentive piece 10. In some embodiments, the shelf 11 may be positioned at the most anterior aspect of the special retentive piece 10. Vertical position of the shelf 11 may vary from the open side 10-O of the groove 11-1 that molds to the teeth and arch down to the closed side 10-C of the groove of the special retentive piece 10. The shelf 11 may be connectable to the special retentive piece 10 in a variety of ways. For example, in one embodiment, the shelf 11 may be inserted into the groove 11-1, which is vertically developed on the anterior surface of the special retentive piece 10. In other embodiments, the shelf 11 may be fastened, snapped, glued, or otherwise attached via mechanical or chemical means.

With the special retentive piece 10, the AGP equipped special splint may be suitable for patients who have different types of occlusions and malocclusions and have bruxism at the same time, or a TMJ disorder, other stomagnathic damage, or a sleep apnea disorder. The AGP splint may be produced with specific jaw repositioning and guidance limitations as proscribed by the dental professional.

Figure 6:
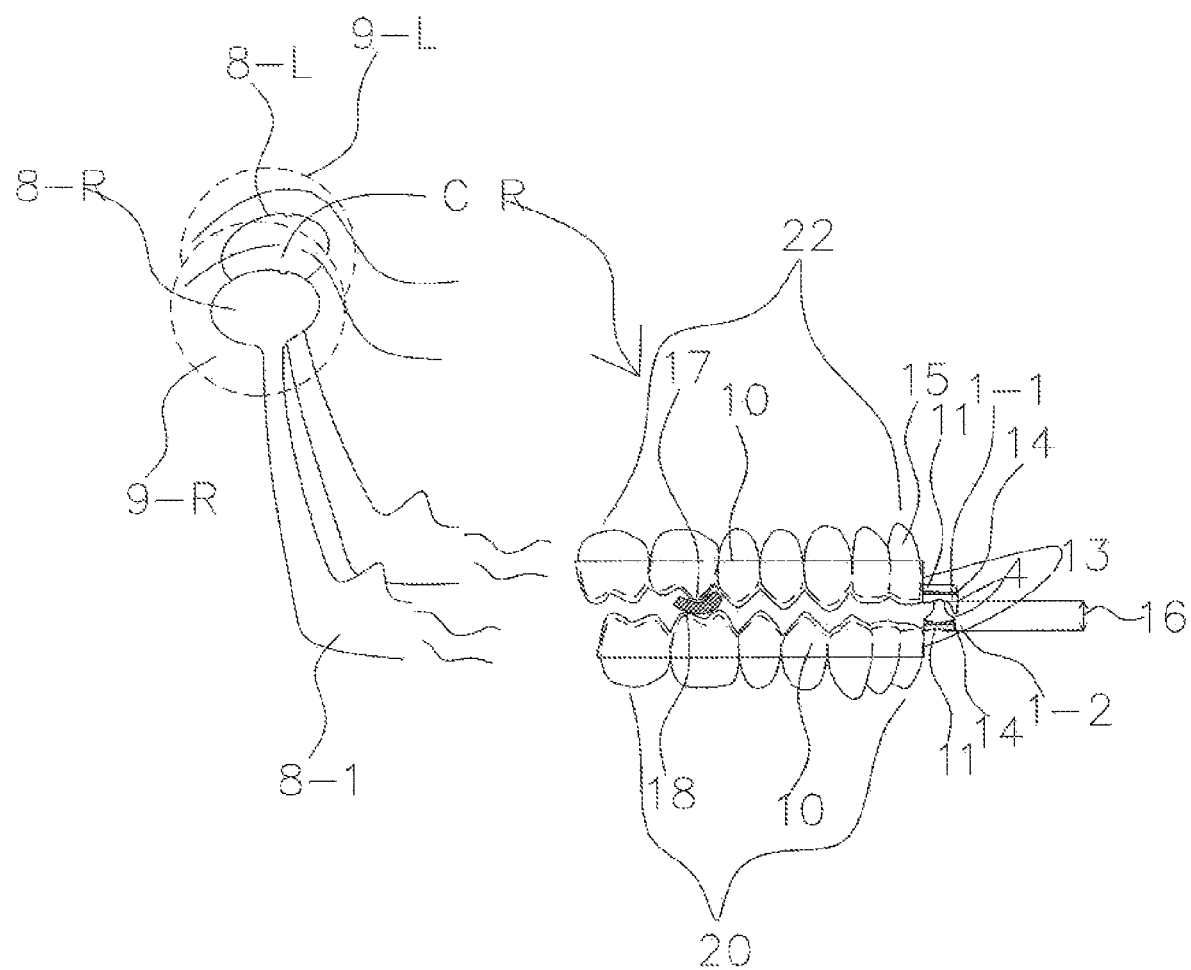
FIG. 6 is a schematic drawing showing an exemplary method for using special retentive pieces as platforms for an AGP for both the maxillary and mandibular arches.

FIG. 6 shows an exemplary application of the special retentive piece 10 for both the maxillary and mandibular retentive pieces to enable the AGP 4 to be placed anterior to the anterior teeth to comprise a splint 13 that is a combination of the special retentive pieces 10 and an AGP 4. In some embodiments, the AGP 4 may be attached to the shelf 11 via glue 14. In other embodiments, the AGP 4 may be attached to the shelf 11 via any chemical or mechanical means. As shown, the space between the retentive pieces 10 for the mandible and maxilla is exaggerated to help visualize a first contact point 17 and relative interferences (or collisions) of cusps of the teeth. The first contact point 17 is the first point of contact between maxillary and mandibular teeth as the patient's jaw is closed into the index position by the dental professional.

In some embodiments, the AGP 4 may provide anterior guidance that is not dependent upon teeth. For example, the AGP 4, and therefore the anterior guidance, may be placed anterior to the most anterior teeth (15 and 21). This configuration may increase the mechanical advantage of the AGP 4 over the muscles of mastication in excursions.

Further, by placing the AGP 4 further anterior than the actual position of the maxillary anterior teeth and/or the mandibular anterior teeth 15 and/or 21, the AGP 4 may provide anterior guidance with minimal vertical dimension 16 increase when the patient's mandible is at rest in CR (or another predetermined index position). As the AGP 4 can be positioned anterior to both the maxillary anterior teeth 15 and the mandibular anterior teeth 21, the AGP 4 can provide three-dimensional anterior guidance displacing the mandible inferiorly in excursions to help eliminate interferences (e.g., collisions). Further, as the AGP 4 and special retentive pieces 10 minimize the vertical dimension 16 when the patient is in the predetermined index position, the patient's acceptance and comfort may increase dramatically. Some exemplary methods for finding the first contact 17 and the use of a spacer 18 (e.g., a 1 mm sticky but removable spacer) to identify and create appropriate space in CR (or the predetermined index position) are described in detail in U.S. Patent App. Pub. No. 2014/0060549.

Figure 7:
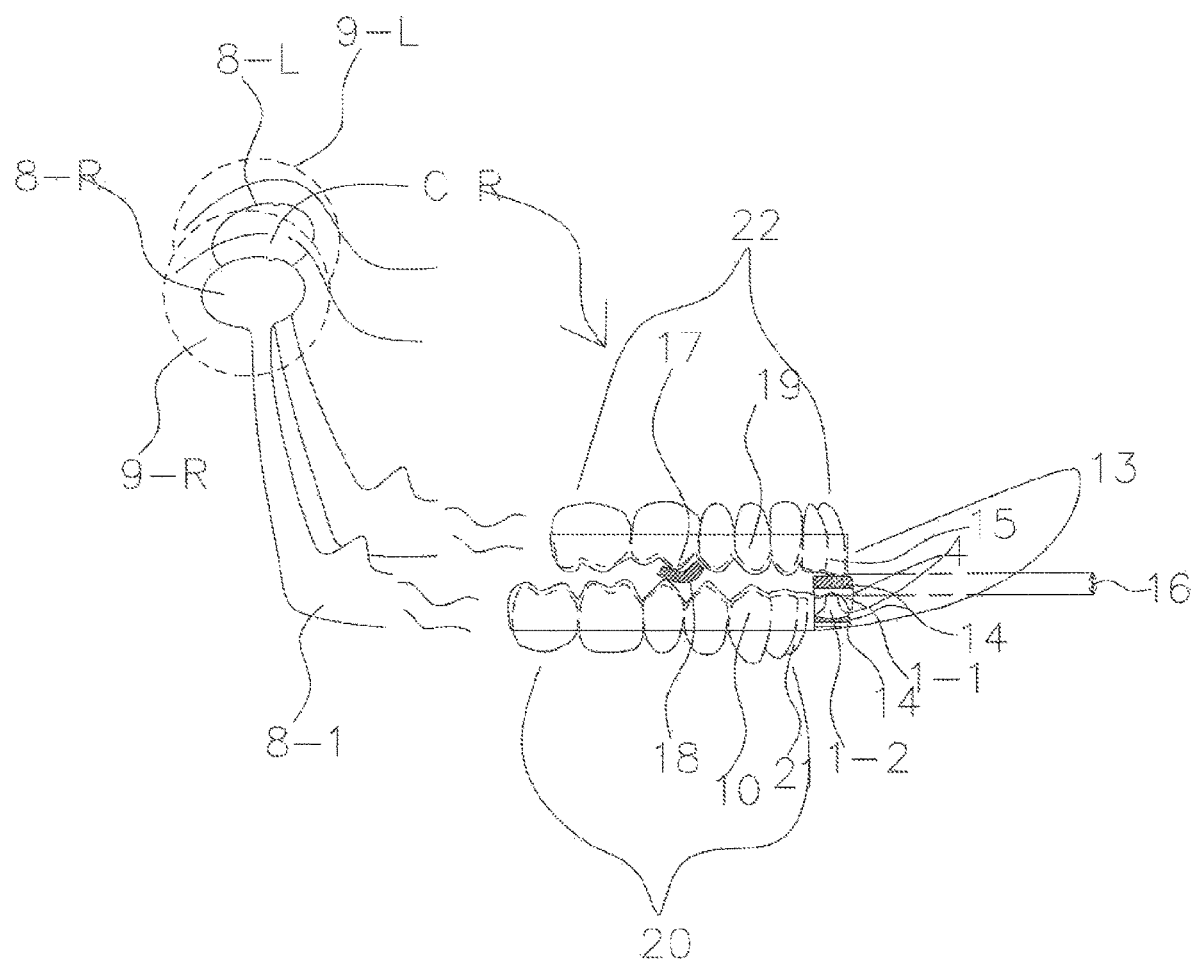
FIG. 7 is a schematic drawing showing an exemplary method for using a special retentive piece and a regular retentive piece for a patient with a significant Class II malocclusion.
Figure 8:
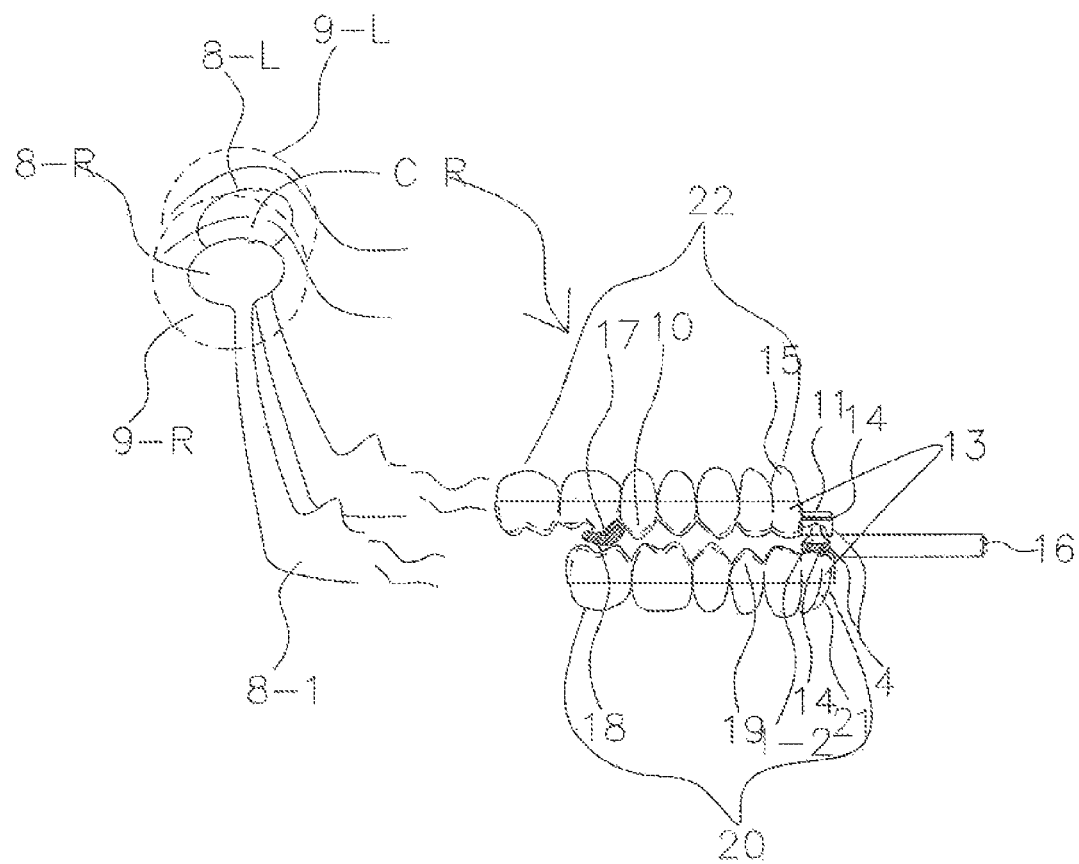
FIG. 8 is a schematic drawing showing an exemplary method for using a special retentive piece and a regular retentive piece for a patient with a significant Class III malocclusion.

FIGS. 7 and 8 illustrate an exemplary use of one special retentive piece 10 and one regular retentive piece 19 for a patient who presents with a significant Class II malocclusion and with a significant Class III malocclusion, respectively.

In FIG. 7, the special retentive piece 10 is placed on the patient's retrognathic mandibular arch 20, and the regular retentive piece 19 is placed on the patient's maxillary arch 22 to treat bruxism of a patient with a significant Class II malocclusion. The special retentive piece 10 may allow for placement of the AGP 4, and therefore anterior guidance, anterior to the anatomical position of the mandibular front teeth 21. As shown, the vertical dimension 16 of the AGP splint 13 at rest may be minimized by combining the special retentive piece 10 and the regular retentive piece 19. In this configuration, a patient suffering significant Class II malocclusion and bruxism may have a night guard with much greater mechanical advantage over the muscles of mastication in excursions from CR and may be more comfortable due to minimal vertical dimension 16 increase at rest in CR. Also, a dental professional can provide a proper night guard for a patient who has these problems with much less effort.

In FIG. 8, the special retentive piece 10 is placed on the patient's maxillary arch 22, and the regular retentive piece 19 is placed on the patient's mandibular arch 20 to treat bruxism of a patient with a significant Class III malocclusion. The special retentive piece 10 may allow for placement of the AGP 4 anterior to the anatomical limitation of the maxillary front teeth 15. As shown, the vertical dimension 16 for a patient at rest using the AGP splint 13 may be minimized by combining the special retentive piece 10 and the regular retentive piece 19. In this configuration, a patient suffering significant Class III malocclusion and bruxism may have a night guard with much greater mechanical advantage over the muscles of mastication in excursions from CR, and may be more comfortable due to minimal vertical dimension 16 increase at rest in CR. Also, a dental professional can provide a proper night guard for a patient who has these problems with much less effort.

In some embodiments, the AGP 4 may be attached to the splints 10 and 19 upside-down and with proper rotation of the AGP 4. In other words, the maxillary aspect of the AGP 1-1 may be attached to a mandibular retentive piece and the mandibular aspect of the AGP 1-2 may be attached to a maxillary retentive piece, such that the AGP 4 can be used interchangeably with the maxillary and mandibular retentive pieces.

The AGP 4 may be configured to provide guidance and limits to the front end of the mandible three-dimensionally independent of malocclusion or condition of the patients' teeth. The AGP 4 may be available in different stock configurations, which could be modified by the dental professional, and in the context of a CAD-CAM AGP, the AGP 4 could be designed by the dental professional from a template based on diagnostic information and a damage profile of a particular patient. This customizable AGP 4 may offer a wide range of solutions for treating patients with bruxism and various occlusions and malocclusions. The AGP 4 may provide the dental professional with a broad spectrum of three-dimensional patterning to guide the patient's mandible to the selected destination by a wide range of three-dimensional routes.

Real human malocclusions can be complex, and are generally classified as Class I, II, or III. These occlusions and malocclusions can be further complicated by anterior and posterior crossbites, overjet, deep bite, open bite and other modifiers and combinations thereof.

In regard to bruxism splints, an AGP equipped splint may be configured to treat a plethora of different occlusions and malocclusions, provide anterior guidance to neutralize posterior interferences to allow the patient's mandible to function in the best stress bearing position of CR even under the stress of bruxism, eliminate engrams of interferences to decrease inappropriate muscle activity and spasticity, give protection to the teeth and the TMJ, the reduction of myo-facial pain syndrome, and the reduction of migraine headaches.

FIG. 9 shows another exemplary design of a bruxism AGP, a "canine guidance" AGP 4-C. In some embodiments, there may be two protrusions 7a and 7b on the mandibular component 1-2-C of the AGP 4-C that are spaced laterally apart in a way that would mimic ideal human "canine" anterior guidance. In other words, the mandibular component 1-2-C of the AGP 4-C, which mimics ideal lower canines, may function against the maxillary component 1-1-C of the AGP 4-C, which mimics ideal maxillary teeth.

This design may be particularly suited for patients whose interferences (e.g., malocclusions) can be more efficiently neutralized by anterior guidance focused upon lateral poles of the mandibular component 1-2-C of the AGP 4-C, as compared to a single pointed protrusion 7 of the mandibular component 1-2 of FIG. 3, when a patient wears the splint 13 and bruxes.

The maxillary component 1-1-C of the AGP 4-C may be modified to provide three-dimensional guidance and limits to the mandible according to canine guidance when the patient bruxes. In some embodiments, the maxillary component 1-1-C of the AGP 4-C may have a concave inner surface with a cross-sectional shape in a horizontal plane forming a superellipse with convex outer sides. In other embodiments, the maxillary component 1-1-C may take on any shape configured to mate with the mandibular guidance component 1-2-C. The size of the maxillary component 1-1-C may be, for example, less than 50 mm by 50 mm dependent upon the full range of motion and border limits of the mandible both horizontally and vertically for a particular patient.

In this exemplary embodiment, there are two areas of CR contact 2a and 2b on the posterior aspect of the flat area of the maxillary component 1-1-C with a much broader area of long centric 3' on the anterior aspect of the flat area of the maxillary component 1-1-C. The steepness 33 and depth 32, as shown in FIG. 1, of the areas of lateral and protrusive guidance on the maxillary component 1-1-C of the AGP 4-C can be controlled or modified to provide anterior stops and guidance to the mandible for a very wide range of treatment goals that the dental professional may have in mind.

In some embodiments, when the patient moves his mandible in laterotrusion to the left, only the left protrusion 7b may be in contact. As the patient moves his mandible back to CR, the right protrusion 7a may move back into contact simultaneous with the left protrusion 7b. As the patient moves his mandible in laterotrusion to the right from CR, only the right protrusion 7a may be in contact with the maxillary aspect 1-1-C of the AGP 4-C.

Within the full range of motion of the TMJs 9R and 9L of the mandible 8-1, both protrusions 7a and 7b of the mandibular guidance component 1-2-C of the AGP 4-C may be in contact in CR with the maxillary guidance component 1-1-C of the AGP 4-C at points 2a and 2b or long centric area 3', or one or both protrusions 7a or 7b may be in contact with an inclined plane, lateral guidance 5, which locate on the lateral aspects of the inclined plane, or protrusive guidance 6, which locates on the anterior aspect of the inclined plane, of the maxillary component 1-1-C of the AGP 4-C to provide appropriate anterior "canine" guidance to avoid posterior interferences, eliminate engrams, reduce the force of the muscles of mastication, and to allow freedom to the condyles 8-R and 8-L of the TMJ's 9-R and 9-L to be in their best stress bearing positions regardless the patient's individual occlusion or malocclusion.

The steepness and depth of the protrusions 7a and 7b of the mandibular component 1-2-C of the AGP 4-C can be controlled to provide anterior stops and guidance to the mandible for a very wide range of treatment goals the dental professional may have in mind.

In some embodiments, the AGP 4-C may be produced and/or applied with a minimal vertical dimension 16 penalty, for example, less than 5 mm, when the patient is at rest because the elimination of posterior interferences is accomplished with three-dimensional guidance displacing the mandible inferiorly in excursions from CR. An excursion would be a movement of the mandible left, right or protrusively from the hinge axis of CR or long centric.

From the hinge axis of CR, or another point or axis of the dental professional's choosing, the three dimensional guidance of FIGS. 1, 4, 9, 10, 11, 12, 12a, 13 and 13a of the AGPs may provide anterior guidance and eliminate the interferences of all excursions to the full border limits of the mandible. And furthermore, the guidance of the AGP may be placed anterior to the anterior teeth so the physical material for that guidance (e.g., the AGP) is not developed on a splint at a position in between maxillary and mandibular anterior teeth, but rather independent of the position of anterior teeth and could be anterior (or posterior) to anterior teeth.

The AGP 4-C can be attached to the splints up-side down and with proper rotation of the AGP 4-C. In other words, the maxillary aspect of the AGP 1-1-C can be attached to a mandibular retentive piece and the mandibular aspect of the AGP 1-2-C is attached to a maxillary retentive piece, such that the AGP 4-C can be used interchangeably with the maxillary and mandibular retentive pieces.

FIG. 10 provides another exemplary design of a bruxism AGP, a "group function anterior guidance" AGP 4-G, which may be created for a different version of a bruxism splint. There may be a very broad protrusion 7' on the mandibular component 1-2-G of the AGP 4-G that would mimic group function from canine to canine, or premolar to premolar (or other teeth selected by the dental profession) in a way that would mimic ideal human group function anterior guidance. The broadness of protrusion 7' can be accentuated anterior-posteriorly and/or laterally to give freedom to the mandible or set limits to the mandible according to the treatment goals of the operator. The "group function anterior guidance" AGP 4-G may be particularly suited for patients whose particular interferences (e.g., malocclusions) can be more efficiently neutralized by anterior guidance that is broad from the left anterior lateral pole to the right anterior lateral pole of the mandibular component of the AGP, as compared to a single pointed protrusion 7 of the mandibular component 1-2 of FIG. 3, when a patient wears the splint 13 and bruxes.

The maxillary component 1-1-G of the AGP 4-G may be modified according to group function guidance when the patient bruxes. In some embodiments, the maxillary component 1-1-G of the AGP 4-G may have a concave inner surface with a cross-sectional shape in a horizontal plane forming a superellipse with convex outer sides. In other embodiments, the maxillary component 1-1-G may take on any shape configured to mate with the mandibular guidance component 1-2-G. The size of the maxillary component 1-1-G may be, for example, less than 50 mm by 50 mm dependent upon the full range of motion and border limits of the mandible both horizontally and vertically for a particular patient.

There may be a broad area of CR stop 2', which is broader in contrast to a CR stop 2 of a maxillary component that is coupled to a single pole protrusion 7 and locates on the posterior aspect of the flat area of the maxillary component, and a broad area of long centric 3', which is broader in contrast to an area of long centric 3 in a maxillary component that is coupled to a single pole protrusion 7 and locates on the anterior aspect of the flat area of the maxillary component. The steepness 33 and depth 32, as shown in FIG. 1, of the areas of lateral and protrusive guidance on the maxillary component 1-1-G of the AGP 4-G can be controlled or modified to provide anterior stops and guidance to the mandible for a very wide range of treatment goals that the dental professional may have in mind. Further, the steepness and depth of the protrusion 7' of the mandibular component 1-2-G of the AGP 4-G can be controlled to provide anterior stops and guidance to the mandible for a very wide range of treatment goals the dental professional may have in mind.

Within the full range of motion of the TMJ's 9-R and 9-L of the mandible 8-1, the broad protrusion 7' of the mandibular component 1-2-G of the AGP 4-G may be in contact in CR 2' with the maxillary aspect 1-1-G of the AGP 4-G or the long centric area 3', or a lateral aspect of the broad protrusion 7' may be in contact with an inclined plane, lateral guidance 5, which are located on both lateral aspects of the inclined plane, or protrusive guidance 6, which are located on the anterior aspect of the inclined plane of the maxillary component 1-1-G of the AGP 4-G to provide appropriate anterior "group function" guidance to avoid posterior interferences, eliminate engrams, reduce the force of the muscles of mastication, and to allow freedom to the condyles 8-R and 8-L of the TMJs 9-R and 9-L to be in their best stress bearing positions.

In some embodiments, the AGP 4-G may allow for a minimal vertical dimension 16 penalty, for example, less than 5 mm, when the patient is at rest because the elimination of posterior interferences is accomplished with three-dimensional guidance displacing the mandible inferiorly in excursions from CR and long centric. Further, the guidance of the AGP 4-G may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance, there is increased advantage over the muscles of mastication in excursions as compared to any previous system.

The AGP 4-G can be attached to the splints up-side down and with proper rotation of the AGP 4-G. In other words, the maxillary aspect of the AGP 1-1-G can be attached to a mandibular retentive piece and the mandibular aspect of the AGP 1-2-G can be attached to a maxillary retentive piece, such that the AGP 4-G can be used interchangeably with the maxillary and mandibular retentive pieces.

The three exemplary bruxism AGPs shown in FIGS. 1, 9 and 10, may provide a superior bruxism appliance to the vast majority of bruxism patients regardless their malocclusion. However, human occlusions and malocclusions are so diverse to each individual that it may not be practical to assign a particular AGP a particular occlusion or malocclusion or a particular malady like TMD. Selection of a particular AGP and possibly the modification of that AGP may require an informed decision by the dental professional using clinical judgment for a particular situation or a combination of malocclusions and maladies.

In addition to the most common use of the AGP 4, which is the treatment and amelioration of bruxism, the AGP 4 may be used to control and limit the front end of the mandible three-dimensionally independent of malocclusion or condition of the patient's teeth. Used this way, the AGP 4 may offer a wide range of solutions for other maladies of the mouth, jaws, TMJ, and sleep apnea. When using the AGP 4, not only does the dental professional have three-dimensional control of the anterior of the mandible, but dependent upon the malady and treatment proscribed, the AGP 4 can be indexed in a position of the dental professional's choosing other than CR to greatly expand the scope of treatments available. In some embodiments, the AGP 4 may be indexed and attached to retentive pieces within the splint system, not directly to teeth or the arch. With the use of an AGP 4, the dental professional has a broad spectrum of three dimensional patterning available to guide the patient's mandible to a selected destination by a wide range of three dimensional routes. Thus, a dental professional may take advantage of a wide range of very different clinical applications of the AGP 4. In some embodiments, the design of an AGP 4 may reflect the dental professional's choice and prescription to apply very different guidance and limits to the mandible and/or to each TMJ 9-R and 9-L or other variables in the stomatognathic system independently.

In regard to TMD splints, the goal in all these plethora of different occlusions and malocclusions in the context of TMD and various other damage profiles of the stomatognathic system with or without bruxism, is to provide specialized anterior guidance and limits to treat specific damage profiles of specific patients and to neutralize posterior interferences to eliminate destructive engrams associated with interferences to decrease muscle activity and spasticity, to give protection to the teeth and the TMJ, the reduction of myo-facial pain syndrome, and the reduction of migraine headache. In regard to sleep apnea, the goal is to move the mandible protrusively, and therefore the tongue forward, to increase the volume of the airway space.

FIG. 11 shows an exemplary embodiment of a TMD treatment AGP, a "bilateral anterior repositioning" TMD (sometimes called a REPO) AGP 4-TB to enable a dental professional to make an anterior repositioning splint to treat bilateral anterior disc displacement of the TMJs. Again, a very different clinical application of the AGP and a further example of the flexibility of treatments the AGP can provide to a dental professional with its ability to provide three-dimensional control of the front end of the mandible. To treat bilateral disc displacement of the TMJs, both the mandibular aspect of a AGP 1-2-TB and a maxillary aspect of the AGP 1-1-TB can be indexed so that as the patient closes his mandible 8-1, it can be guided forward and vertically to the designated position of rest 2" customized to treat the patient's damage in which both the condyles 8-R and 8-L of the TMJs 9-R and 9-L recapture both the discs bilaterally.

The maxillary aspect of the AGP 1-1-TB may have a customized protrusive guidance 6a located on the posterior aspect of the maxillary guidance component 1-1-TB (where otherwise the posterior aspect of the maxillary guidance component 1-1 shown as position 2 and 2' in FIGS. 2 and 10, respectively of a bruxism AGP would be to guide the mandible back to CR, to guide the mandible protrusively and vertically to this therapeutic position of rest 2". The position of rest or predetermined index position 2" may be designated or indexed based on the damage of each patient.

From this designated position of rest 2" that has recaptured both discs of the TMJs, the three-dimensional guidance for the mandible to long centric area 3", on the anterior aspect of the flat area, and then further to lateral guidance 5, and protrusive guidance 6, may provide symmetrical protection and therapy for the particular damage or malady each patient exhibits, elimination of posterior interferences, elimination of engrams, and the reduction of the forces of the muscles of mastication in excursions. The lateral guidance 5 may be positioned on both lateral aspects of the inclined plane of the maxillary guidance component. The protrusive guidance may be positioned on the anterior aspect of the inclined plane of the maxillary guidance component.

In some embodiments, the AGP 4-TB may provide a minimal vertical dimension 16 penalty when the patient is at rest because the anterior repositioning of the condyles 8-R and 8-L and the elimination of posterior interferences may be accomplished with three-dimensional guidance displacing the mandible 8-1 vertically in the therapeutic movement to reposition the condyles 8-R and 8-L and the excursions from this designated position 2". Further, the guidance of the AGP 4-TB may be placed anterior to the teeth so the physical material for that guidance is not in addition, but independent of and anterior to anterior teeth.

This guidance can be provided no matter the condition or even presence of teeth and because the guidance may be placed anterior to the traditional limitations of guidance where there is increased advantage over the muscles of mastication in excursions as compared to any previous system.

The AGP 4-TB can be attached to the splints up-side down and with proper rotation of the AGP 4-TB. In other words, the maxillary aspect of the AGP 1-1-TB can be attached to a mandibular retentive piece and the mandibular aspect of the AGP 1-2-TB can be attached to a maxillary retentive piece, such that the AGP 4-TB can be used interchangeably with the maxillary and mandibular retentive pieces.

A series of AGPs could be designed by the dental professional to gently "walk back" the condyles to CR as the posterior tissues are healed. For example, as the condyles heal and become positioned back further, the same AGP (or different AGPs) can be indexed in a different place to progressively move the condyles. As with any AGP construction the steepness, depth, size and shape of both components of the AGP may be modified to meet the dental professional's goals and/or the damage and malocclusion profile of a particular patient.

To treat sleep apnea, both the mandibular guidance component of an AGP 1-2-TB and a maxillary guidance component of the AGP 1-1-TB can be indexed and/or modified so that as the patient closes his mandible 8-1, it can be guided forward and vertically to the designation position of rest 2" customized to move the mandible protrusively to about 50-70% of that patient's total protrusive potential. By moving the mandible to the clinically effective protrusive position, the tongue is also moved forward to open the patient's airway to treat the patient's sleep apnea. The maxillary aspect of the AGP 1-1-TB may have a customized protrusive guidance component 6a located on the posterior aspect of the maxillary component (where otherwise the posterior aspect of the maxillary guidance component 1-1, shown as position 2 and 2' in FIGS. 2 and 10, respectively, of a bruxism AGP would be to guide the mandible into centric relation) to guide the mandible protrusively and vertically to this therapeutic position of rest 2". The position of rest 2" may be designated or indexed based on the distance that the mandible should be moved protrusively to effectively treat sleep apnea of each patient.

From this designated position of rest 2" that has adequately opened the airway, the three-dimensional guidance for the mandible to long centric area 3", on the anterior aspect of the flat area, and then further to the lateral guidance 5, and protrusive guidance 6, may provide symmetrical guidance, eliminate posterior interferences, eliminate engrams, and reduce forces of the muscles of mastication in excursions. The lateral guidance 5 may be positioned on both lateral aspects of the inclined plane of the maxillary guidance component 1-1-TB. The protrusive guidance 6 may be positioned on the anterior aspect of the inclined plane of the maxillary guidance component 1-1-TB.

In some embodiments, the AGP 4-TB may provide a minimal vertical dimension 16 penalty when the patient is at rest because the anterior repositioning of the mandible and the elimination of posterior interferences may be accomplished with three-dimensional guidance displacing the mandible 8-1 vertically in the therapeutic movement to anteriorly reposition the mandible 8-1 for airway opening and the excursions from this designated position 2". Further, the guidance of the AGP 4-TB may be placed anterior to the teeth so the physical material for that guidance is not in addition to, but independent of and anterior to, the anterior teeth.

This guidance can be provided no matter the condition or even presence of teeth. Further, as the guidance may be placed anterior to the guidance of existing systems, it can provide increased advantage over the muscles of mastication in excursions.

In some embodiments, the AGP 4-TB can be attached to the splints up-side down with proper rotation of the AGP 4-TB. That is, the maxillary aspect of the AGP 1-1-TB can be attached to the mandibular retentive piece and the mandibular aspect of the AGP 1-2-TB can be attached to the maxillary retentive piece such that the AGP 4-TB can be used interchangeably with the maxillary and mandibular retentive pieces.

Figure 12:
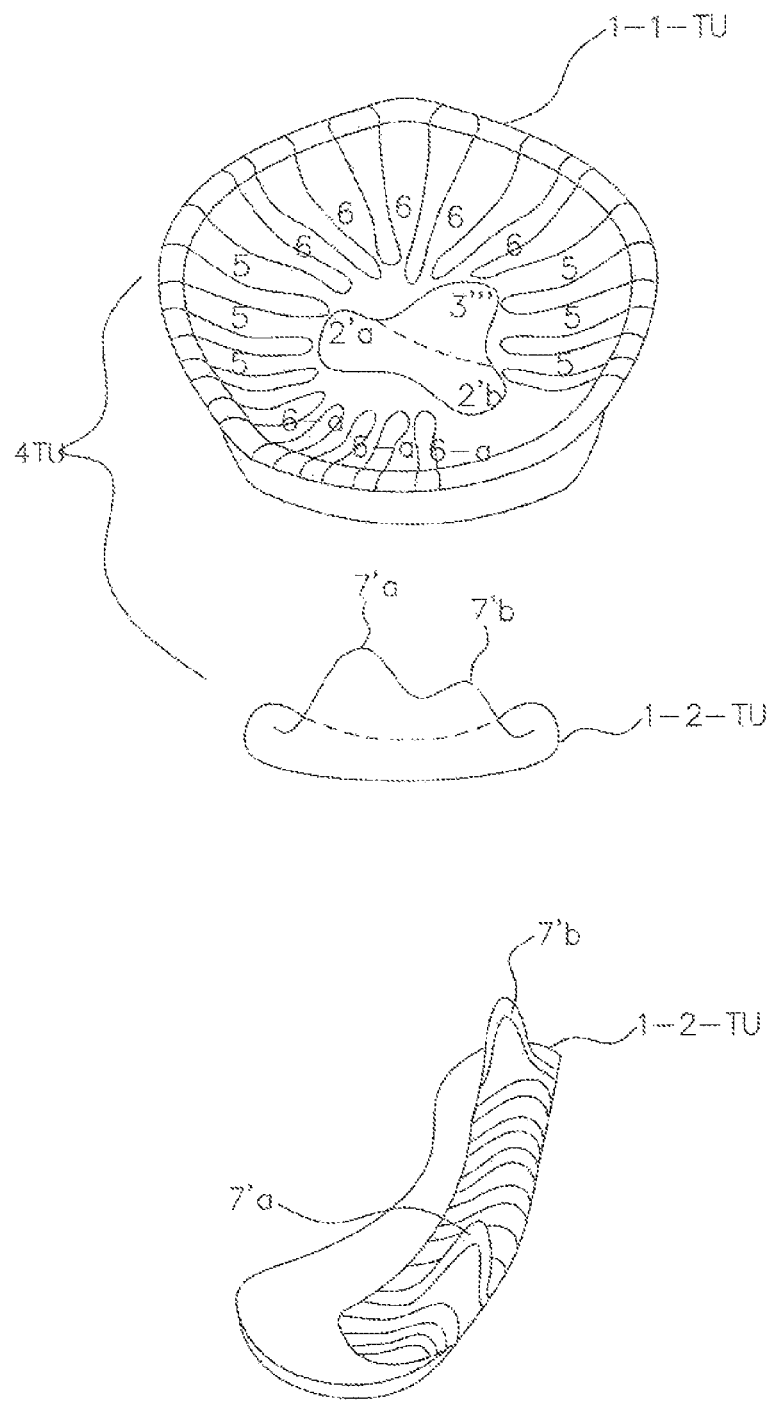
FIG. 12 is a planar perspective view of a "unilateral anterior repositioning" TMD AGP for a patient who has a damaged disc within the right TMJ in accordance with an exemplary embodiment.

FIG. 12 shows another exemplary embodiment of a TMD treatment AGP, a "unilateral anterior repositioning" AGP 4-TU to enable a dental professional to create a TMD treatment splint that can be selective and differential to each TMJ 9-R and 9-L or other unilateral maladies of the mandible 8-1, or supporting structures. Again, this is another example of a very different clinical application, taking advantage of the robust flexibility of the AGP.

In this exemplary embodiment, the patient has an anteriorly displaced meniscus in the right TMJ 9-R, and the left TMJ 9-L is normal. The dental professional may proscribe an AGP 4-TU that anteriorly repositions the right TMJ 9-R to recapture the displaced meniscus, but allows the left TMJ 9-L to be in CR.

On the mandibular aspect of the AGP 1-2-TU there may be two protrusions 7'*a* and 7'*b* in which the protrusion on the right 7'*a* is taller and steeper than the protrusion on the left 7'*b*. The maxillary aspect 1-1-TU of the AGP 4-TU may be modified accordingly. The right area of anterior repositioning 2'*a*, which recaptures the anteriorly displaced disc of the right TMJ, may be located anteriorly and have a deeper indentation that is located anteriorly on the right aspect of the flat area of the maxillary component, and may have customized anterior protrusive guidance 6*a*, posterior to the proscribed area of rest 2'*a* in contrast to the position of rest 2'*b*, which locates on the left posterior aspect of the flat area of the maxillary component, to enable the operator to anteriorly reposition the right condyle 8-R while allowing the left condyle 8-L to assume CR at rest.

In this exemplary embodiment, as the patient closes his mandible 8-1, the right condyle 8-R may be guided anteriorly and vertically by the broader and taller right protrusion 7'*a* of the mandibular aspect 1-2-TU of the AGP 4-TU into the deeper and broader area 2'*a* of the maxillary aspect 1-1-TU of the AGP 4-TU to recapture the displaced disc of the right TMJ 9-R. The left condyle 8-L of the left TMJ 9-L may be guided into its CR position by the left protrusion 7'*b* of the mandibular aspect 1-2-TU of the AGP 4-TU into the CR position 2'*b* of the maxillary aspect 1-1-TU of the AGP 4-TU.

From this therapeutically designated position of rest 2'*a* and 2'*b*, based on the patient's damage profile, which has recaptured the right disc of the right TMJ 9-R, the three-dimensional guidance to long centric rest 3''' and then further to lateral guidance 5, and protrusive guidance 6, may provide asymmetrical protection and therapy for the particular damage or malady this patient exhibits, elimination of posterior interferences, elimination of engrams, and the reduction of the forces of the muscles of mastication.

The AGP 4-TU may provide a minimal vertical dimension 16 penalty when the patient is at rest because the anterior repositioning of the right condyle 8-R and the elimination of posterior interferences is accomplished with three-dimensional guidance displacing the mandible 8-1 vertically in the therapeutic movement to reposition the right condyle 8-R and the excursions from this designated therapeutic position. Further, the guidance of the AGP 4-TU may be placed anterior to the teeth so the physical material for that guidance is not in addition, but independent of and anterior to anterior teeth. This guidance may be provided no matter the condition or even presence of teeth and because the guidance may be placed anterior to the traditional limitations of guidance there can be increased advantage over the muscles of mastication in excursions as compared to any previous system.

The AGP 4-TU can be attached to the splints up-side down and with proper rotation of the AGP 4-TU. In other words, the maxillary aspect of the AGP 1-1-TU may be attached to a mandibular retentive piece and the mandibular aspect of the AGP 1-2-TU may be attached to a maxillary retentive piece, such that the AGP 4-TU can be used interchangeably with the maxillary and mandibular retentive pieces.

FIG. 12-*b* shows the opposite configuration of FIG. 12, in which the patient has an anteriorly displaced meniscus in the left TMJ 9-L, and the right TMJ 9-R is normal. The dental professional may proscribe an AGP 4-TU that anteriorly repositions the left TMJ 9-L to recapture the displaced meniscus, but allows the right TMJ 9-R to be in CR.

On the mandibular aspect of the AGP 1-2-TU there may be two protrusions 7'*a* and 7'*b* in which the protrusion on the left 7'*a* is taller and steeper than the protrusion on the right 7'*b*. The maxillary aspect 1-1-TU of the AGP 4-TU may be modified accordingly. The left area of anterior repositioning 2'*a*, which recaptures the anteriorly displaced disc of the left TMJ, may be located anteriorly and have a deeper indentation than is located anteriorly on the right aspect of the flat area of the maxillary component, and have customized anterior protrusive guidance 6*a*, posterior to the proscribed area of rest 2'*a* in contrast to the position of rest 2'*b*, which locates on the right posterior aspect of the flat area of the maxillary component, to enable the operator to anteriorly reposition the left condyle 8-L while allowing the right condyle 8-R to assume CR at rest.

In this exemplary embodiment, as the patient closes his mandible 8-1, the left condyle 8-L may be guided anteriorly and vertically by the broader and taller left protrusion 7'*a* of the mandibular aspect 1-2-TU of the AGP 4-TU into the deeper and broader area 2'*a* of the maxillary aspect 1-1-TU of the AGP 4-TU to recapture the displaced disc of the left TMJ 9-L. The right condyle 8-R of the right TMJ 9-R may be guided into its CR position by the right protrusion 7'*b* of the mandibular aspect 1-2-TU of the AGP 4-TU into the CR position 2'*b* of the maxillary aspect 1-1-TU of the AGP 4-TU.

From this therapeutically designated position of rest 2'*a* and 2'*b*, based on the patient's damage profile, which has recaptured the left disc of the left TMJ 9-L, the three-dimensional guidance to long centric rest 3''' and then further to lateral guidance 5, and protrusive guidance 6, may provide asymmetrical protection and therapy for the particular damage or malady this patient exhibits, elimination of posterior interferences, elimination of engrams, and the reduction of the forces of the muscles of mastication.

The AGP 4-TU may provide a minimal vertical dimension 16 penalty when the patient is at rest because the anterior repositioning of the left condyle 8-L and the elimination of posterior interferences is accomplished with three-dimensional guidance displacing the mandible 8-1 vertically in the therapeutic movement to reposition the left condyle 8-L and the excursions from this designated therapeutic position. Further, the guidance of the AGP 4-TU may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance there can be increased advantage over the muscles of mastication in excursions as compared to any previous system.

The AGP 4-TU can be attached to the splints up-side down and with proper rotation of the AGP 4-TU. In other words, the maxillary aspect of the AGP 1-1-TU may be attached to a mandibular retentive piece and the mandibular aspect of the AGP 1-2-TU may be attached to a maxillary retentive piece, such that the AGP 4-TU can be used interchangeably with the maxillary and mandibular retentive pieces.

FIG. 13 and its mirror image FIG. 13a are two more exemplary embodiments of a TMD treatment AGP, an "asymmetric TMD treatment" AGP 4-AT to enable a dental professional to treat a mandible that has had damage to one TMJ, or both TMJs, or the muscles, ligaments, or tendons of mastication unilaterally or bilaterally, or other clinical problems or combinations of clinical problems in which the operator needs the ability to control the movements and limits of the front end of the mandible in non-traditional three dimensional pathways symmetrically or asymmetrically. This is a very different clinical application of the AGP. The design of this exemplary AGP 4-AT may reflect the dental professional's prescription to apply very different guidance and limits to each TMJ 9-R and 9-L or other variables in the stomagognathic system independently.

In this example, the protrusion 7''' may be located laterally to the midline. The asymmetrical depth and steepness of both the mandibular aspect 1-2-AT and the maxillary aspect 1-1-AT of the AGP 4-AT can be controlled to provide anterior stops, limits and guidance for the treatment goals of the operator in this case asymmetrically providing very different parameters to each TMJ 9-R and 9-L. In this circumstance the patient's mandible 8-1 upon closing may be guided into a position of rest 2''', which is other than CR that is proscribed by the dental professional for each patient's particular malady or damage. From this designated position of rest 2''' the three-dimensional guidance to long centric 3''' which has a customized shape, which is designed based on the damage of a specific patient on the anterior aspect of the flat area of the maxillary component, to provide guidance for this particular damage profile and then further to lateral guidance 5, and protrusive guidance 6, provided asymmetrically in this case, but could also be symmetrical protection and therapy for the particular damage or malady of a specific patient. The lateral guidance 5 may be positioned on both lateral aspects of the inclined plane of the maxillary guidance component. The protrusive guidance 6 may be positioned on the anterior aspect of the inclined plane of the maxillary guidance component.

The AGP 4-AT can be attached to the splints up-side down and with proper rotation of the AGP 4-AT. In other words, the maxillary aspect of the AGP 1-1-AT may be attached to a mandibular retentive piece and the mandibular aspect of the AGP 1-2-AT may be attached to a maxillary retentive piece, such that the AGP 4-AT can be used interchangeably with the maxillary and mandibular retentive pieces.

CAD-CAM AGP Splint

A CAD-CAM AGP splint could be custom produced by a dental professional in an unprecedented way providing solutions to a variety of conditions and or combinations of conditions and at a significant lesser expense to both the dental professional and the patient. The dental professional may have a broad spectrum of three-dimensional patterning available to guide the patient's mandible to the chosen destination by a route among a broad spectrum of three dimensional routes.

Embodiments of the methods described herein can be applied to a wide range of stock AGPs, and/or a stock AGP that is then modified by the dental professional, and/or a custom designed AGP for a specific patient. The AGP chosen, chosen and modified, or designed could be one of many possibilities of size, shape or style to address a very wide range of problems or malocclusions. The maxillary component and/or the mandibular component of the AGP can be chosen, chosen and modified, or designed to one among many choices of shape or size either individually or as a group to achieve whatever effect the operator desires. For instance, a TMD therapist may have available to her/him an unprecedented range of options regarding both limits and guidance to the mandible. In contrast to other systems, some embodiments of the disclosed AGP can provide three dimensional anterior guidance and limits to the mandible independent of the condition, position, presence or absence of teeth. Also uniquely attributable to the AGP, the position of the AGP (and therefore guidance and limits of the mandible within the AGP splint) can be controlled to maximize or minimize different properties of the AGP splint to include increased or decreased mechanical advantage over the muscles of mastication in excursions. In some embodiments, the AGP may be indexed and attached to retentive pieces within the splint system, not directly to teeth or the arches. Considering the unprecedented choices, modification and design potential of the AGP, and the flexibility regarding the position of the AGP within the AGP splint system, the CAD-CAM AGP splint, and the CAD-CAM TMD AGP splint are advantageous over existing night guards, TMD appliance systems, and sleep apnea appliance systems.

The CAD-CAM AGP splint may be a two-piece, customized, comfortable to wear, seamless, light-weight, minimal vertical dimension at rest in CR (or a different index position of the dental professional's choosing) appliance that provides three dimensional anterior guidance and limits.

In some embodiments, the AGP may be placed or indexed (and therefore three dimensional guidance placed within a broad range transversely on the splint system) anterior (or posterior) to the teeth and therefore not in between the teeth so the material which provides the guidance may not add any vertical height to the appliance to allow an appliance of minimal vertical dimension at rest. Further, because the guidance may be located even further anterior to the muscles of mastication than teeth, an AGP equipped splint may have inherent superior mechanical advantage over the muscles of mastication in excursions as compared to any guidance involving teeth or built on teeth. In some embodiments, the AGP may be indexed and attached to retentive pieces within the splint system, not directly to teeth or the arch. In contrast to existing night guards, TMD treatment systems, and sleep apnea treatment systems, the CAD-CAM AGP splint may have a broad range of three-dimensional flexibility in the choice, modification and design of the anterior guidance and limits. Further, the CAD-CAM AGP splint and the CAD-CAM TMD AGP splint can be produced without regard or concern as to the condition, presence or absence of teeth, to include anterior teeth, because the guidance is provided entirely by the AGP.

In the event the patient's CAD-CAM AGP splint is lost or destroyed, a digital record may exist to recreate a duplicate appliance quickly, without the need of a new record making appointment. A new CAD-CAM AGP splint replacement can be provided conveniently, and with cost savings for the patient.

The CAD-CAM AGP splint can be produced less expensively than traditional methods of the dentist and his lab manually producing and adjusting a splint. The CAD-CAM AGP splint is a superior splint for addressing TMD issues, bruxism, and sleep apnea. The CAD-CAM AGP splint in contrast to all existing systems will provide a superior system to the patient, with greater convenience for the patient, and at a better price.

Embodiments of the disclosed methods for producing a customized AGP equipped splint may be more convenient, less expensive, and less work intensive for both the dental professional and the patient.

In one embodiment, a method of automatically producing or reproducing a customized AGP equipped splint involves combining digital methods and/or traditional methods converted to digital to collect and create information needed to automatically fabricate a specifically customized AGP equipped splint for a specific patient. When the patient needs a new AGP equipped splint due to loss or damage, because the digital record can be retained, a new AGP equipped splint can be provided without records being collected by the dental professional again.

After the dental and arch information, which is collected from a specific patient, and the AGP splint design is stored in a computer, a new AGP equipped splint could be produced by a CNC (Computer Numerical Control) lab or an in office 3D printer, without any further work by the dentist or patient. Alternatively, if one or two variables regarding the patients' teeth or arch or movement parameters have changed, these could be changed in the computer records, the design changed accordingly and then sent to a CNC lab or 3D printer, and a new AGP equipped splint could be produced without the necessity of a complete records collection session by the dentist and patient.

Procedure of Making a CAD-CAM AGP-Splint

In one exemplary embodiment, the procedure for the collection and creation of a patient's dental information record may include:

1a) Gather 3D information of the maxillary and mandibular teeth and arches, which may involve using traditional methods (e.g., making impressions of the patients' teeth and arches and then pour in stone to make models and convert to digital by scanning the models) or directly recording the 3D information of the maxillary and mandibular teeth and arches with an in-office scanner or other data acquisition device.

Next, for a bruxism AGP splint, when the dental professional intends to use a simple bruxism AGP (e.g., as shown in FIGS. 2 to 4), or a "canine guidance" bruxism AGP 4-C (e.g., as shown in FIG. 9) or a "group function" bruxism AGP 4-G (e.g., as shown in FIG. 10), the dental professional may collect a CR of the mandible record at first contact of teeth and arches, which may involve using traditional methods (e.g., by manipulating the mandible into CR hinge axis and closing the mandible until first contact of the teeth and/or arches, making an index of that relationship of the teeth and arches, and mounting the models of teeth and arches together in that relationship) and converting to digital by scanning the mounted models or directly recording the relationship of the maxillary and mandibular teeth and arches of the mandible in CR at first contact using an in-office scanner or another data acquisition device. The dental professional may also use a combination of three-dimensional radiography combined with intraoral scanning. The three-dimensional radiography may be correlated or indexed with the intraoral scanning data and coincident to CR position of the mandible 8-1 at first contact of teeth and/or arches as interpreted by the dental professional through three-dimensional radiography, and that position of first contact of the teeth and arches may be recorded when the mandible is in CR directly using the correlated intraoral scanning data.

Alternatively, in the case of a TMD AGP splint, the dental professional may establish the appropriate position of rest by one or more methods. The dental professional can manually manipulate the patient's mandible as a part of his direct clinical evaluation establishing the appropriate position of rest when the mandible is closed, through communicating directly with the patient and clinical judgment. The dental professional may then record the relative relationship of the mandible to the maxilla at that position of rest by scanning the models of the teeth and arches that have been made from the patient in that position or directly record that relationship between maxillary and mandibular teeth and arches in that position with an in-office scanner. The dental professional may also use a combination of three-dimensional radiography combined with intraoral scanning. The three-dimensional radiography may be correlated or indexed with the intraoral scanning data. The dental professional may interpret through three-dimensional radiography the damage profile of that patient to include the therapeutic position of rest. The dental professional may record that relative relationship of the mandible to the maxilla at that position of first contact of the teeth at rest using the correlated intraoral scanning data. Some types of TMJ and stomatognathic damage may be recorded with alternative imaging such as MRI (Magnetic Resonance Image) and sonography. The alternative imaging may be combined with traditional methods of making indexed models of patients' teeth in the designated position of rest and then scanning or directly record that position with an in-office scanner.

In the case of a bilateral anterior disc displacement in which the dental professional intends to use a "bilateral anterior repositioning" TMD AGP 4-TB, the dental professional may identify through manual manipulation of the mandible, direct communication with the patient, and clinical judgment, where the mandible (using the teeth and arches for indexing) should be indexed at rest to the maxilla (using teeth and arches for indexing), protrusively, laterally, and vertically to recapture the discs of both TMJs 9 R and L.

The dental professional may advance the mandible protrusively enough from the CR position so that the condyles 8 R and L of the mandible 8-1 will recapture both the right and left discs within their respective TMJs 9 R and L.

In some embodiments, the damage (e.g., anterior displacement) of the discs may be of equal distance anteriorly from their respective CR positions so that the recapture of the discs may require the same protrusive distance anterior from CR position of each respective condyle 8 R and L within each respective TMJ 9 R and L. Further, the damage (e.g., anterior displacement) of the discs may not be of equal distance anteriorly from their respective CR positions so that the recapture of the discs may require different protrusive distances when comparing the right condyle protrusively from CR position of the right TMJ to the left condyle protrusively from CR of the left TMJ.

If the protrusive value (e.g., distance) of the two condyles to recapture their respective discs is equal, there may not be any lateral movement of the mandible and the mid-sagittal plane of the mandible will remain coincident with the mid-sagittal plane of the maxilla.

If the right and left protrusive values (e.g., distances) of the two condyles to recapture their respective discs are different, then the lateral value of the rest position of the mandible may be either to the right or left of the mid-sagittal plane of the maxilla.

If the left condyle 8L must travel relatively further than the right condyle 8R protrusively to recapture its relative disc, then the lateral swing positioning of the mid-sagittal plane of the mandible may be located to the right of the mid-sagittal plane of the maxilla 26 proportionally to the relative differential distances traveled by the condyles to recapture their discs respectively bilaterally. FIG. 11-*b* shows the exemplary indexing of the mandible right laterally to the maxilla.

If the right condyle 8R must travel relatively further than the left condyle 8L protrusively to recapture its relative disc then the lateral swing positioning of the mid-sagittal plane of the mandible may be located to the left of the mid-sagittal plane of the maxilla 26 proportionally to the relative differential distances traveled by the respective condyles to recapture their discs bilaterally. FIG. 11-*a* shows an exemplary indexing of the mandible left laterally to the maxilla.

The vertical value may be the first contact (e.g., contact position of the worst interference) of teeth and arches for this protrusive and lateral position of the mandible already established to recapture the discs bilaterally.

The dental professional can then record the relative relationship of the mandible to the maxilla at that position of rest using traditional methods of creating models of the patient's teeth in that position and convert to digital by scanning the mounted models or directly record the relationship of the maxillary and mandibular teeth and arches in that position of rest using an in-office scanner or other data acquisition device. The dental professional may also use a combination of three-dimensional radiography combined with intraoral scanning. The three-dimensional radiography may be correlated or indexed with the intraoral scanning data. The dental professional may interpret through three-dimensional radiography the damage profile of that patient to include where the mandible should be at rest protrusively, laterally, and vertically to recapture the discs of both TMJs 9 R and L. The dental professional may record that relative relationship of the mandible to the maxilla at that position of rest using the correlated intraoral scanning data. Some types of TMJ damage may be recorded with alternative imaging such as MRI and sonography. Alternatively, the position of rest may be recorded using alternative imaging combined with traditional methods of making indexed models of patient's teeth in the designated position of rest and then scanning or directly record that position with an in-office scanner or other data acquisition device.

In the case of sleep apnea in which the dental professional intends to use a "bilateral anterior repositioning" TMD AGP 4-TB, the dental professional may identify through manual manipulation of the mandible, direct communication with the patient, and/or clinical judgment, where the mandible should be indexed at rest to the maxilla (e.g., using teeth and arches for indexing), protrusively, laterally, and vertically to anteriorly (protrusively) relocate the mandible to get effective airway opening.

The dental professional may advance the mandible symmetrically protrusively about 50 to 70% of the maximum protrusive potential of that patient from the CR position so that the mandible, and therefore the tongue, is relocated adequately forward to effectively open the airway.

The vertical value may be the first contact (e.g., contact position of the worst interference) of teeth and arches for this protrusive and lateral position of the mandible already established to open the airway effectively.

The dental professional can then record the relative relationship of the mandible to the maxilla at that position of rest using traditional methods of creating models of the patient's teeth in that position and convert to digital by scanning the mounted models or directly record the relationship of the maxillary and mandibular teeth and arches in that position of rest using an in-office scanner or other data acquisition device In the case of a unilateral anterior disc displacement in which the operator intends to use a "unilateral anterior repositioning" TMD AGP 4-TU (e.g., as shown in FIG. 12 and FIG. 12*a*), the dental professional may identify through manual manipulation of the mandible, direct communication with the patient, and clinical judgment, where the mandible should be at rest protrusively, laterally and vertically (three-dimensionally) to recapture the disc of the damaged TMJ while leaving the other condyle (of the other TMJ) in a relatively normal albeit rotated position.

If the damaged disc (e.g., anteriorly displaced disc) is within the left TMJ, the dental professional may advance the mandible protrusively enough to advance the left condyle from the CR position to recapture that disc, while simultaneously swinging the mandible laterally to the right to allow the right condyle of the right TMJ to stay in its CR position which will also rotate that condyle. Both the final right lateral swing position of the mandible, which will position the mid-sagittal plane of the mandible to the right of the mid-sagittal plane of the maxilla 26, and the rotation of the right condyle may be proportional to the distance traveled by the left condyle to recapture its disc, as shown in FIG. 11-*b*.

If the damaged disc (e.g., anteriorly displaced disc) is within the right TMJ 9R, the dental professional may advance the mandible protrusively enough to advance the right condyle from its' CR position to recapture that disc, while simultaneously swinging the mandible laterally to the left to allow the left condyle 8L of the left TMJ 9L to stay in its CR position which will also rotate that condyle. Both the final left lateral swing position of the mandible 8-1, which will position the mid-sagittal plane of the mandible to the left of the mid-sagittal plane of the maxilla 26, and the rotation of the left condyle 8L may be proportional to the distance traveled by the right condyle 8R to recapture its disc, as shown in FIG. 11-*a*.

The vertical value may be the first contact (e.g., contact position of the worst interference) of teeth and arches for this protrusive and lateral position of the mandible already established that will recapture the disc within the damaged TMJ and leave the other condyle within the undamaged TMJ in a relatively normal albeit rotated position.

The dental professional can then record that relative relationship of the mandible to the maxilla at that position of rest using traditional methods of creating models of the patient's teeth in that position and convert to digital by scanning the mounted models or directly record the relationship of the maxillary and mandibular teeth and arches in that position of rest using an in-office scanner.

The dental professional may also use a combination of three-dimensional radiography combined with intraoral scanning. The three-dimensional radiography may be correlated or indexed with the intraoral scanning data. The dental professional may interpret through three-dimensional radiography the damage profile of that patient to include where the mandible should be at rest protrusively, laterally and vertically (three-dimensionally) in reference to the maxilla to recapture the disc of the damaged TMJ, while leaving the other condyle (of the other TMJ) in a relatively normal albeit rotated position. The dental professional may record that relative relationship of the mandible to the maxilla at that position of rest using the correlated intraoral scanning data. Some types of TMJ damage may be recorded with alternative imaging such as MRI and sonography. Alternatively, the position of rest may be recorded using alternative imaging combined with traditional methods of making indexed models of the patient's teeth in the designated position of rest and then scanning or directly record that position with an in-office scanner or another data acquisition device.

In the case of various other damage to the stomagnathic system in which the dental professional wants to protect or treat damage to any one or combination of other structures to include damage to a TMJ, or the muscles, ligaments, or tendons of mastication unilaterally, or other clinical problems in which the dental professional needs the ability to control the movements and limits of the front end of the mandible asymmetrically or symmetrically in non-traditional pathways and intends to use an "asymmetric TMD treatment" TMD AGP, the dental professional may identify the best position of rest for the appropriate therapeutic treatment of the mandible, TMJ, or other stomatognathic malady of the mandible for that patient through manual manipulation of the mandible, direct communication with the patient, and clinical judgment, where the mandible should be at rest protrusively, laterally, and vertically (three-dimensionally) to treat or protect a TMJ, or the muscles, ligaments, or tendons of mastication, or various other clinical problems or combinations of clinical problems.

In this example, as shown in FIG. 13, the damaged structure is a damaged ligament on the right side of the mandible. The dental professional may advance the mandible protrusively enough to advance the right condyle 8R from the CR position to protect the damaged ligament, while simultaneously swinging the mandible laterally to the left to allow the left condyle 8L of the left TMJ 9L to stay in its CR position, which will also rotate that condyle. Both the final left lateral swing position of the mandible 8-1, which will position the mid-sagittal plane of the mandible to the left of the mid-sagittal plane of the maxilla 26 (as shown in FIG. 11-*a*), and the rotation of the left condyle 8L may be proportional to the distance traveled by the right condyle 8R to protect the damaged ligament.

Another exemplary situation for using an "asymmetric TMD treatment" TMD AGP splint may be to treat a damaged structure on either the left or right side of the stomatognathic system. In this example, there may be a damaged ligament lateral to the mid-sagittal plane of the mandible. The dental professional may position the mandible protrusively in a position to protect the damaged ligament. This may be an index position in which the mid-sagittal plane of the mandible is lateral to the mid-sagittal plane of the maxilla. The final lateral swing position of the mandible 8-1, which will position the mid-sagittal plane of the mandible to the right or left of the mid-sagittal plane of the maxilla 26 (as shown in FIG. 11-*a* and FIG. 11-*b* may be proportional to the relative distances traveled by each condyle to protect the damaged ligament. The vertical value may be the first contact (e.g., contact position of the worst interference) of teeth and arches for this protrusive and lateral position of the mandible already established that will protect the damaged ligament.

The dental professional can then record that relative relationship of the mandible to the maxilla at that position of rest using traditional methods of creating models of the patients' teeth in that position and convert to digital by scanning the mounted models or directly record the relationship of the maxillary and mandibular teeth and arches in that position of rest using an in-office scanner or another data acquisition device. Alternatively, three dimensional radiography with correlated intraoral scanning may be used to record position of rest. The three-dimensional radiography is correlated or indexed with the intraoral scanning data. The dental professional may interpret using three dimensional radiography the damage profile of that patient to include where the mandible should be at rest protrusively, laterally and vertically (three-dimensionally) to protect the damaged mandibular structure. The dental professional may record that relative relationship of the maxilla to the mandible at that position of rest using the correlated intraoral scanning data. Some types of TMJ and stomatognathic damage may be recorded with alternative imaging such as MRI and sonography. Alternatively, the position of rest may be recorded using alternative imaging combined with traditional methods of making indexed models of patient's teeth in the designated position of rest and then scanning or directly record that position with an in-office scanner.

Figure 14:
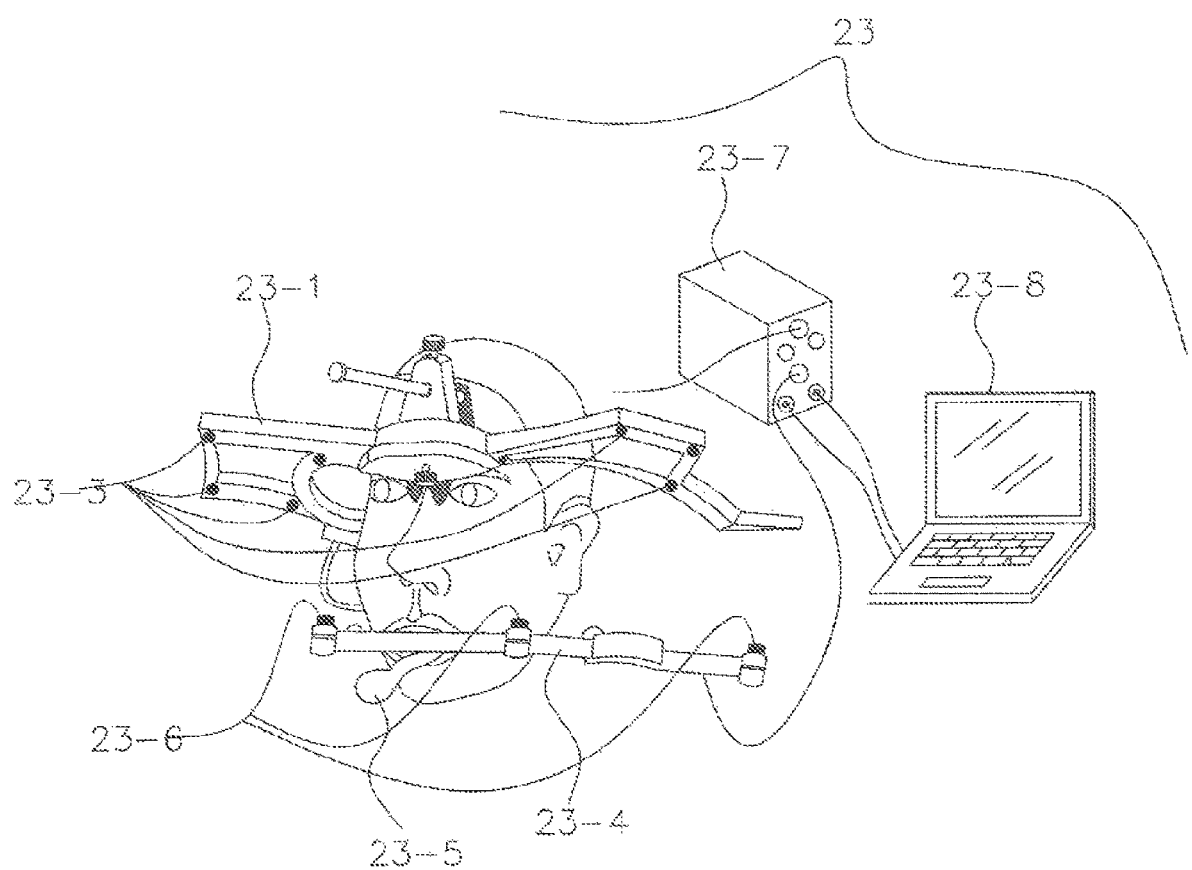
FIG. 14 is a perspective view of a Jaw Motion Analyzer for collecting TMJ data from a patient and visualization of jaw movement of a patient in real time in accordance with an exemplary embodiment.

1-b) For an AGP bruxism splint, when the dental professional intends to use a simple bruxism APG 4 (e.g., as shown in FIGS. 2 to 4), or a "canine guidance" bruxism AGP 4-C (e.g., as shown in FIG. 9) or a "group function" bruxism AGP 4-G (e.g., as shown in FIG. 10), the dental professional may use average TMJ values or gather TMJ records using traditional methods and/or by using axiography and/or a Jaw Motion Analyzer, as shown in FIG. 14. These records may include, but are not limited to, facebow transfer, intercondylar distance, condylary inclination, Bennet angle and border limits. FIG. 14 shows an exemplary Jaw Motion Analyzer system 23, which enables the collection of these data and visualization of jaw movement of a patient in real time. It may comprise of an upper receiver 23-1 that is mounted on the upper face defining parameters to include the locations of the TMJs of a patient, and may be equipped with paramagnetic sensors 23-3. This unit may also include a lower receiver 23-4 that is mounted on the lower jaw of a patient, connected to the mandibular teeth of the patient via a metal splint 23-5 and another set of paramagnetic sensors 23-6 thereon, a converter 23-7 that converts the signal from the sensors 23-3, 23-6 to a computer 23-8. In the circumstance of TMD AGP (e.g., as shown in FIGS. 11, 12, 12*a*, 13 and 13*a*) splint, additional records may be collected regarding the damage profile of that patient to include three-dimensional radiography, MRI, sonography, or collection of TMJ records in a traditional way with a manual articulator combined with clinical observation of the pain and damage profile, and/or other methods.

For an AGP sleep apnea splint, when the dental professional intends to use a "bilateral anterior repositioning" TMD AGP, as shown in FIG. 11, the dental professional may use average TMJ data or gather TMJ records using traditional methods and/or by using axiography and/or a Jaw Motion Analyzer, as shown in FIG. 14. These records may include, but are not limited to, facebow transfer, intercondylar distance, condylary inclination, Bennet angle and border limits.

2-a) Set the patient's virtual 3D maxillary and mandibular teeth and arch in CR at first contact data, or the point of rest (an exemplary predetermined index position) of the operators choosing data into the virtual articulator-CAD program, which may be already stored in a computer. Virtually position the digital models of the patient's maxillary and mandibular teeth and arches on the Virtual Articulator 24 to set up a screen visualizing a Virtual Articulator 24 with patient's virtual models 25.

2-b) Set the TMJ/condylar records into the virtual articulator-CAD program, with the records collected from the patient or use average measures. In the case of a TMD patient, additional TMJ data may be placed in the Virtual Articulator 24 regarding the damage or malady profile of that patient. This damage profile data may have been collected in the clinical exam, radiographic information, MRI or sonography. This additional information can be added to modify the movement parameters of the TMJs.

3) Virtually open the distance between the virtual models 25 by opening the virtual mandible along the appropriate arc of opening (e.g., along the CR hinge axis for a bruxism AGP splint or another arc as proscribed by the dental professional for a TMD AGP splint or sleep apnea AGP splint) according to the TMJ data to an adequate distance to virtually apply the retentive piece material at a thickness of 1 mm per arch and also provide at least a 1 mm threshold clearance between the retentive pieces. The threshold clearance may be sufficient to prevent the grinding or contact of maxillary teeth with mandibular teeth despite movement in sagittal, transverse, or vertical directions. Virtually apply the maxillary retentive piece 27 and the mandibular retentive piece 28 (here, the retentive pieces may be different based on the malocclusion) to both arches of maxillary 22 and mandibular 20 at a thickness of 1 mm. In this step, apply the special retentive piece 10 and the regular retentive piece 19 separately to maxillary arch 22 and mandibular arch 20 based on the Class of the malocclusion of the patient as shown in the FIGS. 6, 7 and 8.

For a patient that does not have a severe malocclusion, Class I, special retentive pieces 10 may be applied to both maxillary arch 22 and mandibular arch 20 as shown in FIG. 6. The shelves 11 may be placed later in step 8.

Figure 15:
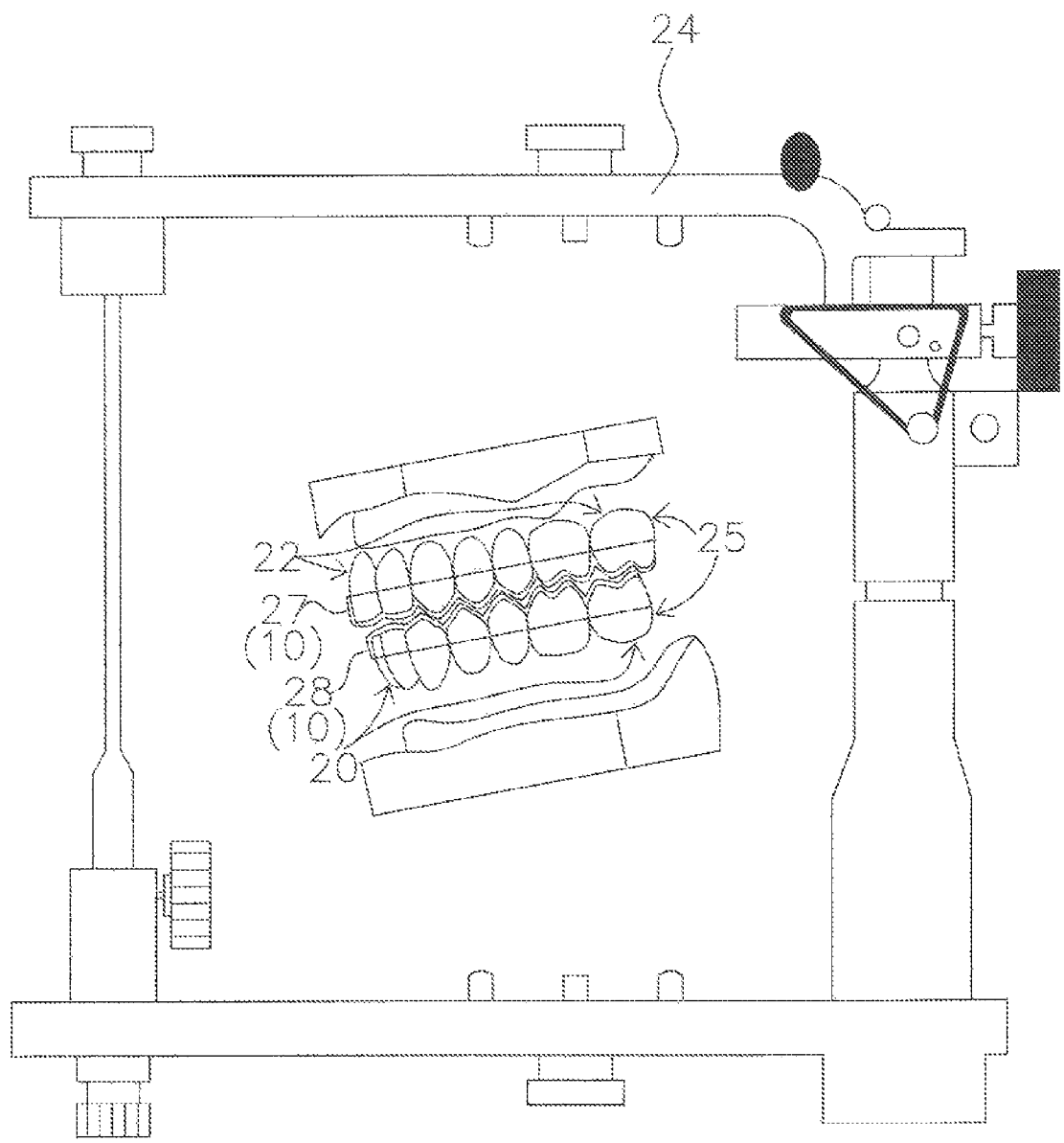
FIG. 15 is a computer screen of a virtual articulator when virtual models of a patient's teeth are set up based on the input data from a patient, who has a Class I occlusion, and have the virtual retentive pieces in place in accordance with an exemplary embodiment.

FIG. 15 shows an exemplary computer screen of a Virtual Articulator/CAD system 24 when virtual models 25 of the patient's teeth and arches are set up based on the input data from a patient, who has a Class I occlusion, which was collected from step 1-*a* and *b*, and the virtual retentive pieces have been applied to the virtual models. The shelves 11 may be placed later in step 8.

4. On the Virtual Articulator 24 with the virtual retentive pieces 27, 28 in place and the jaw position beginning in virtual CR at first contact, or an appropriate position of rest (predetermined index position) as designated by the dental professional, animate and measure the jaw movements to include laterotrusion to all border limits of the mandible.

5. In the case of a bruxism AGP appliance or a sleep apnea AGP appliance, define the movement parameters and perform collision (e.g., interference) detection in order to identify the movement restrictions. These movement restrictions, contact points and depths may be identified. For a TMD AGP splint the additional TMJ data may alter the overall movement parameters, movement restrictions, contact points and depths.

Figure 16:
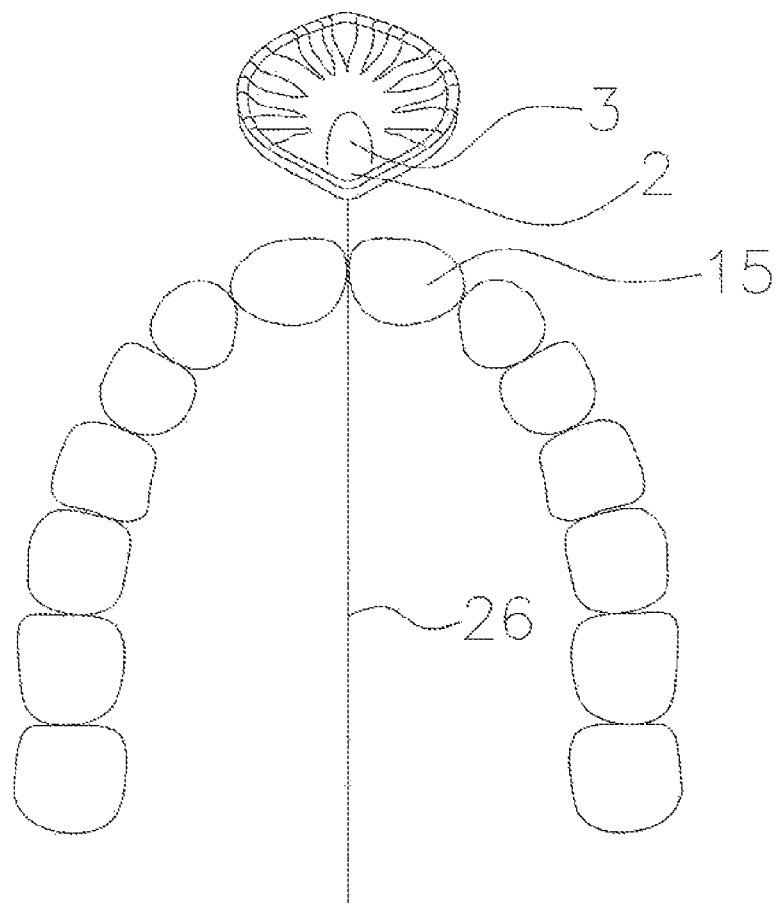
FIG. 16 is a conceptual drawing of the relative position of the AGP (on a maxillary occlusal plane mid-sagittally) to the maxillary teeth set up in the virtual environment of a virtual articulator in accordance with an exemplary embodiment.

6. For a Class I occlusion, identify a point in space that is about 6 mm anterior to the most anterior aspect of the maxillary retentive piece along the occlusal plane (a plane passing through the occlusal surfaces of the maxillary teeth) mid-sagittally 26). In some embodiments, the point in space may be between about 1 mm to about 10 mm anterior to the most aspect of the maxillary retentive piece, depending on the size of the patient's stomatognathic system and the range of motion of the patient's mandible. FIG. 16 shows the relative position of an exemplary virtual AGP 4 on a maxillary occlusal plane mid-sagittally 26.

Figure 17:
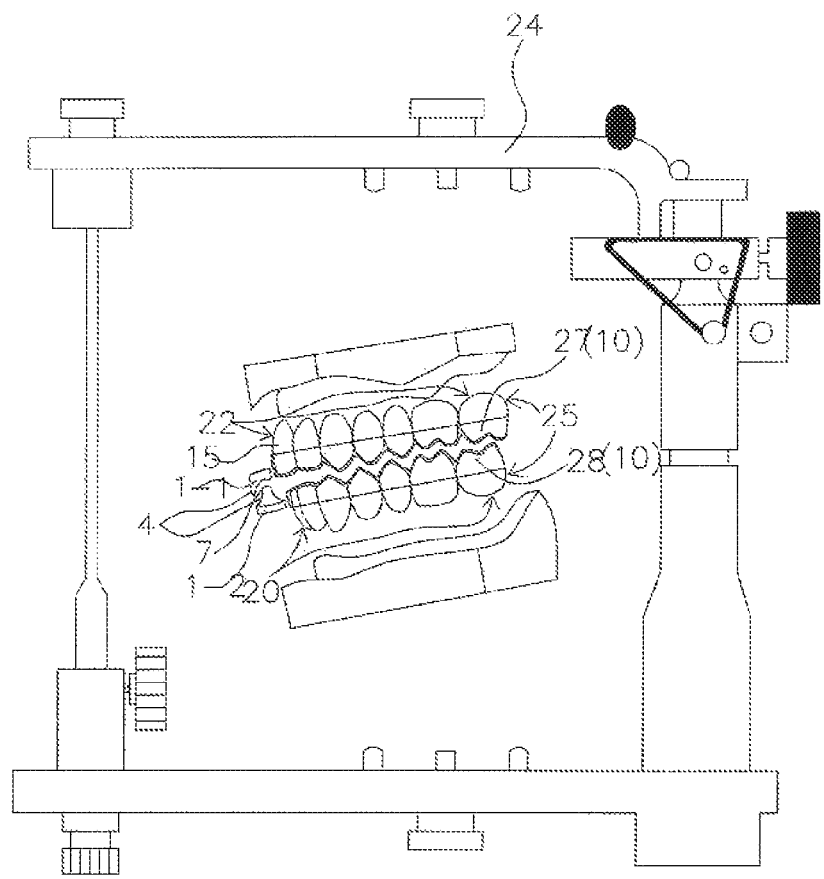
FIG. 17 is a virtual side view of the virtual AGP placed relative to the virtual retentive pieces according to the relative position in FIG. 16 in the virtual environment of a virtual articulator in accordance with an exemplary embodiment.

FIG. 17 shows an exemplary AGP 4 relative to the retentive pieces 27, 28 according to the relative position in FIG. 15. The dental professional may virtually place point 2 (see FIGS. 2, 4, 16, and 17) of an AGP 4. Virtually place point 2 at this point in space about 6 mm anterior to the most anterior aspect of the maxillary retentive piece. Point 2 may represents where protrusion 7 of the mandibular guidance component 1-2 sits at rest in the maxillary guidance component 1-1 when the condyles 8 R and L of the TMJs 9R and 9L of the mandible 8-1 are in their CR positions (e.g., the jaw is in its virtual CR), developed vertically to provide 1 mm of space between the retentive pieces (where they would otherwise contact).

In another embodiment, for instance as an example in the construction of a sleep apnea AGP splint, using a "bilateral anterior repositioning" TMD AGP 4-TB (e.g., as shown in FIG. 11), the dental professional may virtually place point 2" at a point in space 6 mm anterior to the most anterior aspect of the maxillary retentive piece. The location of Point 2", 7" (e.g., position of rest) may be coincident to a position of the mandible protrusively, laterally and vertically to provide effective airway opening, and to provide about 1 mm of space between the retentive pieces (where they would otherwise contact).

For an alternative bruxism appliance, such as the "canine guidance" AGP 4-C (e.g., as shown in FIG. 9) bruxism appliance, virtually place points 2*a* and 2*b* equidistant bilaterally, dependent upon size of the AGP 4-C, from a point about 6 mm anterior to the most anterior aspect of the maxillary retentive piece. In some embodiments, the points 2*a* and 2*b* may be between about 1 mm to about 10 mm anterior to the most anterior aspect of the maxillary retentive piece, depending on the size of the patient's stomatognathic system and the range of motion of the patient's mandible. Points 2*a* and 2*b* may represent where the protrusions 7*a* and 7*b* of the mandibular guidance component 1-2-C sits at rest in the maxillary guidance component 1-1-C when the condyles 8R and 8L of the TMJs 9R and 9L of the mandible 8-1 are in their CR positions (e.g., the jaw is in its virtual CR), developed vertically to provide 1 mm of space between the retentive pieces (where they would otherwise contact).

For another alternative bruxism appliance, such as a "group function" AGP 4G (e.g., as shown in FIG. 10), virtually place point 2' at this point in space about 6 mm anterior to the most anterior aspect of the maxillary retentive piece. In some embodiments, the point 2' may be between about 1 mm to about 10 mm anterior to the most anterior aspect of the maxillary retentive piece, depending on the size of the patient's stomatognathic system and the range of motion of the patient's mandible. Point 2' may represent where the mandibular guidance component 1-2-G 7' sits at rest in the maxillary guidance component 1-1-G when the condyles 8R and 8L of the TMJs 9R and 9L of the mandible 8-1 are in their CR positions (e.g., the jaw is in its virtual CR), developed vertically to provide 1 mm of space between the retentive pieces (where they would otherwise contact).

In other embodiments, for instance as an example in the construction of a TMD AGP splint, such as a "bilateral anterior repositioning" TMD AGP 4-TB (e.g., as shown in FIG. 11) splint, virtually place point 2" at this point in space 6 mm anterior to the most anterior aspect of the maxillary retentive piece. In some embodiments, the point 2" may be between about 1 mm to about 10 mm anterior to the most anterior aspect of the maxillary retentive piece, depending on the size of the patient's stomatognathic system and the range of motion of the patient's mandible. The location of Point 2", 7" (e.g., position of rest) may be coincident to a position of the condyles 8R and 8L within the TMJs 9R and 9L other than CR, developed protrusively, laterally and vertically to recapture the discs of both TMJs 9R and 9L and to provide about 1 mm of space between the retentive pieces (where they would otherwise contact).

In the case of the construction of a "unilateral anterior repositioning" TMD AGP 4-TU (e.g., as shown in FIG. 12) splint, virtually place points 2'*a* and 2'*b* at a distance and asymmetrically bilaterally, dependent upon size of the AGP 4-TU, from a point 6 mm anterior to the most anterior aspect of the maxillary retentive piece. In some embodiments, the points 2'a and 2'b may be between about 1 mm to about 10 mm anterior to the most anterior aspect of the maxillary retentive piece, depending on the size of the patient's stomatognathic system and the range of motion of the patient's mandible. The location of points 2'a and 2'b (e.g., position of rest) may be coincident to some position of the condyles 8R and 8L within the TMJs 9R and 9L other than CR, developed protrusively, laterally, vertically and asymmetrically so that the damaged TMJ has recaptured its' disc and the other TMJ is in a relatively normal albeit rotated state.

In the case of the construction of a "asymmetric TMD treatment" AGP 4-AT (e.g., as shown in FIGS. 13 and 13a) splint, virtually place point 2''' laterally right or left, at a distance dependent upon size, shape and orientation of the AGP 4-AT, from a point 6 mm anterior to the most anterior aspect of the maxillary retentive piece. In some embodiments, the point 2''' may be between about 1 mm to about 10 mm anterior to the most anterior aspect of the maxillary retentive piece, depending on the size of the patient's stomatognathic system and the range of motion of the patient's mandible. The location of Point 2''' (e.g., position of rest) may be determined by the dental professional for therapeutic treatment of the mandible, TMJ, or other stomatognathic malady of the mandible for that specific patient.

This point of reference for the placement of point or points 2, 2', 2'', 2''', 2a, 2b, 2'a, and 2'b of the virtual AGP could be any of the dental professional's choosing based on multiple variables, for example malocclusion, vertical dimension of rest consideration, and mechanical advantage over muscles of mastication consideration.

For a severe Class II malocclusion patient, this point or points 2, 2', 2'', 2''', 2a, 2b, 2'a, and 2'b of the virtual AGP could be placed more posterior (e.g., as shown in FIG. 7).

For a severe Class III patient, point or points 2, 2', 2'', 2''', 2a, 2b, 2'a, and 2'b of the virtual AGP could be placed further anterior (e.g., as shown in FIG. 8).

The dental professional could at this point virtually construct an AGP package of any design around Point 2, 2', 2'', 2''' or points 2a and 2b, or 2'a and 2'b and their still oriented mandibular components 1-2, 1-2-C, 1-2-G, 1-2-TB, 1-2-TU, 1-2-AT as shown in FIGS. 2, 9, 10, 11, 12, 12a, 13 and 13a. All parameters of size, shape, depth, steepness, and style of guidance can be controlled to include placement of lateral guidance 5, protrusive guidance 6, and special protrusive guidance 6a, as shown in FIGS. 2, 9, 10, 11, 12, 12a, 13 and 13a. The mandibular component may be modified regarding the number of protrusions, and the size and shape of those protrusions. The dental professional may use the border limits of the mandible to define the overall size of the AGP 4. The depth 32 of the AGP, shown in FIG. 1, can be controlled. The steepness 33, shown in FIG. 1, of the guidance can be dictated by the dental professional. In some cases, for instance as an example a TMD AGP, the guidance may be asymmetrical, specialized protrusive guidance may be included 6a (e.g., as shown in FIGS. 11, 12 and 12a), or the range of motion could also be proscribed asymmetrically (e.g., as shown in FIGS. 12, 12a, 13 and 13a). The dental professional may have a broad spectrum of three dimensional patterning available to guide the patient's mandible to a selected destination by a route chosen or designed from a broad spectrum of three dimensional routes available.

Alternatively, the dental professional could choose an AGP package from a library of stock virtual AGP package designs of different sizes and shapes. In other embodiments, the dental professional could choose and then modify a stock virtual AGP from a virtual library.

The dental professional could choose an appropriate stock virtual AGP from the virtual library and use without modification. As an example, the most common application for a bruxism AGP appliance would be to select a stock virtual AGP that is large enough to provide anterior guidance to avoid all interferences (e.g., collisions, movement restrictions) in a symmetrical way, provide mechanical advantage over the muscles of mastication, and provide a preferable minimum vertical dimension at rest in CR position.

7. Optionally, once the AGP package has been virtually modeled or chosen from a library and/or modified, a virtual functional simulation on the virtual articulator of the anterior guidance provided by the virtual AGP may be performed to verify the dental professional's goals. Many options are available in treating TMD. For a TMD, AGP splint goals could include special protrusive, lateral, and vertical guidance to manage the specific damage profile of a specific patient. In the case of a "bilateral anterior repositioning TMD AGP 4-TB splint, the objectives may be that as the patient closes his jaw special protrusive guidance is provided to bring the mandible to a position of rest 2', 7' that will recapture both discs and from that position of minimal vertical dimension at rest all excursions from that position will guide the mandible to avoid all interferences and guide the mandible in specific three dimensional pathways meant to therapeutically address the damage profile of that particular patient.

In the case of sleep apnea therapy using a "bilateral anterior repositioning" TMD AGP 4-TB splint, as shown in FIG. 11, the objectives may be that as the patient closes his jaw special protrusive guidance is provided to bring the mandible to a position of rest 2', 7' that will open the airway effectively to treat sleep apnea, and from that position of minimal vertical dimension at rest all excursions from that position will guide the mandible to avoid all interferences and guide the mandible in specific three dimensional pathways meant to therapeutically address the sleep apnea of that particular patient.

In the case of a "unilateral anterior repositioning" TMD AGP 4-TU splint, the objectives may be that as the patient closes his jaw special protrusive guidance is provided to bring the mandible to a position of rest 2'a and 2'b that will recapture the disc of the damaged TMJ and leave the other condyle in a relatively normal position albeit somewhat rotated and from that position of minimal vertical dimension of rest all excursions from that position will guide the mandible to avoid all interferences and guide the mandible in specific three dimensional pathways meant to therapeutically address the damage profile of that particular patient. In the case of an "asymmetric treatment" TMD AGP 4-AT splint, the objectives may be determined by the operator for therapeutic treatment of the mandible, TMJ, or other stomatognathic malady of the mandible for that specific patient for the position or rest 2''', 7' and from that position of minimal vertical dimension of rest all excursions from that position will guide the mandible to avoid all interferences and guide the mandible in specific three-dimensional pathways meant to therapeutically address the damage profile of that particular patient.

However most commonly, a dental professional may be creating an AGP bruxism splint, having goals of the elimination of all posterior interferences therefore eliminating destructive engrams reducing muscle spasms, protection of the teeth and TMJs, an increased mechanical advantage over the muscles of mastication, a minimal vertical dimension at centric occlusion rest position 2, 2', 2a, 2b, 7, 7', 7a, and 7b and ideal three-dimensional anterior guidance from that position creating a superior anterior guidance bruxism splint.

8. Optionally, virtually apply the shelf 11 or shelves 11 as a bridge between the special retentive pieces 10, and apply a connection as a bridge between the retentive piece 19 and the respective virtual AGP components taking care to remain inside the envelope of function of the AGP on both the maxillary and mandibular aspects of the AGP splint 13. The vertical dimension 16 for a patient at rest of the AGP splint 13 in the examples of FIGS. 6 through 8 can remain minimized irrespective of the Class of the malocclusion by fixing the relative position of the virtual shelf 11 on the frontal surface of the special retentive piece 10 of the current invention that receives the appropriate component of the AGP 4.

The AGP may enable guidance irrespective of the positions of the teeth, combined with the virtual special retentive piece and shelf, which in turn enables the dental professional to place the AGP package in a location to maximize guidance, maximize mechanical advantage over muscles of mastication, and minimize vertical dimension at rest (see FIGS. 5-*a* and 5-*b*).

As shown in FIGS. 7 and 8, the shelf 11 may receive the mandibular guidance component 1-2 of the AGP 4 for a Class II malocclusion patient and the shelf 11 receives the maxillary guidance component 1-1 of the AGP 4 for a Class III malocclusion patient. In the construction of a sleep apnea AGP appliance, the dental professional may assume a Class III malocclusion point of view in selecting the shelf because that is the end therapeutic goal. For a non-malocclusion case, Class I, as shown in FIG. 6, the shelf 11 of the special retentive piece 10 may be applied as a bridge to the respective component of the AGP for both the maxillary arch 22 and mandibular arch 20.

9. This data and information, collected from the above steps, may be transferred to a manufacturer who has CAM (Computer Aided Manufacturing) or CNC (Computer Numerical Control) technology and equipment, an in-office 3D printer, or another manufacturing or printing system. In some embodiments, a two-piece CAD-CAM AGP splint, a two-piece CAD-CAM TMD AGP splint, or a two-piece CAD-CAM sleep apnea AGP splint can be automatically produced or re-produced that is customized for a specific patient, consisting of a maxillary aspect and a mandibular aspect, which is comfortable to wear, irrespective of the malocclusion type including open bite, deep bite, cross bite, severe Class II, and Class III (see FIGS. 6 to 8).

The style, shape, steepness, depth, and size of AGP which could be stock AGP, modified from a stock AGP or specifically designed is dependent upon the problem or combination of problems and the occlusion or malocclusion that particular patient exhibits.

Figure 18:
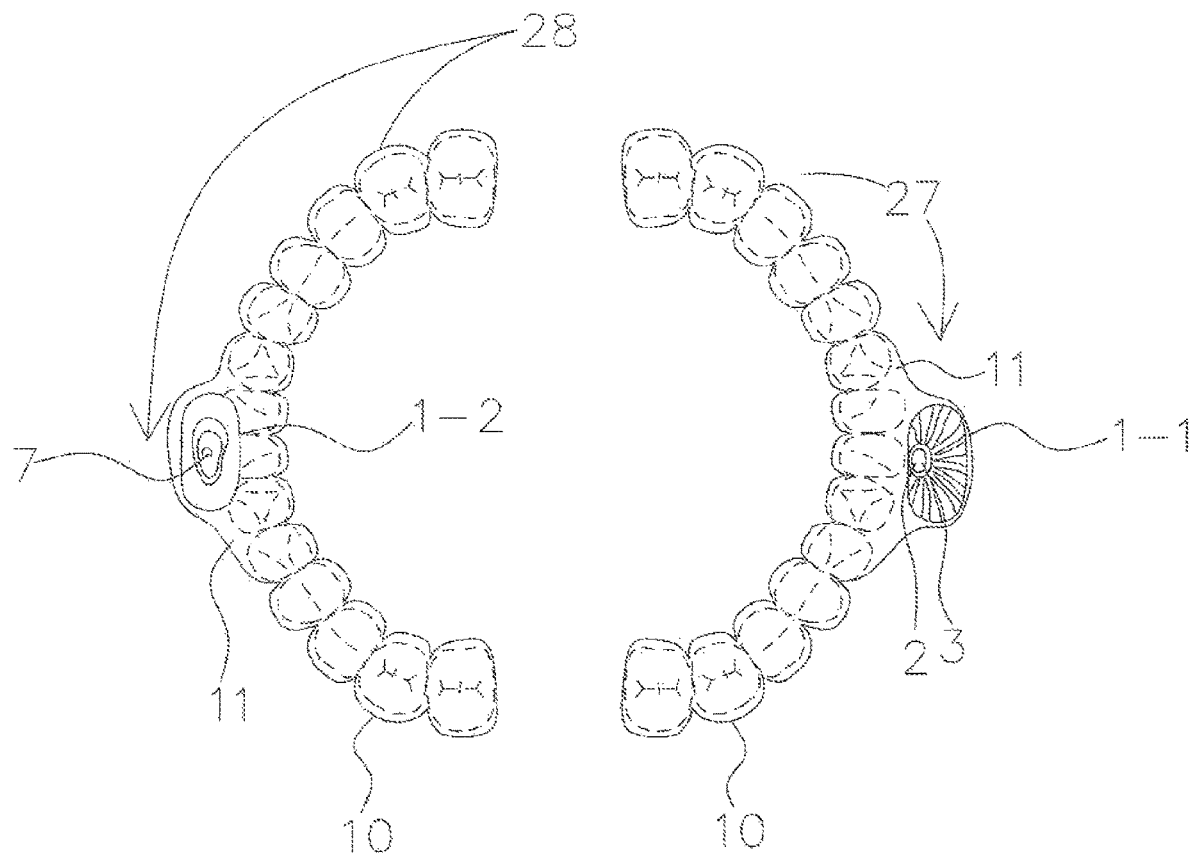
FIG. 18 is a perspective view of a completed CAD-CAM AGP splint for a patient without a severe malocclusion, Class I, from the inside of the mouth, in accordance with an exemplary embodiment.

FIG. 18 shows an exemplary completed CAD-CAM AGP splint or a CAD-CAM TMD AGP splint for a patient without a severe malocclusion, Class I, from the inside of the mouth. In this example, both the maxillary retentive piece 27 and mandibular retentive piece 28 of the CAD-CAM AGP splint may be comprised of the special retentive pieces 10. Both the maxillary and mandibular AGP splint components, including the retentive piece and the guidance portion 1-1 or 1-2 of the AGP, may be connected seamlessly by the shelves 11.

Figure 19:
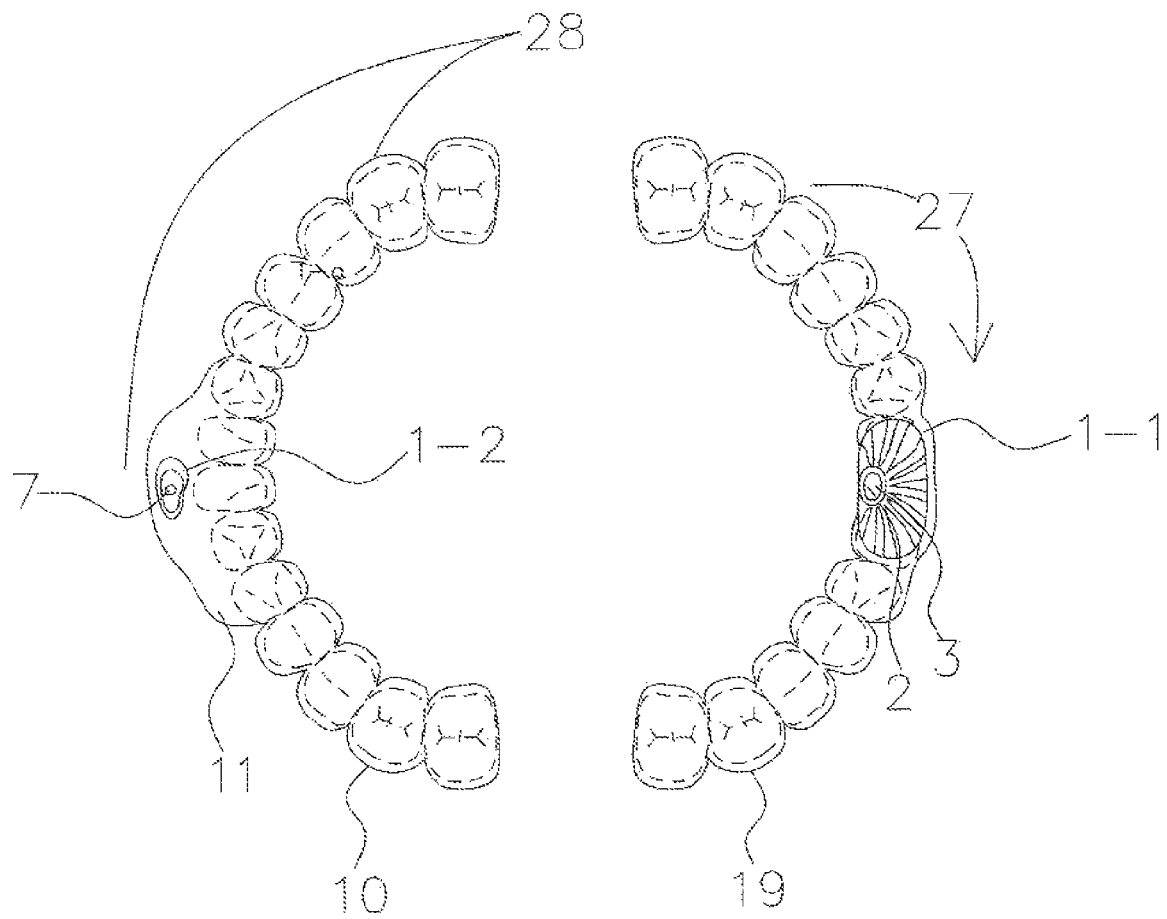
FIG. 19 is a perspective view of a completed CAD-CAM AGP splint for a patient with a Class II malocclusion from the inside of the mouth, in accordance with an exemplary embodiment.

FIG. 19 shows an exemplary completed CAD-CAM AGP splint or CAD-CAM TMD AGP splint for a patient with a severe Class II malocclusion from inside the mouth. For a severe Class II malocclusion, the mandibular retentive piece 28 may be a special retentive piece 10, which has a shelf 11 to receive the mandibular guidance component 1-2, and the maxillary retentive piece can be a regular retentive piece 19, which does not have a shelf 11 on the anterior surface.

Figure 20:
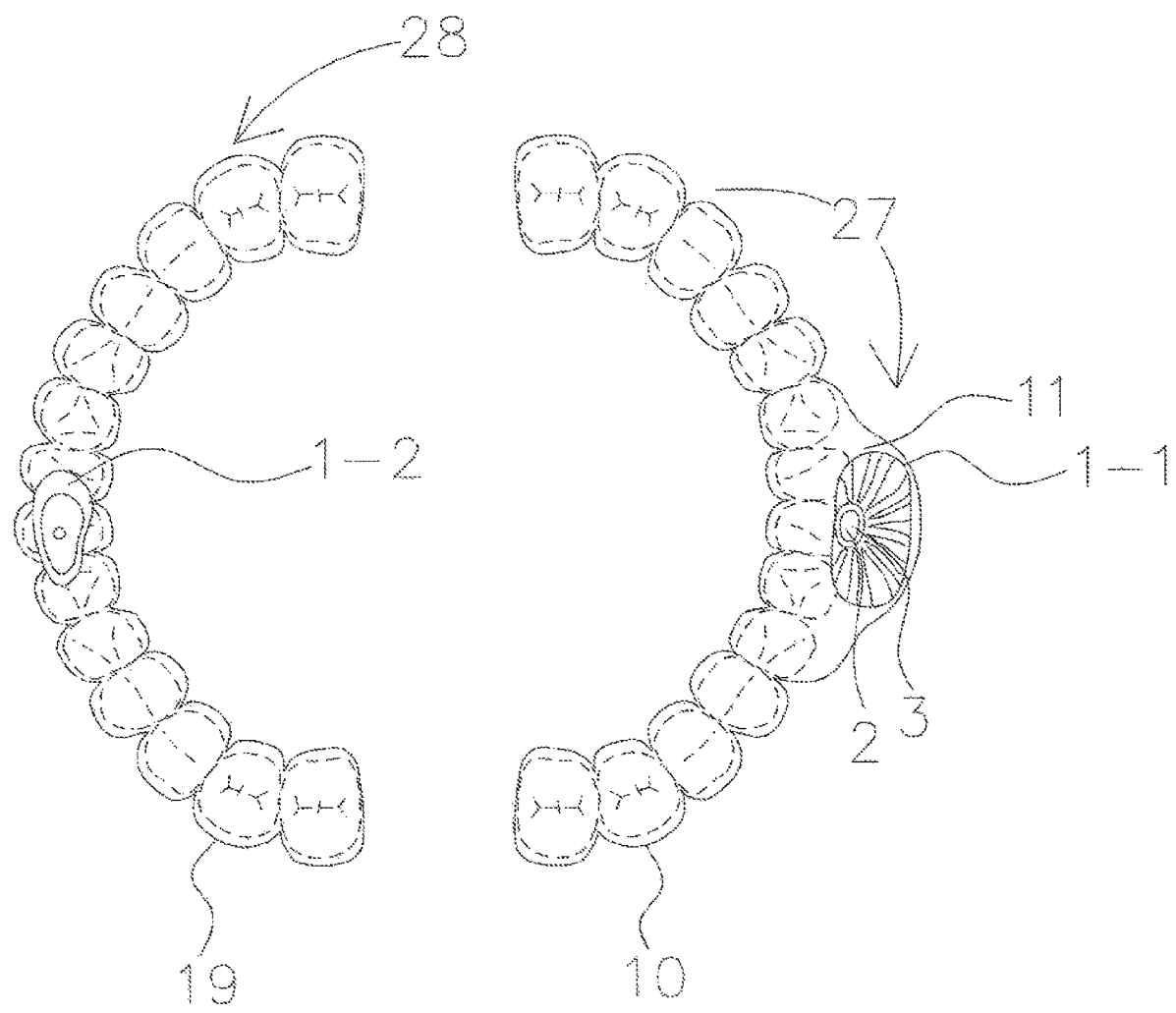
FIG. 20 is a perspective view of a completed CAD-CAM AGP splint for a patient with a Class III malocclusion from the inside of the mouth, in accordance with an exemplary embodiment.

FIG. 20 show an exemplary completed CAD-CAM AGP splint, CAD-CAM TMD AGP splint for a patient with a Class III malocclusion, or CAD-CAM sleep apnea AGP splint from inside the mouth. For a Class III malocclusion or for treatment of sleep apnea, the maxillary retentive piece 27 may be a special retentive piece 10, which has a shelf 11 to receive the maxillary guidance component 1-1, and the mandibular retentive piece can be a regular retentive piece 19.

Located in the mouth with a minimal vertical dimension 16 penalty at rest in CR, or any position of the dental professional's choosing, a custom AGP splint may be composed of thin custom-fitting retentive pieces and the attached AGP 4, 4-C, 4-G, 4-TB, 4-TU, or 4-AT. The AGP portion of the splint 13 may be positioned in a smooth compartment-like package between the patient's lips, anterior to the teeth in most cases dependent upon the malocclusion, and therefore, the position of the AGP in relation to teeth and lips. As the patient's mouth closes, the maxillary component of the AGP splint may contact the mandibular component guiding the mandible into Point 2, 2', 2", 2'" or Points 2a and 2b, or 2'a and 2'b and area 3, 3', 3", 3'", as shown in FIGS. 2, 4, 9, 10, 11, 12, 12a, 13 and 13a. This index position area would most commonly be CR (e.g., Point 2 in FIG. 4, Points 2a and 2b in FIG. 9, Point 2' in FIG. 10) and the long centric area (e.g., Area 3 and 3' in FIGS. 4, 9, and 10) but could in the case of a TMD AGP management splint, a stomatognathic treatment TMD AGP splint, or a sleep apnea AGP splint, be a position other than CR proscribed by the dental professional (e.g., Point 2" in FIG. 11 and Point 2'" in FIGS. 13 and 13a, or Points 2'a and 2'b in FIGS. 12 and 12a). The maxillary component 1-1, 1-1-C, 1-1-G, 1-1-TB, 1-1-TU, 1-1-AT of the AGP may fit over the mandibular component 1-2, 1-2-C, 1-2-G, 1-2-TB, 1-2-TU, 1-2-AT. The entire inferior perimeter of the maxillary component of the AGP may be wider than the mandibular aspect of the AGP and its housing. That perimeter 1-4 in FIG. 2 may also have a thickness between about 2 mm to about 6 mm and be shaped like a bumper to prevent the lips from ever being pinched when the patients' mouth closes. In other embodiments, the perimeter 1-4 may have a thickness between about 1 mm to about 10 mm.

11. Finally, when the various AGP 4, 4-C, 4-G, 4-TB, 4-TU, and 4-AT (e.g., as shown in FIGS. 1, 9, 10, 11, 12, 12a, 13 and 13a) splints for patients with different malocclusions are manufactured by the CAD-CAM method, all the retentive pieces 27, 28 and their respective AGP components 1-1, 1-1-C, 1-1-G, 1-1-TB, 1-1-TU, 1-1-AT or 1-2, 1-2-C, 1-2-G, 1-2-TB, 1-2-TU, 1-2-AT may be produced in one piece without any seam lines.

Figure 21:
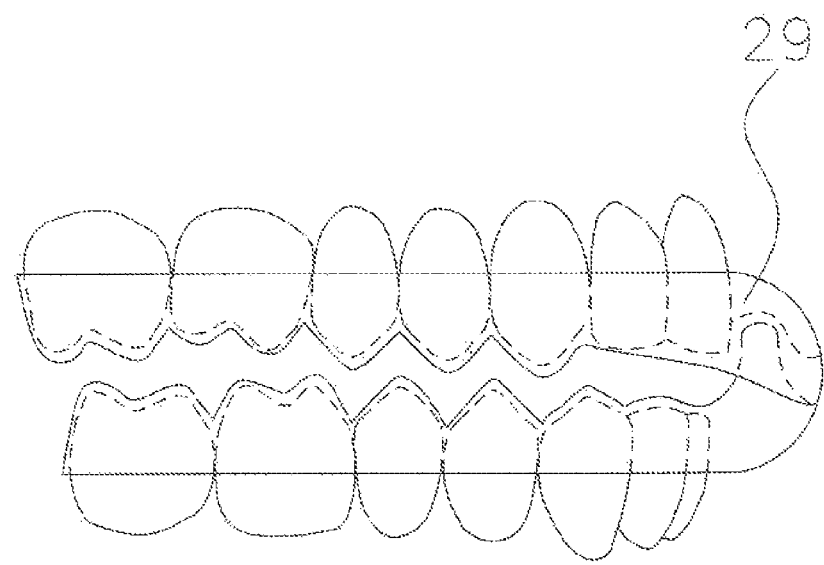
FIG. 21 is a schematic side view of a finished CAD-CAM AGP splint for a bruxism or TMD patient without a severe malocclusion, Class I, in accordance with an exemplary embodiment.

FIG. 21 shows an exemplary finished CAD-CAM AGP splint 29, which may have special properties to manage a TMD patient, or a splint for a bruxism patient without a severe malocclusion, Class I and with or without sleep apnea. Compared with FIG. 6, it is simpler to produce and much simpler to reproduce.

Figure 22:
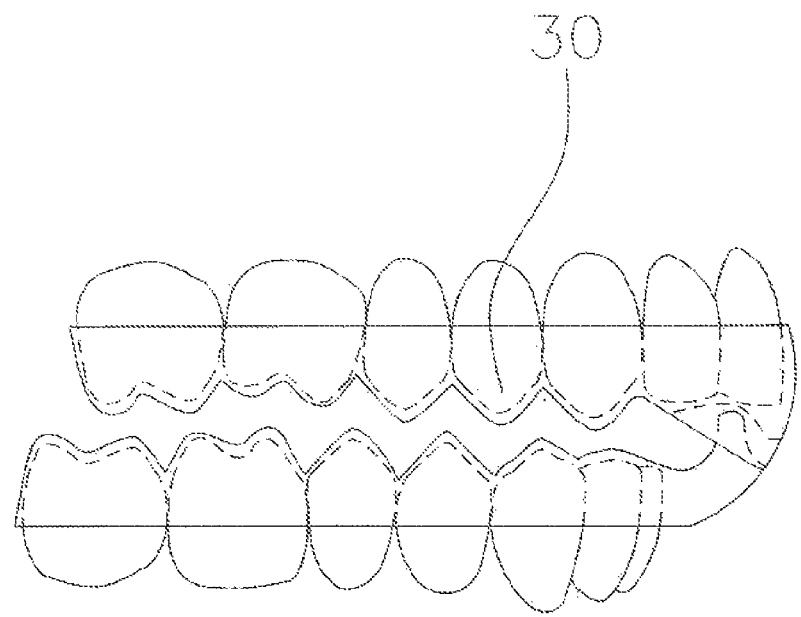
FIG. 22 is a schematic side view of a finished CAD-CAM AGP splint for a bruxism or TMD patient with a Class II malocclusion, in accordance with an exemplary embodiment.
Figure 23:
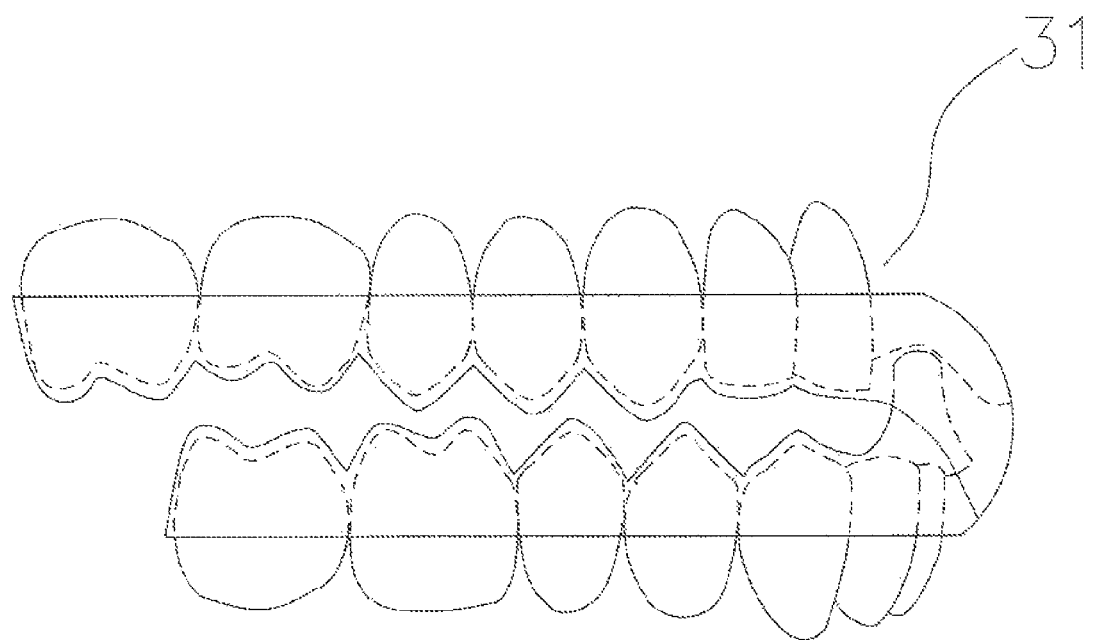
FIG. 23 is a schematic side view of a finished CAD-CAM AGP splint for a bruxism or TMD patient with a Class III malocclusion, in accordance with an exemplary embodiment.

Similarly, FIG. 22 shows an exemplary finished CAD-CAM AGP 30 splint that may have special properties to manage a TMD patient, a bruxism patient with Class II malocclusion, or a sleep apnea patient with a Class II malocclusion. FIG. 23 shows an exemplary CAD-CAM AGP splint 31, which may have special properties to manage a TMD patient, a bruxism patient with a Class III malocclusion, or a sleep apnea patient.

FIGS. 24-a, 24-b, and 24-c show an exemplary positioning of the virtual point(s) relative to one or more of the maxillary and mandibular retentive pieces in the sagittal axis. In FIG. 24-a, for a patient without a severe malocclusion, Class 1, regular retentive pieces 19 may be placed on the maxillary arch 22 and mandibular arch 20, with the maxillary arch 22 extending anteriorly beyond the mandibular arch 20 (albeit slightly). In FIG. 24-b, for a patient with a Class II malocclusion, the regular retentive piece 19 may be placed are placed on the mandibular arch 20, while the special retentive piece 10 may be placed on the maxillary arch 22. In FIG. 24-c, for a patient with a Class III malocclusion, the special retentive piece 10 may be placed are placed on the mandibular arch 20, while the regular retentive piece 19 may be placed on the maxillary arch 22.

Positioned between the arches 20, 22, a plurality of potential virtual points 40 may designate contact points between AGP maxillary and mandibular guidance components. In some embodiments, one or more of the AGP guidance components may be set based on a virtual point 40 such that when the AGP guidance components contact, the virtual maxillary and mandibular arches 22, 20 are placed in the predetermined index position. In some embodiments, the potential virtual points 40 may include one or more interior virtual points 42, edge virtual points 44, and anterior virtual points 46. The interior virtual point(s) 42 may not provide an ideal vertical dimension at rest, may provide the least mechanical advantage over muscles of mastication, and may interfere with other functions of the mouth. The edge virtual point(s) 44 may not provide an ideal vertical dimension at rest, may provide limited mechanical advantage over muscles of mastication, and may or may not interfere with other functions of the mouth. The anterior virtual point(s) 46 may provide optimal placement that enables ideal vertical dimension at rest, the greatest mechanical advantage over the muscles of mastication, and minimum interference with other functions of the mouth.

Figure 25:
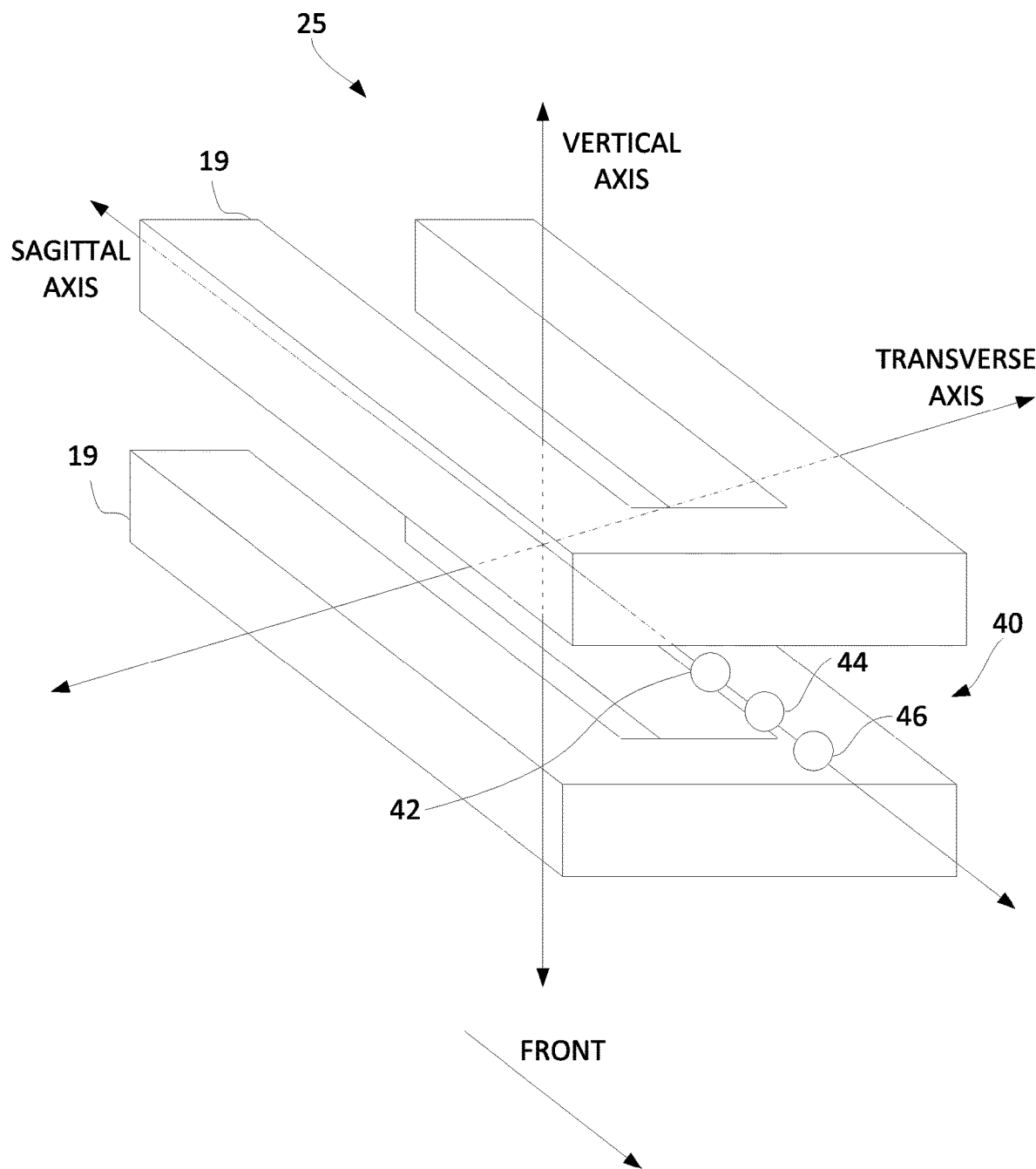
FIG. 25 is a conceptual drawing of potential positions of a single virtual point along the transverse plane between the maxillary and mandibular retentive pieces for a bruxism or TMD patient without a severe malocclusion, Class I, in accordance with an exemplary embodiment.
Figure 26:
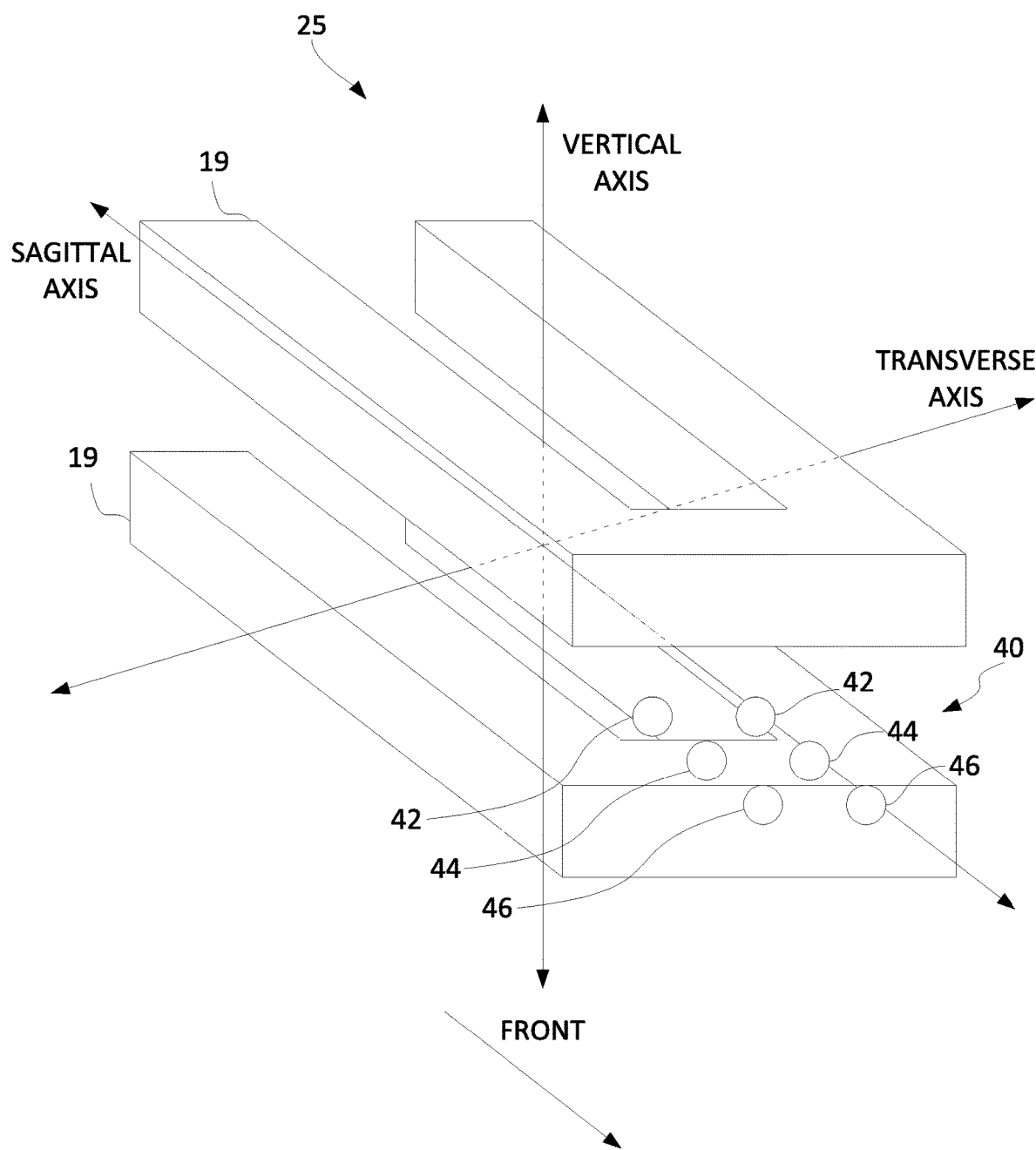
FIG. 26 is a conceptual drawing of potential positions of a pair of virtual points along the transverse plane between the maxillary and mandibular retentive pieces for a bruxism or TMD patient without a severe malocclusion, Class I, in accordance with an exemplary embodiment.

FIGS. 25 and 26 provide a three dimensional view of the exemplary regular retentive pieces 19 for a patient without a severe malocclusion, Class 1, as shown in FIG. 24-a. In FIG. 25, a single virtual point (e.g., one of the interior virtual point 42, edge virtual point 44, or anterior virtual point 46) may be positioned between the retentive pieces proximate the sagittal axis (e.g., along the mid-sagittal plane). Alternatively, as shown in FIG. 26, a pair of virtual points (e.g., two interior virtual points 42, edge virtual points 44, or anterior virtual points 46) may be positioned between the retentive pieces proximate the sagittal axis (e.g., along the mid-sagittal plane). The pair of virtual points may be asymmetrically positioned in relation to the mid-sagittal plane. The virtual point(s) may be positioned proximate a vertical plane perpendicular to the mid-sagittal plane. In some embodiments, the vertical plane may be positioned about six millimeters anterior to the most anterior aspect of the maxillary retentive piece along an occlusal plane mid-sagittally.

Figure 27:
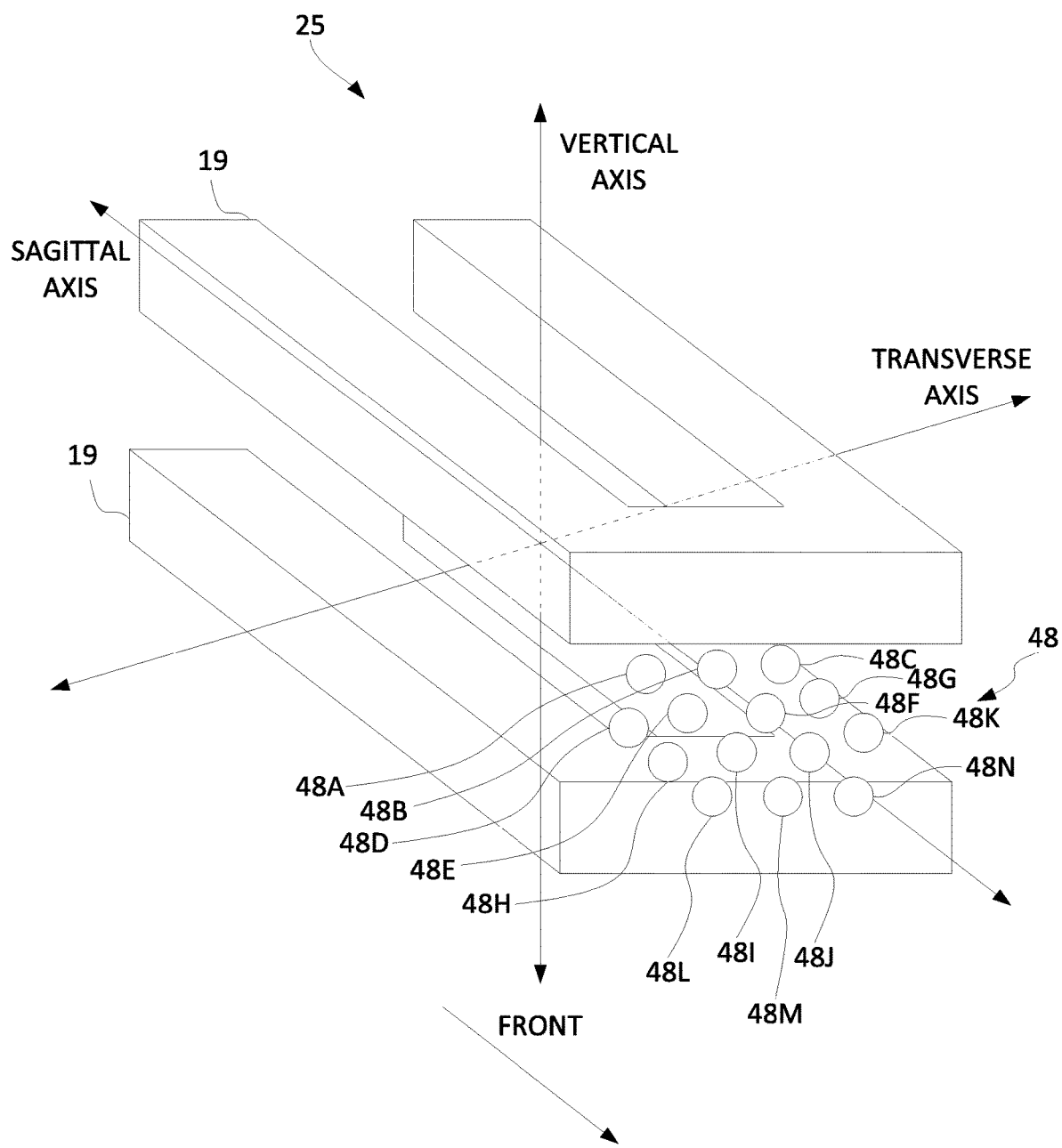
FIG. 27 is a conceptual drawing of potential positions of a single virtual point inside a virtual envelope bordered transversely, sagittally, and vertically by the three dimensional criterion for selecting that virtual point.

FIG. 27 shows the plurality of potential locations in all three axes (e.g., sagittal, vertical, and transverse) for a virtual point or points, which may better enable an operator to use an unmodified virtual stock AGP or require less customization of the stock AGP. In other words, allowing a dental practitioner to select any position in three dimensional virtual space as the virtual point maximizes the range of orientation, alignment, and position that a stock AGP may be used to fit a particular patient. As shown, a virtual point 48 may be placed anywhere in three dimensional virtual space, for example as any of potential virtual point positions 48A-N. It is contemplated that, while the virtual point 48 may be proximate mid-sagittal and occlusal planes, it may be placed anywhere in three dimensional space to accommodate any disease, deformity, damage, area requiring treatment, and the like. Further, a series of AGP splints may be used to progressively treat and/or correct any damage, and the series of AGP splints may be virtually designed and produced without requiring extensive customization of physical splints by trial and error. In one exemplary embodiment, the first AGP splint in a series may have a virtual point proximate position 48A, while a later AGP splint in the series may have a virtual point proximate position 48F, which is closer to an exemplary "ideal position" proximate the mid-sagittal and occlusal planes.

Figure 28:
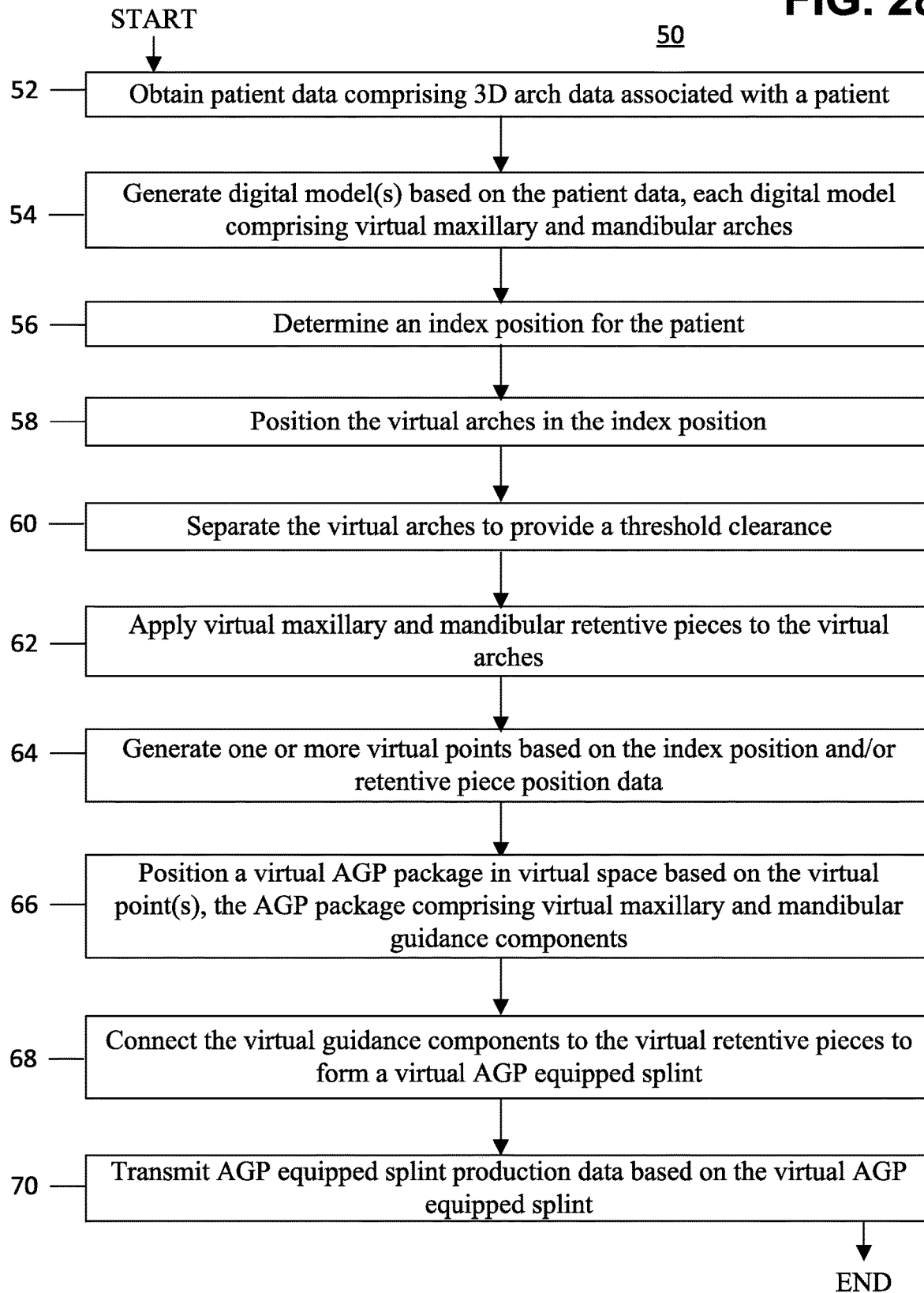
FIG. 28 is a flowchart for a method for preparing an AGP equipped splint for a patient with one or more of bruxism, TMD, and sleep apnea, in accordance with an exemplary embodiment.

FIG. 28 is a flowchart of an exemplary method 50 for preparing an AGP equipped splint for a patient with one or more of bruxism, TMD, and sleep apnea. As shown, the method 50 may include obtaining patient data 52 comprising three dimensional arch data associated with the patient. After obtaining the patient data, one or more digital models may be generated 54 on one or more processors based on the patient data. The one or more digital models may include virtual maxillary and mandibular arches. The method 50 may also include determining an index position 56 for the patient. The virtual arches may be positioned 58 in the index position. Further, the method 50 may include separating the virtual arches 60 to provide a threshold clearance. Virtual maxillary and mandibular retentive pieces may be applied 62 to their respective virtual maxillary and mandibular retentive pieces. One or more virtual points may be generated 64 based on the index position and/or retentive piece position data (e.g., one of more of orientation, alignment, and position data for at least one of the virtual retentive pieces). A virtual AGP package may be positioned 66 in virtual space based on the one or more virtual points. The AGP package may include a virtual maxillary guidance component and a virtual mandibular guidance component. After positioning the AGP package 66 in virtual space, the virtual maxillary and mandibular guidance components may be connected 68 to their respective virtual retentive pieces to form a virtual AGP equipped splint. AGP equipped splint production data based on the virtual AGP equipped splint can then be transmitted 70. For example, the AGP equipped splint production data may be transmitted to a manufacturer equipped with one or more of CAM, CNC technology, and an in-office 3D printer.

In some embodiments, it is contemplated that steps of the method may be reordered or removed as the AGP splint may be customized or further customized by the dental professional. For example, in some embodiments, a virtual point may be arbitrarily generated in virtual space, and the virtual AGP components and/or the virtual retentive pieces can be positioned or adjusted to fit with the virtual point. In other embodiments, a virtual point that requires modification of the AGP component(s) may be generated in lieu of a virtual point that allows for use of a stock AGP. In practice, a dental professional may customize any feature of the AGP splints, including the location and contact point(s) of the AGP components.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A method for preparing an Anterior Guidance Package (AGP) equipped splint for a patient with one or more of bruxism, temporomandibular disorder (TMD), and sleep apnea, the method comprising:
   obtaining patient data comprising three dimensional arch data associated with the patient;
   generating one or more digital models on one or more processors based on the patient data, the one or more digital models comprising virtual maxillary and mandibular arches;
   determining an index position for the patient;
   positioning the virtual maxillary and mandibular arches in the index position;
   separating the virtual maxillary and mandibular arches based on an arc of closure associated with the patient to provide a threshold clearance;
   applying a virtual maxillary retentive piece to the virtual maxillary arch and a virtual mandibular retentive piece to the virtual mandibular arch;
   generating one or more virtual points based on the index position;
   positioning a virtual AGP package in virtual space based on the one or more virtual points, the AGP package comprising a virtual maxillary guidance component and a virtual mandibular guidance component;
   connecting the virtual maxillary guidance component to the virtual maxillary retentive piece to form a first part of a virtual AGP equipped splint;
   connecting the virtual mandibular guidance component to the virtual mandibular retentive piece to form a second part of the virtual AGP equipped splint; and
   transmitting AGP equipped splint production data based on the first and second parts of the virtual AGP equipped splint.

2. The method of claim 1, wherein at least one of the mandibular guidance component and the maxillary guidance component is positioned about an anterior aspect of the mandibular retentive piece and the maxillary retentive piece, respectively.

3. The method of claim 1, wherein generating the one or more virtual points comprises positioning the one or more virtual points to provide a clearance of at least 1 mm between the virtual maxillary retentive piece and the virtual mandibular retentive piece.

4. The method of claim 1, further comprising virtually simulating movement of the virtual AGP equipped splint by opening and closing the virtual maxillary and mandibular arches based on the arc of closure associated with the patient while the first art of the virtual AGP equipped splint is applied to the virtual maxillary arch and the second part of the virtual AGP equipped splint is applied to the virtual mandibular arch.

5. The method of claim 1, wherein generating the one or more virtual points comprises generating one virtual point proximate a reference plane positioned from a most anterior aspect of at least one of the virtual retentive pieces along the occlusal plane mid-sagittally, the reference plane being perpendicular to a mid-sagittal plane, and connecting one of the virtual guidance components to its respective virtual retentive piece is based on the virtual point and at least one of an orientation, an alignment, and a position of the other virtual retentive piece.

6. The method of claim 1, wherein:
   obtaining patient data further comprises obtaining temporomandibular joint (TMJ) data associated with left and right TMJs of the patient;
   generating the one or more virtual points comprises generating one virtual point proximate a reference plane positioned from a most anterior aspect of at least one of the virtual retentive pieces along an occlusal plane mid-sagittally, the reference plane being perpendicular to a mid-sagittal plane;
   positioning the virtual AGP package in virtual space comprises positioning, based on the virtual point, the virtual AGP package in an AGP index position such that the mandible is placed outside of centric relation and is configured to protrusively, laterally, and vertically recapture the left and right TMJ discs; and
   connecting one of the virtual guidance components to its respective virtual retentive piece is based on the AGP index position and at least one of an orientation, an alignment, and a position of the other virtual retentive piece.

7. The method of claim 6, wherein one of the left and right TMJ condyles must travel further than the other TMJ condyle for disc recapture.

8. The method of claim 1, wherein:
   obtaining patient data further comprises obtaining temporomandibular joint (TMJ) data associated with left and right TMJs of the patient, one of the left and right TMJ discs being damaged;
   generating the one or more virtual points comprises asymmetrically positioning two virtual points in relation to a mid-sagittal plane proximate a plane perpendicular to the mid-sagittal plane that is positioned anterior to a most anterior aspect of at least one of the virtual retentive pieces along an occlusal plane mid-sagittally;
   positioning the virtual AGP package in virtual space comprises positioning, based on the two virtual points, the virtual AGP package in an AGP index position such that the mandible is configured to recapture the damaged TMJ disc; and
   connecting one of the virtual guidance components to its respective virtual retentive piece is based on the AGP index position and at least one of an orientation, an alignment, and a position of the other virtual retentive piece.

9. The method of claim 1, wherein:
   obtaining patient data further comprises obtaining damaged structure data associated with the patient;
   generating the one or more virtual points comprises positioning one virtual point proximate a mid-sagittal plane and proximate a plane perpendicular to the mid-sagittal plane that is positioned anterior to a most anterior aspect of at least one of the virtual retentive pieces along an occlusal plane mid-sagittally;
   positioning the virtual AGP package in virtual space comprises positioning, based on the virtual point, the virtual AGP package in an AGP index position configured to treat one or more of a mandible, a temporomandibular joint (TMJ), and a stomatognathic condition of the patient based on the damaged structure data; and connecting one of the virtual guidance components to its respective virtual retentive piece is based on the AGP index position and at least one of an orientation, an alignment, and a position of the other virtual retentive piece.

10. The method of claim 9, wherein the damaged structure data indicates that one of a left side or a right side of a mandible of the patient is damaged, and positioning the virtual AGP package in virtual space comprises protrusively moving the damaged side of the mandible to advance a condyle of the damaged side out of a centric relation position while laterally moving the undamaged side of the mandible to keep a condyle of the undamaged side in the centric relation position.

11. The method of claim 1, wherein generating the one or more virtual points comprises positioning two virtual points bilaterally equidistant from a reference plane, the reference plane being positioned from a most anterior aspect of at least one of the virtual retentive pieces along an occlusal plane, and connecting one of the virtual guidance components to its respective virtual retentive piece is based on the two virtual points.

12. The method of claim 11, wherein the reference plane is perpendicular to a mid-sagittal plane.

13. The method of claim 11, wherein the reference plane is positioned 6 mm from the most anterior aspect of the at least one of the virtual retentive pieces along the occlusal plane mid-sagittally.

14. The method of claim 11, wherein connecting one of the virtual guidance components to its respective virtual retentive piece is further based on at least one of an orientation, an alignment, and a position of the other virtual retentive piece.

15. The method of claim 1, wherein generating the one or more virtual points comprises generating one virtual point proximate a reference plane positioned from a most anterior aspect of at least one of the virtual retentive pieces along the occlusal plane, and connecting one of the virtual guidance components to its respective virtual retentive piece is based on the virtual point.

16. The method of claim 1, wherein
generating the one or more virtual points comprises generating one virtual point proximate a reference plane positioned from a most anterior aspect of at least one of the virtual retentive pieces along an occlusal plane; and
positioning the virtual AGP package in virtual space comprises positioning, based on the virtual point, the virtual AGP package.

17. A system for preparing an Anterior Guidance Package (AGP) equipped splint for a patient with one or more of bruxism, temporomandibular disorder (TMD), and sleep apnea, the system comprising:
a data module configured to obtain patient data comprising three dimensional arch data associated with the patient;
a modeling module configured to generate one or more digital models on one or more processors based on the patient data, the one or more digital models comprising virtual maxillary and mandibular arches;
a determination module configured to determine an index position for the patient;
an arch positioning module configured to position the virtual maxillary and mandibular arches in the index position;
a separation module configured to separate the virtual maxillary and mandibular arches based on an arc of closure associated with the patient to provide a threshold clearance;
an application module configured to apply a virtual maxillary retentive piece to the virtual maxillary arch and a virtual mandibular retentive piece to the virtual mandibular arch;
a generation module configured to generate one or more virtual points based on one or more of the index position and retentive piece position data, the retentive piece position data comprising one or more of orientation, alignment, and position data for at least one of the virtual retentive pieces;
an AGP positioning module configured to position a virtual AGP package in virtual space based on the one or more virtual points, the AGP package comprising a virtual maxillary guidance component and a virtual mandibular guidance component;
a maxillary connection module configured to connect the virtual maxillary guidance component to the virtual maxillary retentive piece to form a first part of a virtual AGP equipped splint;
a mandibular connection module configured to connect the virtual mandibular guidance component to the virtual mandibular retentive piece to form a second part of the virtual AGP equipped splint; and
a transmission module configured to transmit AGP equipped splint production data based on the first and second parts of the virtual AGP equipped splint.

18. The system of claim 17, wherein:
the AGP positioning module is further configured to position at least one of the mandibular guidance component and the maxillary guidance component about an anterior aspect of the mandibular retentive piece and the maxillary retentive piece, respectively; and
the generation module is further configured to position the one or more virtual points to provide a clearance of at least 1 mm between the virtual maxillary retentive piece and the virtual mandibular retentive piece.

19. A non-transitory computer-readable storage medium having stored computer-executable instructions that, when executed by one or more processors, cause a computer to perform functions of:
obtaining patient data comprising three dimensional arch data associated with the patient;
generating one or more digital models on one or more processors based on the patient data, the one or more digital models comprising virtual maxillary and mandibular arches;
determining an index position for the patient;
positioning the virtual maxillary and mandibular arches in the index position;
separating the virtual maxillary and mandibular arches based on an arc of closure associated with the patient to provide a threshold clearance;
applying a virtual maxillary retentive piece to the virtual maxillary arch and a virtual mandibular retentive piece to the virtual mandibular arch;
generating one or more virtual points based on one or more of the index position and retentive piece position data, the retentive piece position data comprising one or more of orientation, alignment, and position data for at least one of the virtual retentive pieces;

positioning a virtual AGP package in virtual space based on the one or more virtual points, the AGP package comprising a virtual maxillary guidance component and a virtual mandibular guidance component;

connecting the virtual maxillary guidance component to the virtual maxillary retentive piece to form a first part of a virtual AGP equipped splint;

connecting the virtual mandibular guidance component to the virtual mandibular retentive piece to form a second part of the virtual AGP equipped splint; and transmitting AGP equipped splint production data based on the first and second parts of the virtual AGP equipped splint.

20. The non-transitory computer-readable storage medium of claim 19, wherein generating the one or more virtual points comprises positioning one virtual point proximate a reference plane positioned from a most anterior aspect of at least one of the virtual retentive pieces along an occlusal plane mid-sagittally, the reference plane being perpendicular to a mid-sagittal plane, and connecting one of the virtual guidance components to its respective virtual retentive piece is based on the virtual point and the retentive piece position data associated with the other virtual retentive piece.

* * * * *